(12) United States Patent
Smith et al.

(10) Patent No.: US 8,153,397 B2
(45) Date of Patent: Apr. 10, 2012

(54) RECOMBINANT LIGHT CHAINS OF BOTULINUM NEUROTOXINS AND LIGHT CHAIN FUSION PROTEINS FOR USE IN RESEARCH AND CLINICAL THERAPY

(75) Inventors: Leonard A. Smith, Clarksburg, MD (US); Melody Jensen, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/387,014

(22) Filed: Apr. 27, 2009

(65) Prior Publication Data

US 2010/0273211 A1    Oct. 28, 2010

Related U.S. Application Data

(60) Division of application No. 11/293,582, filed on Dec. 2, 2005, now abandoned, which is a division of application No. 10/011,588, filed on Nov. 6, 2001, now Pat. No. 7,037,680, which is a continuation-in-part of application No. 09/910,186, filed on Jul. 20, 2001, now Pat. No. 7,081,529, which is a continuation of application No. 09/611,419, filed on Jul. 6, 2000, now Pat. No. 7,214,787, which is a continuation of application No. 08/123,975, filed on Sep. 21, 1993, now abandoned.

(60) Provisional application No. 60/246,774, filed on Nov. 6, 2000, provisional application No. 60/311,966, filed on Aug. 9, 2001.

(51) Int. Cl.
| | |
|---|---|
| C12P 21/06 | (2006.01) |
| C12P 21/04 | (2006.01) |
| C12N 15/09 | (2006.01) |
| C12N 1/12 | (2006.01) |
| C12N 1/20 | (2006.01) |
| C12N 1/14 | (2006.01) |
| C12N 15/00 | (2006.01) |
| C12N 15/63 | (2006.01) |
| C07H 21/02 | (2006.01) |
| C07H 21/04 | (2006.01) |

(52) U.S. Cl. ............... 435/69.1; 435/69.7; 435/69.3; 435/70.1; 435/71.1; 435/71.2; 435/842; 435/252.3; 435/252.33; 435/254.23; 435/252.1; 435/320.1; 536/23.1; 536/23.4; 536/23.7; 536/24.1

(58) Field of Classification Search .................. None
See application file for complete search history.

(56) References Cited

U.S. PATENT DOCUMENTS

| | | | | |
|---|---|---|---|---|
| 6,967,088 | B1 * | 11/2005 | Williams et al. | 435/69.1 |
| 7,037,680 | B2 * | 5/2006 | Smith et al. | 435/69.1 |
| 7,081,529 | B2 * | 7/2006 | Smith et al. | 536/23.7 |
| 7,214,787 | B1 * | 5/2007 | Smith et al. | 536/23.7 |
| 7,227,010 | B2 * | 6/2007 | Smith | 536/23.7 |
| 7,534,863 | B2 * | 5/2009 | Steward et al. | 530/350 |
| 7,632,917 | B2 * | 12/2009 | Kincaid et al. | 530/300 |
| 7,786,285 | B2 * | 8/2010 | Smith et al. | 536/23.7 |
| 7,820,411 | B2 * | 10/2010 | Baldwin et al. | 435/71.3 |
| 7,825,233 | B2 * | 11/2010 | Steward et al. | 536/23.7 |
| 2009/0017495 | A1 * | 1/2009 | Baldwin et al. | 435/69.3 |
| 2010/0196421 | A1 * | 8/2010 | Ichtchenko et al. | 424/239.1 |
| 2010/0273211 | A1 * | 10/2010 | Smith et al. | 435/69.1 |

OTHER PUBLICATIONS

Kadkhodayan et al, Protein Expression and Purification, Jun. 2000, 19/1:125-130.*

* cited by examiner

*Primary Examiner* — Nita M Minnifield
(74) *Attorney, Agent, or Firm* — Elizabeth Arwine

(57) ABSTRACT

The present invention relates to the construction, expression, and purification of synthetic or recombinant light chain (LC) botulinum neurotoxin genes from all botulinum neurotoxin serotypes. The methods of the invention can provide 1.1 g of the LC per liter of culture. The LC product is stable and proteolytically active. Methods of using the products of the invention are described.

18 Claims, 20 Drawing Sheets

| Purification of LcA, LcA+Belt, and LcA+Hn from *E. coli* cells | | | |
|---|---|---|---|
| Purification Step | Protein Conc. (mg/ml) | Volume (mL) | Percentage of desired protein in solute |
| LcA | | | |
| Load column 1 | 1.764 | 35 | 10% |
| Load column 2 | 0.557 | 12 | 85% |
| Peak column 2 | 0.748 | 4 | >95% |
| | | | |
| LcA+Belt | | | |
| Load column 1 | 1.749 | 35 | 7% |
| Load column 2 | 0.454 | 12 | 90% |
| Peak column 2 | 0.226 | 4 | >95% |
| | | | |
| LcA+Hn | | | |
| Load column 1 | 1.799 | 35 | 5% |
| Load column 2 | 0.816 | 12 | 85% |
| Peak column 2 | 0.401 | 4 | >95% |
| | | | |
| LcB | | | |
| Load column 1 | 1.42 | 20 | 9% |
| Load column 2 | 0.79 | 8 | 85% |
| Peak column 2 | 1.032 | 2 | >95% |

*Fig. 18*

```
                            SEQUENCE LISTING

<160> NUMBER OF SEQ ID NOS: 47

<210> SEQ ID NO 1
<211> LENGTH: 16
<212> TYPE: PRT
<213> ORGANISM: Clostridium botulinum
<220> FEATURE:
<221> NAME/KEY: PEPTIDE
<222> LOCATION: (0)...(0)
<223> OTHER INFORMATION: N-terminal residues of mature, wild-type
      botulinum neurotoxin

<400> SEQUENCE: 1

Pro Phe Val Asn Lys Gln Phe Asn Tyr Lys Asp Pro Val Asn Gly Val
1               5                   10                  15

<210> SEQ ID NO 2
<211> LENGTH: 17
<212> TYPE: PRT
<213> ORGANISM: Human
<220> FEATURE:
<221> NAME/KEY: PEPTIDE
<222> LOCATION: (0)...(0)
<223> OTHER INFORMATION: Residues 187-203 of SNAP-25

<400> SEQUENCE: 2

Ser Asn Lys Thr Arg Ile Asp Glu Ala Asn Gln Arg Ala Thr Lys Met
1               5                   10                  15

Leu

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide; control for phosphorylation
      experiments

<400> SEQUENCE: 3

Lys Val Glu Lys Ile Gly Glu Gly Thr Gly Val Val Tyr Lys
1               5                   10

<210> SEQ ID NO 4
<211> LENGTH: 1403
<212> TYPE: DNA
<213> ORGANISM: Artificial Sequence
<220> FEATURE:
<223> OTHER INFORMATION: Synthetic botulinum neurotoxin light chain of
      serotype A based on wild-type Clostridium
      botulinum sequence

<400> SEQUENCE: 4
gaattcccat ggttcagttc gttaacaaac agttcaacta caaagacccg gttaacggtg      60
ttgacatcgc ttcatcaaa atcccgaacg ttggtcagat gcagccggtt aaagcattca     120
aaatccacaa caaaatctgg gttatcccgg aacgtgacac tttcactaac ccggaagaag     180
```

-continued

```
gtgacctgaa cccgccgccg gaagctaaac aggttccggt ttcttactac gactctactt    240
acctgtctac tgacaacgaa aaggacaact acctgaaagg tgttactaaa ctgtttgaac    300
gtatctactc tactgacctg gtcgcatgc tgctcacttc tatcgttcgt ggtatcccgt     360
tctggggtgg ttctactatc gacactgaac tgaaagttat cgacactaac tgcatcaacg    420
ttatccagcc ggacggttct taccgttctg aagaactgaa cctggttatc atcggtccgt    480
ctgctgacat catccagttt gaatgcaaat ctttcggtca cgaagttctg aacctgactc    540
gtaacggtta cggttctact cagtacatcc gtttctctcc ggacttcact ttcggtttcg    600
aagaatctct ggaagttgac actaacccgc tgctgggtgc tggtaaattc gctactgacc    660
cggctgttac tctggctcac gaactgatcc acgctggtca ccgtctgtac ggtatcgcta    720
tcaacccgaa ccgtgttttc aaagttaaca ctaacgctta ctacgaaatg tctggtctgg    780
aagtttcttt tgaagaactg cgtacttttcg gtggtcacga cgctaaattc atcgactctc    840
tgcaggaaaa cgagttccgt ctgtactact acaacaaatt caaagacatc gcttctactc    900
tgaacaaagc taaatctatc gttggtacca ctgcttctct gcagtacatg aagaacgttt    960
tcaaagaaaa gtacctgctg tctgaagaca cttctggtaa attctctgtt gacaaactga   1020
aattcgacaa actgtacaaa atgctgactg aaatctacac tgaagacaac ttcgttaaat   1080
tcttcaaagt tctgaaccgt aaaacttacc tgaacttcga caaagctgtt ttcaaaatca   1140
acatcgttcc gaaagttaac tacactatct cgacggtttt caacctgcgt aacactaacc   1200
tggctgctaa cttcaacggt cagaacactg aaatcaacaa catgaacttc actaaactga   1260
agaacttcac tggtctgttt gagttctaca aactgctgtg cgttcgtggt atcatcactt   1320
ctaaaactaa atctctggac aaaggttaca acaaactggt tccgcgtggt tctcatcatc   1380
atcatcatca ttaatgagaa tcc                                           1403
```

<210> SEQ ID NO 5
<211> LENGTH: 461
<212> TYPE: PRT
<213> ORGANISM: Artificial Sequence
<220> FEATURE:
<223> OTHER INFORMATION: Synthetic botulinum neurotoxin light chain of
      serotype A based on wild-type Clostridium
      botulinum sequence

<400> SEQUENCE: 5

```
Met Val Gln Phe Val Asn Lys Gln Phe Asn Tyr Lys Asp Pro Val Asn
 1               5                  10                  15

Gly Val Asp Ile Ala Tyr Ile Lys Ile Pro Asn Val Gly Gln Met Gln
            20                  25                  30

Pro Val Lys Ala Phe Lys Ile His Asn Lys Ile Trp Val Ile Pro Glu
        35                  40                  45

Arg Asp Thr Phe Thr Asn Pro Glu Glu Gly Asp Leu Asn Pro Pro
    50                  55                  60

Glu Ala Lys Gln Val Pro Val Ser Tyr Tyr Asp Ser Thr Tyr Leu Ser
65                  70                  75                  80

Thr Asp Asn Glu Lys Asp Asn Tyr Leu Lys Gly Val Thr Lys Leu Phe
                85                  90                  95

Glu Arg Ile Tyr Ser Thr Asp Leu Gly Arg Met Leu Leu Thr Ser Ile
            100                 105                 110

Val Arg Gly Ile Pro Phe Trp Gly Gly Ser Thr Ile Asp Thr Glu Leu
        115                 120                 125

Lys Val Ile Asp Thr Asn Cys Ile Asn Val Ile Gln Pro Asp Gly Ser
```

```
                  130                 135                 140
Tyr Arg Ser Glu Glu Leu Asn Leu Val Ile Ile Gly Pro Ser Ala Asp
145                 150                 155                 160

Ile Ile Gln Phe Glu Cys Lys Ser Phe Gly His Glu Val Leu Asn Leu
                165                 170                 175

Thr Arg Asn Gly Tyr Gly Ser Thr Gln Tyr Ile Arg Phe Ser Pro Asp
                180                 185                 190

Phe Thr Phe Gly Phe Glu Glu Ser Leu Glu Val Asp Thr Asn Pro Leu
                195                 200                 205

Leu Gly Ala Gly Lys Phe Ala Thr Asp Pro Ala Val Thr Leu Ala His
                210                 215                 220

Glu Leu Ile His Ala Gly His Arg Leu Tyr Gly Ile Ala Ile Asn Pro
225                 230                 235                 240

Asn Arg Val Phe Lys Val Asn Thr Asn Ala Tyr Tyr Glu Met Ser Gly
                245                 250                 255

Leu Glu Val Ser Phe Glu Glu Leu Arg Thr Phe Gly Gly His Asp Ala
                260                 265                 270

Lys Phe Ile Asp Ser Leu Gln Glu Asn Glu Phe Arg Leu Tyr Tyr Tyr
                275                 280                 285

Asn Lys Phe Lys Asp Ile Ala Ser Thr Leu Asn Lys Ala Lys Ser Ile
                290                 295                 300

Val Gly Thr Thr Ala Ser Leu Gln Tyr Met Lys Asn Val Phe Lys Glu
305                 310                 315                 320

Lys Tyr Leu Leu Ser Glu Asp Thr Ser Gly Lys Phe Ser Val Asp Lys
                325                 330                 335

Leu Lys Phe Asp Lys Leu Tyr Lys Met Leu Thr Glu Ile Tyr Thr Glu
                340                 345                 350

Asp Asn Phe Val Lys Phe Phe Lys Val Leu Asn Arg Lys Thr Tyr Leu
                355                 360                 365

Asn Phe Asp Lys Ala Val Phe Lys Ile Asn Ile Val Pro Lys Val Asn
                370                 375                 380

Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
                405                 410                 415

Leu Lys Asn Phe Thr Gly Leu Phe Glu Phe Tyr Lys Leu Leu Cys Val
                420                 425                 430

Arg Gly Ile Ile Thr Ser Lys Thr Lys Ser Leu Asp Lys Gly Tyr Asn
                435                 440                 445

Lys Leu Val Pro Arg Gly Ser His His His His His
                450                 455                 460

<210> SEQ ID NO 6
<211> LENGTH: 1323
<212> TYPE: DNA
<213> ORGANISM: Artificial Sequence
<220> FEATURE:
<223> OTHER INFORMATION: Synthetic botulinum neurotoxin light chain of
      serotype B based on wild-type Clostridium
      botulinum sequence

<400> SEQUENCE: 6
atgccagtta ctattaacaa cttcaactac aacgacccaa ttgacaacaa caacattatt      60
atgatggagc caccattcgc tagaggtact ggtagatact acaaggcttt caagattact     120
gacagaattt ggattattcc agagagatac actttcggtt acaagccaga ggacttcaac     180
```

-continued

```
aagtcttctg gtattttcaa cagagacgtt tgtgagtact acgacccaga ctacttgaac    240
actaacgaca agaagaacat tttcttgcaa actatgatta agttgttcaa cagaattaag    300
tctaagccat tgggtgagaa gttgttggag atgattatta acggtattcc atacttgggt    360
gacagaagag ttccattgga ggagttcaac actaacattg cttctgttac tgttaacaag    420
ttgatttcta acccaggtga ggttgagaga aagaagggta ttttcgctaa cttgattatt    480
ttcggtccag gtccagtttt gaacgagaac gagactattg acattggtat tcaaaaccac    540
ttcgcttcta gagagggttt cggtggtatt atgcaaatga agttctgtcc agagtacgtt    600
tctgttttca acaacgttca agagaacaag ggtgcttcta ttttcaacag aagaggttac    660
ttctctgacc cagctttgat tttgatgcac gagttgattc acgttttgca cggtttgtac    720
ggtattaagg ttgacgactt gccaattgtt ccaaacgaga agaagttctt catgcaatct    780
actgacgcta ttcaagctga ggagttgtac actttcggtg gtcaagaccc atctattatt    840
actccatcta ctgacaagtc tatttacgac aaggttttgc aaaacttcag aggtattgtt    900
gacagattga acaaggtttt ggtttgtatt tctgacccaa acattaacat taacatttac    960
aagaacaagt tcaaggacaa gtacaagttc gttgaggact ctgagggtaa gtactctatt    1020
gacgttgagt ctttcgacaa gttgtacaag tctttgatgt tcggtttcac tgagactaac    1080
attgctgaga actacaagat taagactaga gcttcttact tctctgactc tttgccacca    1140
gttaagatta agaacttgtt ggacaacgag atttacacta ttgaggaggg tttcaacatt    1200
tctgacaagg acatggagaa ggagtacaga ggtcaaaaca aggctattaa caagcaagct    1260
tacgaggaga tttctaagga gcacttggct gtttacaaga ttcaaatgtg taagtctgtt    1320
aag                                                                  1323
```

<210> SEQ ID NO 7
<211> LENGTH: 441
<212> TYPE: PRT
<213> ORGANISM: Artificial Sequence
<220> FEATURE:
<223> OTHER INFORMATION: Synthetic botulinum neurotoxin light chain of
      serotype B based on wild-type Clostridium
      botulinum sequence

<400> SEQUENCE: 7

```
Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
```

```
            145                 150                 155                 160
Phe Gly Pro Gly Pro Val Leu Asn Glu Asn Glu Thr Ile Asp Ile Gly
                165                 170                 175
Ile Gln Asn His Phe Ala Ser Arg Glu Gly Phe Gly Gly Ile Met Gln
                180                 185                 190
Met Lys Phe Cys Pro Glu Tyr Val Ser Val Phe Asn Asn Val Gln Glu
                195                 200                 205
Asn Lys Gly Ala Ser Ile Phe Asn Arg Arg Gly Tyr Phe Ser Asp Pro
            210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Ala Ile Gln Ala Glu Glu Leu Tyr Thr Phe
                260                 265                 270
Gly Gly Gln Asp Pro Ser Ile Ile Thr Pro Ser Thr Asp Lys Ser Ile
                275                 280                 285
Tyr Asp Lys Val Leu Gln Asn Phe Arg Gly Ile Val Asp Arg Leu Asn
            290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
                340                 345                 350
Met Phe Gly Phe Thr Glu Thr Asn Ile Ala Glu Asn Tyr Lys Ile Lys
                355                 360                 365
Thr Arg Ala Ser Tyr Phe Ser Asp Ser Leu Pro Pro Val Lys Ile Lys
            370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys
            435                 440

<210> SEQ ID NO 8
<211> LENGTH: 1332
<212> TYPE: DNA
<213> ORGANISM: Artificial Sequence
<220> FEATURE:
<223> OTHER INFORMATION: Synthetic botulinum neurotoxin light chain of
      serotype C1 based on wild-type Clostridium
      botulinum sequence

<400> SEQUENCE: 8
atgccaatca ccatcaacaa cttcaactac tcagaccctg tcgacaacaa gaacattctg      60
tacctggaca ctcacctgaa caccctagct aacgagcctg agaaggcctt tcggatcacc     120
ggaaacatct gggtcatccc tgatcgtttc tcccgtaact ccaaccccaa cctgaacaag     180
cctcctcggg tcaccagccc taagagtggt tactacgacc taactacct gagtaccgac     240 tctgacaagg acacctcct gaaggagatc atcaagctgt tcaagcgtat caactcccgt     300
gagatcggag aggagctcat ctacagactt tcgaccgata tccccttccc tggtaacaac     360
```

```
aatactccaa tcaacacctt cgacttcgac gtcgacttca actccgtcga cgtcaagact    420
cggcagggta acaactgggt taagactggt agcatcaacc cttccgtcat catcactgga    480
cctcgtgaga acatcatcga cccagagact tccacgttca agctgactaa caacaccttc    540
gcggctcaag aaggattcgg tgctctgtca atcatctcca tctcacctcg tttcatgctg    600
acctactcga acgcaaccaa cgacgtcgga gagggtaggt tctctaagtc tgagttctgc    660
atggacccaa tcctgatcct gatgcatgag ctgaaccatg caatgcacaa cctgtacgga    720
atcgctatcc caaacgacca gaccatctcc tccgtgacct ccaacatctt ctactcccag    780
tacaacgtga gctggagta cgcagagatc tacgctttcg aggtccaac tatcgacctt    840
atccctaagt ccgctaggaa gtacttcgag gagaaggctt tggattacta cagatccatc    900
gctaagagac tgaacagtat caccaccgca aacccttcca gcttcaacaa gtacatcggt    960
gagtacaagc agaagctgat cagaaagtac cgtttcgtcg tcgagtcttc aggtgaggtc   1020
acagtaaacc gtaacaagtt cgtcgagctg tacccagat cttcacagag   1080
ttcaactacg ctaagatcta caacgtccag aacaggaaga tctacctgtc caacgtgtac   1140
actccggtga cggcgaacat cctggacgac aacgtctacg acatccagaa cggattcaac   1200
atccctaagt ccaacctgaa cgtactattc atgggtcaaa acctgtctcg aaacccagca   1260
ctgcgtaagg tcaaccctga gaacatgctg tacctgttca ccaagttctg ccacaaggca   1320
atcgacggta ga                                                       1332
```

<210> SEQ ID NO 9
<211> LENGTH: 444
<212> TYPE: PRT
<213> ORGANISM: Artificial Sequence
<220> FEATURE:
<223> OTHER INFORMATION: Synthetic botulinum neurotoxin light chain of
      serotype C1 based on wild-type Clostridium
      botulinum sequence

<400> SEQUENCE: 9

```
Met Pro Ile Thr Ile Asn Asn Phe Asn Tyr Ser Asp Pro Val Asp Asn
 1               5                  10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
```

```
                        180                 185                 190
Ser Ile Ser Pro Arg Phe Met Leu Thr Tyr Ser Asn Ala Thr Asn Asp
            195                 200                 205
Val Gly Glu Gly Arg Phe Ser Lys Ser Glu Phe Cys Met Asp Pro Ile
        210                 215                 220
Leu Ile Leu Met His Glu Leu Asn His Ala Met His Asn Leu Tyr Gly
225                 230                 235                 240
Ile Ala Ile Pro Asn Asp Gln Thr Ile Ser Ser Val Thr Ser Asn Ile
                245                 250                 255
Phe Tyr Ser Gln Tyr Asn Val Lys Leu Glu Tyr Ala Glu Ile Tyr Ala
            260                 265                 270
Phe Gly Gly Pro Thr Ile Asp Leu Ile Pro Lys Ser Ala Arg Lys Tyr
        275                 280                 285
Phe Glu Glu Lys Ala Leu Asp Tyr Tyr Arg Ser Ile Ala Lys Arg Leu
    290                 295                 300
Asn Ser Ile Thr Thr Ala Asn Pro Ser Ser Phe Asn Lys Tyr Ile Gly
305                 310                 315                 320
Glu Tyr Lys Gln Lys Leu Ile Arg Lys Tyr Arg Phe Val Val Glu Ser
                325                 330                 335
Ser Gly Glu Val Thr Val Asn Arg Asn Lys Phe Val Glu Leu Tyr Asn
            340                 345                 350
Glu Leu Thr Gln Ile Phe Thr Glu Phe Asn Tyr Ala Lys Ile Tyr Asn
        355                 360                 365
Val Gln Asn Arg Lys Ile Tyr Leu Ser Asn Val Tyr Thr Pro Val Thr
    370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
                405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg
        435                 440

<210> SEQ ID NO 10
<211> LENGTH: 1323
<212> TYPE: DNA
<213> ORGANISM: Artificial Sequence
<220> FEATURE:
<223> OTHER INFORMATION: Synthetic botulinum neurotoxin light chain of
      serotype D based on wild-type Clostridium
      botulinum sequence

<400> SEQUENCE: 10
atgacctggc cagtcaagga cttcaactac tccgacccag tcaacgacaa cgacatcttg      60
tacttgagaa tcccacaaaa caagttgatc accaccccag tcaaggcttt catgatcacc     120
cagaacacct gggttatccc agagagattc cctccgaca ccaacccatc cctgtccaag      180
ccaccaagac aacctccaa gtaccagtct tactacgacc catcttactt gtctaccgac      240
gagcaaaagg acaccttctt gaagggtatt atcaagctgt tcagagaat caacgagaga     300 gacatcggta agaagttgat caactacttg gtcgttggtt ccccattcat gggtgactcc     360
tctaccccag aggacaccct cgacttcacc agacacacca ccaacattgc cgtcgagaag    420
ttcgagaacg gttcctggaa ggtcaccaac atcatcaccc catctgtttt gatcttcggt    480
ccattgccaa acatcttgga ctacaccgcc tccctgacct gcaaggtca gcaatccaac     540
```

```
ccatccttcg agggtttcgg taccctgtct attttgaagg tcgctccaga gttcttgttg    600
accttctccg acgtcaccct caaccaatcc tccgccgtct tgggtaagtc catcttctgt    660
atggacccag tcatcgcttt gatgcacgag ttgacccact ccctgcacca gttgtacggt    720
attaacatcc catctgacaa agaaatcaga ccacaggtct ctgagggttt cttctcccaa    780
gacggtccaa acgttcagtt cgaggagttg tacaccttcg gtggtttgga cgtcgagatt    840
atccaaattg agagatccca attgagagag aaggctttgg gtcactacaa ggacatcgcc    900
aagagactga acaacatcaa caagaccatt ccatcttcct ggatctccaa cattgacaag    960
tacaagaaga ttttctccga agtacaac ttcgacaagg acaacaccgg taacttcgtc    1020
gttaacatcg acaagttcaa ctctttgtac tccgacttga ccaacgttat gtctgaggtt    1080
gtctactcct cccaatacaa cgtcaagaac agaaccccact acttctccag acactacttg    1140
ccagttttcg ctaacatctt ggacgacaac atttacacca tcagagacgg tttcaacttg    1200
accaacaagg gtttcaacat cgagaactcc ggtcaaaaca tcgagagaaa cccagccctg    1260
caaaagctgt cctccgagtc tgtcgtcgac ttgttccacca aggtctgttt gagattgacc    1320
aag                                                                 1323
```

<210> SEQ ID NO 11
<211> LENGTH: 441
<212> TYPE: PRT
<213> ORGANISM: Artificial Sequence
<220> FEATURE:
<223> OTHER INFORMATION: Synthetic botulinum neurotoxin light chain of
      serotype D based on wild-type Clostridium
      botulinum sequence

<400> SEQUENCE: 11

```
Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Thr Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
```

```
                    210                 215                 220
Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Gln Ile Glu Arg Ser Gln Leu
        275                 280                 285

Arg Glu Lys Ala Leu Gly His Tyr Lys Asp Ile Ala Lys Arg Leu Asn
    290                 295                 300

Asn Ile Asn Lys Thr Ile Pro Ser Ser Trp Ile Ser Asn Ile Asp Lys
305                 310                 315                 320

Tyr Lys Lys Ile Phe Ser Glu Lys Tyr Asn Phe Asp Lys Asp Asn Thr
                325                 330                 335

Gly Asn Phe Val Val Asn Ile Asp Lys Phe Asn Ser Leu Tyr Ser Asp
            340                 345                 350

Leu Thr Asn Val Met Ser Glu Val Val Tyr Ser Ser Gln Tyr Asn Val
        355                 360                 365

Lys Asn Arg Thr His Tyr Phe Ser Arg His Tyr Leu Pro Val Phe Ala
    370                 375                 380

Asn Ile Leu Asp Asp Asn Ile Tyr Thr Ile Arg Asp Gly Phe Asn Leu
385                 390                 395                 400

Thr Asn Lys Gly Phe Asn Ile Glu Asn Ser Gly Gln Asn Ile Glu Arg
                405                 410                 415

Asn Pro Ala Leu Gln Lys Leu Ser Ser Glu Ser Val Val Asp Leu Phe
            420                 425                 430

Thr Lys Val Cys Leu Arg Leu Thr Lys
        435                 440

<210> SEQ ID NO 12
<211> LENGTH: 1266
<212> TYPE: DNA
<213> ORGANISM: Artificial Sequence
<220> FEATURE:
<223> OTHER INFORMATION: Synthetic botulinum neurotoxin light chain of
      serotype E based on wild-type Clostridium
      botulinum sequence

<400> SEQUENCE: 12
atgccaaaga ttaactcctt caactacaac gaccctgtca acgacagaac catcttgtac      60
atcaagccag gcggttgcca ggagttctac aagtccttca acatcatgaa gaacatctgg     120
atcatccccg agagaaacgt cattggtacc accccccaag acttccaccc ccctacttcc     180
ttgaagaacg gagactccag ttactacgac cctaactact tgcaaagtga cgaggagaag     240
gacagattct tgaagatcgt cacaaagatc ttcaacagaa tcaacaacaa cctttcagga     300
ggcatcttgt tggaggagct gtccaaggct aacccatact tgggcaacga caacactcca     360
gataaccagt ccacattggt gacgcatcc gcagttgaga ttaagttctc caacggtagc     420
caggacatcc tattgcctaa cgttatcatc atgggagcag agcctgactt gtttgagacc     480
aactcctcca catctctct acgtaacaac tacatgccaa gcaatcacgg tttcggatcc     540
atcgctatcg tcaccttctc ccctgaatat tccttcaggt tcaacgacaa cagcatgaac     600
gagttcattc aggatcctgc tctcacgctg atgcacgaat tgatccactc cttacatgga     660
ctatatggcg ctaagggcat tactaccaag tacactatca cacagaagca gaaccccta     720
```

```
ataaccaaca tccggggtac caacatcgag gagttcttga ctttcggagg tactgacttg    780
aacatcatta ctagtgctca gtccaacgac atctacacta accttctggc tgactacaag    840
aagatcgcgt ctaagcttag caaggtccaa gtctctaacc cactgcttaa cccttacaag    900
gacgtcttcg aagcaaagta tggattggac aaggatgcta gcggaattta ctcggtcaac    960
atcaacaagt tcaacgacat cttcaagaag ctctacagct tcacggagtt cgacttggcc   1020
accaagttcc aggttaagtg taggcagact tacatcggac agtacaagta cttcaagctg   1080
tccaacctgt tgaacgactc tatctacaac atctcagaag ctacaacat caacaacttg   1140 aaggtcaact tcagaggaca gaatgcaaac ttgaaccta gaatcattac cccaatcacc   1200
ggtagaggac tggtcaagaa gatcatccgt ttctgcaaga acattgtctc tgtcaagggc   1260
atcagg                                                               1266
```

<210> SEQ ID NO 13
<211> LENGTH: 422
<212> TYPE: PRT
<213> ORGANISM: Artificial Sequence
<220> FEATURE:
<223> OTHER INFORMATION: Synthetic botulinum neurotoxin light chain of
      serotype E based on wild-type Clostridium
      botulinum sequence

<400> SEQUENCE: 13

```
Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255
```

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
        290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg
            420

<210> SEQ ID NO 14
<211> LENGTH: 1308
<212> TYPE: DNA
<213> ORGANISM: Artificial Sequence
<220> FEATURE:
<223> OTHER INFORMATION: Synthetic botulinum neurotoxin light chain of
      serotype F based on wild-type Clostridium
      botulinum sequence

<400> SEQUENCE: 14
atgccagtcg ctatcaactc cttcaactac aacgacccag tcaacgacga caccattttg     60
tacatgcaga tcccatacga ggagaagtct aagaagtact acaaggcttt cgagatcatg    120
agaaacgtct ggattatcga gagaaacacc atcggtacca acccatccga cttcgaccca    180
ccagcctctt tgaagaacgg ttcctccgct tactacgacc aaactacttt gaccaccgac    240
gccgagaagg acagatactt gaagaccacc atcaagttgt tcaagagaat taactctaac    300
ccagccggta aggtcttgtt gcaagagatc tcctacgcta agccatacct gggtaacgac    360
cacaccccaa ttgacgagtt ctccccagtc accagaacca cctccgtcaa catcaagtct    420
accaacgttg agtcctccat gttgttgaac ttgttggttc tgggtgctgg tccagacatt    480
ttcgagtctt gttgttaccc agtcagaaag ctgatcgacc agacgttgt ttacgaccca    540 tctaactacg gtttcggttc cattaacatc gttaccttct ctccagagta cgagtacacc    600
ttcaacgaca tctccggtgg tcacaactcc tccaccgagt ctttcattgc tgacccagcc    660
atctccctgg ctcacgagct gattcacgct ttgcacggtt tgtacggtgc tagaggtgtc    720
acctacgagg agaccattga ggtcaagcaa gcccattga tgatcgccga aagccaatc    780 agattggagg agttcttgac cttcggtggt caggacttga acatcatcac ctccgctatg    840
aaggagaaga tctacaacaa cctgctggcc aactacgaga gattgccac cagattgtcc    900 gaggtcaact ctgccccacc agagtacgac atcaacgagt acaaggacta cttccaatgg    960
aagtacggtt tggacaagaa cgccgacggt tcctacaccg tcaacgagaa caagtccaac   1020
gagatttaca gaagttgta ctctttcacc gagtccgacc tggctaacaa gttcaaggtt   1080

```
aagtgtagaa acacctactt catcaagtac gagttcttga aggttccaaa cctgttggac   1140
gacgacatct acaccgtttc tgagggtttc aacatcggta acttggctgt caacaacaga   1200
ggtcagtcca ttaagctgaa cccaaagatc attgactccc cagacaaggg tctggttgag   1260
aagattgtca agttctgtaa gtccgtcatc ccaagaaagg gtaccaag                1308
```

<210> SEQ ID NO 15
<211> LENGTH: 436
<212> TYPE: PRT
<213> ORGANISM: Artificial Sequence
<220> FEATURE:
<223> OTHER INFORMATION: Synthetic botulinum neurotoxin light chain of
      serotype F based on wild-type Clostridium
      botulinum sequence

<400> SEQUENCE: 15

```
Met Pro Val Ala Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
             20                  25                  30

Tyr Tyr Lys Ala Phe Glu Ile Met Arg Asn Val Trp Ile Ile Glu Arg
         35                  40                  45

Asn Thr Ile Gly Thr Asn Pro Ser Asp Phe Asp Pro Pro Ala Ser Leu
     50                  55                  60

Lys Asn Gly Ser Ser Ala Tyr Tyr Asp Pro Asn Tyr Leu Thr Thr Asp
 65                  70                  75                  80

Ala Glu Lys Asp Arg Tyr Leu Lys Thr Thr Ile Lys Leu Phe Lys Arg
                 85                  90                  95

Ile Asn Ser Asn Pro Ala Gly Lys Val Leu Leu Gln Glu Ile Ser Tyr
            100                 105                 110

Ala Lys Pro Tyr Leu Gly Asn Asp His Thr Pro Ile Asp Glu Phe Ser
        115                 120                 125

Pro Val Thr Arg Thr Thr Ser Val Asn Ile Lys Ser Thr Asn Val Glu
    130                 135                 140

Ser Ser Met Leu Leu Asn Leu Leu Val Leu Gly Ala Gly Pro Asp Ile
145                 150                 155                 160

Phe Glu Ser Cys Cys Tyr Pro Val Arg Lys Leu Ile Asp Pro Asp Val
                165                 170                 175

Val Tyr Asp Pro Ser Asn Tyr Gly Phe Gly Ser Ile Asn Ile Val Thr
            180                 185                 190

Phe Ser Pro Glu Tyr Glu Tyr Thr Phe Asn Asp Ile Ser Gly Gly His
        195                 200                 205

Asn Ser Ser Thr Glu Ser Phe Ile Ala Asp Pro Ala Ile Ser Leu Ala
    210                 215                 220

His Glu Leu Ile His Ala Leu His Gly Leu Tyr Gly Ala Arg Gly Val
225                 230                 235                 240

Thr Tyr Glu Glu Thr Ile Glu Val Lys Gln Ala Pro Leu Met Ile Ala
                245                 250                 255

Glu Lys Pro Ile Arg Leu Glu Glu Phe Leu Thr Phe Gly Gly Gln Asp
            260                 265                 270

Leu Asn Ile Ile Thr Ser Ala Met Lys Glu Lys Ile Tyr Asn Asn Leu
        275                 280                 285

Leu Ala Asn Tyr Glu Lys Ile Ala Thr Arg Leu Ser Glu Val Asn Ser
    290                 295                 300

Ala Pro Pro Glu Tyr Asp Ile Asn Glu Tyr Lys Asp Tyr Phe Gln Trp
305                 310                 315                 320
```

Lys Tyr Gly Leu Asp Lys Asn Ala Asp Gly Ser Tyr Thr Val Asn Glu
             325                 330                 335

Asn Lys Ser Asn Glu Ile Tyr Lys Lys Leu Tyr Ser Phe Thr Glu Ser
            340                 345                 350

Asp Leu Ala Asn Lys Phe Lys Val Lys Cys Arg Asn Thr Tyr Phe Ile
        355                 360                 365

Lys Tyr Glu Phe Leu Lys Val Pro Asn Leu Leu Asp Asp Ile Tyr
    370                 375                 380

Thr Val Ser Glu Gly Phe Asn Ile Gly Asn Leu Ala Val Asn Arg
385                 390                 395                 400

Gly Gln Ser Ile Lys Leu Asn Pro Lys Ile Ile Asp Ser Pro Asp Lys
            405                 410                 415

Gly Leu Val Glu Lys Ile Val Lys Phe Cys Lys Ser Val Ile Pro Arg
        420                 425                 430

Lys Gly Thr Lys
        435

<210> SEQ ID NO 16
<211> LENGTH: 1317
<212> TYPE: DNA
<213> ORGANISM: Artificial Sequence
<220> FEATURE:
<223> OTHER INFORMATION: Synthetic botulinum neurotoxin light chain of
      serotype G based on wild-type Clostridium
      botulinum sequence

<400> SEQUENCE: 16

```
atgccagtca acatcaagaa cttcaactac aacgacccaa ttaacaacga cgacatcatg      60
atggagccat caacgaccc aggtccaggt acctactaca aggctttcag aatcattgac       120
agaatttgga tcgttccaga gagattcacc tacggtttcc aaccagacca gttcaacgcc      180
tccaccggtg tcttctctaa ggacgtctac gagtactacg acccaaccta cttgaagacc      240
gacgctgaga aggacaagtt cttgaagacc atgatcaagt tgttcaacag aattaactct      300
aagccatccg gtcaaagatt gttggacatg attgttgacg ctattccata cttgggtaac      360
gcctccaccc caccagacaa gttcgctgcc aacgtcgcta cgtttctat caacaagaag       420 attatccaac aggtgctga ggaccagatc aagggtttga tgaccaactt gattattttc       480
ggtccaggtc cagtcttgtc cgacaacttc accgactcta tgatcatgaa cggtcactcc      540
ccaatttccg ggggtttcgg tgctagaatg atgatcagat ctgtccatc ctgtttgaac       600 gttttcaaca acgtccaaga gaacaaggac acctctatct tctctagaag agcttacttc      660
gctgacccag ctctgaccct gatgcacgag ttgatccacg tcttgcacgg tctgtacggt      720
attaagatct ccaacctgcc aattacccca aacaccaagg agttcttcat gcaacactcc      780
gacccagttc aagccgagga gctgtacacc ttcggtggtc acgacccatc tgtttcccca      840
tctaccgaca tgaacattta caacaaggct ctgcagaact ccaagacat gctaacaga       900 ctgaacatcg tctcctctgc caaggttct ggtatcgaca tttccttgta caagcaaatc       960
tacaagaaca agtacgactt cgtcgaggac ccaaacggta gtactctgt tgacaaggac      1020 aagttcgaca gctgtacaa ggctttgatg ttcgtttca ccgagaccaa cttggccggt       1080
gagtacggta ttaagaccag atactcttac ttctctgagt acctgccacc aatcaagacc      1140
gagaagttgt tggacaacac catctacacc cagaacgagg gttttcaacat tgcttccaag      1200 aacttgaaga cgagttcaa cggtcagaac aaggccgtca acaaggaggc ctacgaggag      1260
atttccctgg agcacttggt catctacaga atcgctatgt gtaagccagt catgtac         1317
```

<210> SEQ ID NO 17
<211> LENGTH: 439
<212> TYPE: PRT
<213> ORGANISM: Artificial Sequence
<220> FEATURE:
<223> OTHER INFORMATION: Synthetic botulinum neurotoxin light chain of serotype G based on wild-type Clostridium botulinum sequence

<400> SEQUENCE: 17

```
Met Pro Val Asn Ile Lys Asn Phe Asn Tyr Asn Asp Pro Ile Asn Asn
 1               5                  10                  15

Asp Asp Ile Met Met Glu Pro Phe Asn Asp Pro Gly Pro Gly Thr Tyr
            20                  25                  30

Tyr Lys Ala Phe Arg Ile Ile Asp Arg Ile Trp Ile Val Pro Glu Arg
        35                  40                  45

Phe Thr Tyr Gly Phe Gln Pro Asp Gln Phe Asn Ala Ser Thr Gly Val
    50                  55                  60

Phe Ser Lys Asp Val Tyr Glu Tyr Tyr Asp Pro Thr Tyr Leu Lys Thr
65                  70                  75                  80

Asp Ala Glu Lys Asp Lys Phe Leu Lys Thr Met Ile Lys Leu Phe Asn
                85                  90                  95

Arg Ile Asn Ser Lys Pro Ser Gly Gln Arg Leu Leu Asp Met Ile Val
            100                 105                 110

Asp Ala Ile Pro Tyr Leu Gly Asn Ala Ser Thr Pro Pro Asp Lys Phe
        115                 120                 125

Ala Ala Asn Val Ala Asn Val Ser Ile Asn Lys Lys Ile Ile Gln Pro
    130                 135                 140

Gly Ala Glu Asp Gln Ile Lys Gly Leu Met Thr Asn Leu Ile Ile Phe
145                 150                 155                 160

Gly Pro Gly Pro Val Leu Ser Asp Asn Phe Thr Asp Ser Met Ile Met
                165                 170                 175

Asn Gly His Ser Pro Ile Ser Glu Gly Phe Gly Ala Arg Met Met Ile
            180                 185                 190

Arg Phe Cys Pro Ser Cys Leu Asn Val Phe Asn Asn Val Gln Glu Asn
        195                 200                 205

Lys Asp Thr Ser Ile Phe Ser Arg Arg Ala Tyr Phe Ala Asp Pro Ala
    210                 215                 220

Leu Thr Leu Met His Glu Leu Ile His Val Leu His Gly Leu Tyr Gly
225                 230                 235                 240

Ile Lys Ile Ser Asn Leu Pro Ile Thr Pro Asn Thr Lys Glu Phe Phe
                245                 250                 255

Met Gln His Ser Asp Pro Val Gln Ala Glu Glu Leu Tyr Thr Phe Gly
            260                 265                 270

Gly His Asp Pro Ser Val Ser Pro Ser Thr Asp Met Asn Ile Tyr Asn
        275                 280                 285

Lys Ala Leu Gln Asn Phe Gln Asp Ile Ala Asn Arg Leu Asn Ile Val
    290                 295                 300

Ser Ser Ala Gln Gly Ser Gly Ile Asp Ile Ser Leu Tyr Lys Gln Ile
305                 310                 315                 320

Tyr Lys Asn Lys Tyr Asp Phe Val Glu Asp Pro Asn Gly Lys Tyr Ser
                325                 330                 335

Val Asp Lys Asp Lys Phe Asp Lys Leu Tyr Lys Ala Leu Met Phe Gly
            340                 345                 350

Phe Thr Glu Thr Asn Leu Ala Gly Glu Tyr Gly Ile Lys Thr Arg Tyr
```

```
                355               360                365
Ser Tyr Phe Ser Glu Tyr Leu Pro Pro Ile Lys Thr Glu Lys Leu Leu
    370                375                380

Asp Asn Thr Ile Tyr Thr Gln Asn Glu Gly Phe Asn Ile Ala Ser Lys
385                390                395                400

Asn Leu Lys Asn Glu Phe Asn Gly Gln Asn Lys Ala Val Asn Lys Glu
                405                410                415

Ala Tyr Glu Glu Ile Ser Leu Glu His Leu Val Ile Tyr Arg Ile Ala
            420                425                430

Met Cys Lys Pro Val Met Tyr
        435

<210> SEQ ID NO 18
<211> LENGTH: 1239
<212> TYPE: DNA
<213> ORGANISM: Artificial Sequence
<220> FEATURE:
<223> OTHER INFORMATION: Synthetic N-terminal region of the heavy chain
      of botulinum neurotoxin serotype A based on wild-type
      Clostridium botulinum sequence

<400> SEQUENCE: 18
atggctctga acgacctgtg catcaaagtt aacaactggg acctgttctt ctccccgtct   60
gaagacaact tcactaacga cctgaacaaa ggcgaagaaa tcacctccga cactaacatc   120
gaagctgctg aagaaaacat ctctctggac ctgatccagc agtactacct gactttcaac   180
ttcgacaaca aaccggaaaa catctccatc gaaaacctgt cttccgacat catcggtcag   240
ctggaactga tgccgaacat cgaacgcttc ccgaacggca gaaatacga actggacaaa   300 tacaccatgt tccactacct gcgtgctcag gaattcgaac acggtaaatc tcgtatcgct   360
ctgactaact ccgttaacga agctctgctg aacccgtctc gcgtttacac cttcttctct   420
tccgactacg ttaagaaagt taacaaagct actgaagctg ctatgttcct gggttggggt   480
gaacagctgg tttacgactt caccgacgaa acttctgaag tttccaccac tgacaaaatc   540
gctgacatca ctatcatcat cccgtacatc ggcccggctc tgaacatcgg taacatgctg   600
tacaaagacg acttcgttgg tgctctgatc ttctctggcg ctgttatcct gctggaattc   660
atcccggaaa tcgctatccc ggttctgggt accttcgctc tggttttcta catcgctaac   720
aaagttctga ctgttcagac catcgacaac gctctgtcta acgtaacga aaaatgggac   780 gaagtttaca atacatcgt tactaactgg ctggctaaag ttaacactca gatcgacctg   840
atccgtaaga agatgaaaga agctctggaa accaggctg aagctactaa agctatcatc   900
aactaccagt acaaccagta caccgaagaa gaaaagaaca catcaacttt caacatcgat   960
gacctgtcct ctaaactgaa cgaatccatc aacaaagcta tgatcaacat caacaaattc   1020
ctgaaccagt gctctgtttc ctacctgatg aactctatga tcccgtacgg cgttaaacgc   1080
ctggaagact tcgacgcttc cctgaaagac gctctgctga atacatccg tgacaactac   1140 ggtactctga tcggccaggt tgaccgtctg aaagacaagg ttaacaacac cctgtctact   1200 gacatccgt ccagctgtc caaatacgtt gacaaccag   1239

<210> SEQ ID NO 19
<211> LENGTH: 413
<212> TYPE: PRT
<213> ORGANISM: Artificial Sequence
<220> FEATURE:
<223> OTHER INFORMATION: Synthetic N-terminal region of the heavy chain
      of botulinum neurotoxin serotype A based on wild-type
      Clostridium botulinum sequence
```

<400> SEQUENCE: 19

```
Met Ala Leu Asn Asp Leu Cys Ile Lys Val Asn Asn Trp Asp Leu Phe
  1               5                  10                  15
Phe Ser Pro Ser Glu Asp Asn Phe Thr Asn Asp Leu Asn Lys Gly Glu
             20                  25                  30
Glu Ile Thr Ser Asp Thr Asn Ile Glu Ala Ala Glu Glu Asn Ile Ser
             35                  40                  45
Leu Asp Leu Ile Gln Gln Tyr Tyr Leu Thr Phe Asn Phe Asp Asn Glu
 50                  55                  60
Pro Glu Asn Ile Ser Ile Glu Asn Leu Ser Ser Asp Ile Ile Gly Gln
 65                  70                  75                  80
Leu Glu Leu Met Pro Asn Ile Glu Arg Phe Pro Asn Gly Lys Lys Tyr
                 85                  90                  95
Glu Leu Asp Lys Tyr Thr Met Phe His Tyr Leu Arg Ala Gln Glu Phe
            100                 105                 110
Glu His Gly Lys Ser Arg Ile Ala Leu Thr Asn Ser Val Asn Glu Ala
            115                 120                 125
Leu Leu Asn Pro Ser Arg Val Tyr Thr Phe Phe Ser Ser Asp Tyr Val
130                 135                 140
Lys Lys Val Asn Lys Ala Thr Glu Ala Ala Met Phe Leu Gly Trp Val
145                 150                 155                 160
Glu Gln Leu Val Tyr Asp Phe Thr Asp Glu Thr Ser Glu Val Ser Thr
                165                 170                 175
Thr Asp Lys Ile Ala Asp Ile Thr Ile Ile Pro Tyr Ile Gly Pro
                180                 185                 190
Ala Leu Asn Ile Gly Asn Met Leu Tyr Lys Asp Asp Phe Val Gly Ala
                195                 200                 205
Leu Ile Phe Ser Gly Ala Val Ile Leu Leu Glu Phe Ile Pro Glu Ile
210                 215                 220
Ala Ile Pro Val Leu Gly Thr Phe Ala Leu Val Ser Tyr Ile Ala Asn
225                 230                 235                 240
Lys Val Leu Thr Val Gln Thr Ile Asp Asn Ala Leu Ser Lys Arg Asn
                245                 250                 255
Glu Lys Trp Asp Glu Val Tyr Lys Tyr Ile Val Thr Asn Trp Leu Ala
                260                 265                 270
Lys Val Asn Thr Gln Ile Asp Leu Ile Arg Lys Lys Met Lys Glu Ala
            275                 280                 285
Leu Glu Asn Gln Ala Glu Ala Thr Lys Ala Ile Ile Asn Tyr Gln Tyr
            290                 295                 300
Asn Gln Tyr Thr Glu Glu Glu Lys Asn Asn Ile Asn Phe Asn Ile Asp
305                 310                 315                 320
Asp Leu Ser Ser Lys Leu Asn Glu Ser Ile Asn Lys Ala Met Ile Asn
                325                 330                 335
Ile Asn Lys Phe Leu Asn Gln Cys Ser Val Ser Tyr Leu Met Asn Ser
                340                 345                 350
Met Ile Pro Tyr Gly Val Lys Arg Leu Glu Asp Phe Asp Ala Ser Leu
            355                 360                 365
Lys Asp Ala Leu Leu Lys Tyr Ile Arg Asp Asn Tyr Gly Thr Leu Ile
370                 375                 380
Gly Gln Val Asp Arg Leu Lys Asp Lys Val Asn Asn Thr Leu Ser Thr
385                 390                 395                 400
Asp Ile Pro Phe Gln Leu Ser Lys Tyr Val Asp Asn Gln
                405                 410
```

-continued

<210> SEQ ID NO 20
<211> LENGTH: 2583
<212> TYPE: DNA
<213> ORGANISM: Artificial Sequence
<220> FEATURE:
<223> OTHER INFORMATION: Synthetic polynucleotide sequence for the
      light chain with Hn of C. botulinum Type A.

<400> SEQUENCE: 20

| | | | | |
|---|---|---|---|---|
| atggttcagt tcgttaacaa acagttcaac tacaaagacc cggttaacgg tgttgacatc | 60 |
| gcttacatca aaatcccgaa cgttggtcag atgcagccgg ttaaagcatt caaaatccac | 120 |
| aacaaaatct gggttatccc ggaacgtgac actttcacta cccggaagaa aggtgacctg | 180 |
| aacccgccgc cggaagctaa acaggttccg gtttcttact acgactctac ttacctgtct | 240 |
| actgacaacg aaaaggacaa ctacctgaaa ggtgttacta aactgtttga acgtatctac | 300 |
| tctactgacc tggtcgcat gctgctcact tctatcgttc gtggtatccc gttctggggt | 360 |
| ggttctacta tcgacactga actgaaagtt atcgacacta actgcatcaa cgttatccag | 420 |
| ccggacggtt cttaccgttc tgaagaactg aacctggtta tcatcggtcc gtctgctgac | 480 |
| atcatccagt ttgaatgcaa atctttcggt cacgaagttc tgaacctgac tcgtaacggt | 540 |
| tacggttcta ctcagtacat ccgtttctct ccggacttca ctttcggttt cgaagaatct | 600 |
| ctggaagttg acactaaccc gctgctgggt gctggtaaat cgctactga cccggctgtt | 660 |
| actctggctc acgaactgat ccacgctggt caccgtctgt acggtatcgc tatcaacccg | 720 |
| aaccgtgttt tcaaagttaa cactaacgct tactacgaaa tgtctggtct ggaagtttct | 780 |
| tttgaagaac tgcgtacttt cggtggtcac gacgctaaat tcatcgactc tctgcaggaa | 840 |
| aacgagttcc gtctgtacta ctactacaaa ttcaaagaca tcgcttctac tctgaacaaa | 900 |
| gctaaatcta tcgttggtac cactgcttct ctgcagtaca tgaagaacgt tttcaaagaa | 960 |
| aagtacctgc tgtctgaaga cacttctggt aaattctctg ttgacaaact gaaattcgac | 1020 |
| aaactgtaca aaatgctgac tgaaatctac actgaagaca cttcgttaa attcttcaaa | 1080 |
| gttctgaacc gtaaaactta cctgaacttc gacaaagctg ttttcaaaat caacatcgtt | 1140 |
| ccgaaagtta actacactat ctacgacggt ttcaacctgc gtaacactaa cctggctgct | 1200 |
| aacttcaacg gtcagaacac tgaaatcaac aacatgaact tcactaaact gaagaacttc | 1260 |
| actggtctgt ttgagttcta caaactgctg tgcgttcgtg gtatcatcac ttctaaaact | 1320 |
| aaatctctgg acaaaggtta caacaaagct ctgaacgacc tgtgcatcaa agttaacaac | 1380 |
| tgggacctgt tcttctcccc gtctgaagac aacttcacta cgacctgaa caaaggcgaa | 1440 |
| gaaatcacct ccgacactaa catcgaagct gctgaagaaa acatctctct ggacctgatc | 1500 |
| cagcagtact acctgacttt caacttcgac aacgaaccgg aaaacatctc catcgaaaac | 1560 |
| ctgtcttccg acatcatcgg tcagctggaa ctgatgccga catcgaacg cttcccgaac | 1620 |
| ggcaagaaat acgaactgga caaatacacc atgttccact cctgcgtgc tcaggaattc | 1680 |
| gaacacggta atctcgtat cgctctgact aactccgtta cgaagctct gctgaacccg | 1740 |
| tctcgcgttt acaccttctt ctcttccgac tacgttaaga agttaacaa agctactgaa | 1800 |
| gctgctatgt tcctggggttg ggttgaacag ctggtttacg acttcaccga cgaaacttct | 1860 |
| gaagtttcca ccactgacaa aatcgctgac atcactatca tcatcccgta catcggcccg | 1920 |
| gctctgaaca tcgtaacat gctgtacaaa gacgacttcg ttggtgctct gatcttctct | 1980 |
| ggcgctgtta tcctgctgga attcatcccg gaaatcgcta tcccggttct gggtaccttc | 2040 |

```
gctctggttt cctacatcgc taacaaagtt ctgactgttc agaccatcga caacgctctg    2100
tctaaacgta acgaaaaatg ggacgaagtt tacaaataca tcgttactaa ctggctggct    2160
aaagttaaca ctcagatcga cctgatccgt aagaagatga agaagctct ggaaaaccag     2220 gctgaagcta ctaaagctat catcaactac cagtacaacc agtacaccga agaagaaaag    2280
aacaacatca acttcaacat cgatgacctg tcctctaaac tgaacgaatc catcaacaaa    2340
gctatgatca acatcaacaa attcctgaac cagtgctctg tttcctacct gatgaactct    2400
atgatcccgt acggcgttaa acgcctggaa gacttcgacg cttccctgaa agacgctctg    2460
ctgaaataca tccgtgacaa ctacggtact ctgatcggcc aggttgaccg tctgaaagac    2520
aaggttaaca acaccctgtc tactgacatc ccgttccagc tgtccaaata cgttgacaac    2580
cag                                                                  2583
```

<210> SEQ ID NO 21
<211> LENGTH: 861
<212> TYPE: PRT
<213> ORGANISM: Artificial Sequence
<220> FEATURE:
<223> OTHER INFORMATION: Recombinant protein encoded by SEQ ID NO:20

<400> SEQUENCE: 21

```
Met Val Gln Phe Val Asn Lys Gln Phe Asn Tyr Lys Asp Pro Val Asn
  1               5                  10                  15

Gly Val Asp Ile Ala Tyr Ile Lys Ile Pro Asn Val Gly Gln Met Gln
             20                  25                  30

Pro Val Lys Ala Phe Lys Ile His Asn Lys Ile Trp Val Ile Pro Glu
         35                  40                  45

Arg Asp Thr Phe Thr Asn Pro Glu Glu Gly Asp Leu Asn Pro Pro
     50                  55                  60

Glu Ala Lys Gln Val Pro Val Ser Tyr Tyr Asp Ser Thr Tyr Leu Ser
 65                  70                  75                  80

Thr Asp Asn Glu Lys Asp Asn Tyr Leu Lys Gly Val Thr Lys Leu Phe
                 85                  90                  95

Glu Arg Ile Tyr Ser Thr Asp Leu Gly Arg Met Leu Leu Thr Ser Ile
            100                 105                 110

Val Arg Gly Ile Pro Phe Trp Gly Gly Ser Thr Ile Asp Thr Glu Leu
        115                 120                 125

Lys Val Ile Asp Thr Asn Cys Ile Asn Val Ile Gln Pro Asp Gly Ser
    130                 135                 140

Tyr Arg Ser Glu Glu Leu Asn Leu Val Ile Gly Pro Ser Ala Asp
145                 150                 155                 160

Ile Ile Gln Phe Glu Cys Lys Ser Phe Gly His Glu Val Leu Asn Leu
                165                 170                 175

Thr Arg Asn Gly Tyr Gly Ser Thr Gln Tyr Ile Arg Phe Ser Pro Asp
            180                 185                 190

Phe Thr Phe Gly Phe Glu Glu Ser Leu Glu Val Asp Thr Asn Pro Leu
        195                 200                 205

Leu Gly Ala Gly Lys Phe Ala Thr Asp Pro Ala Val Thr Leu Ala His
    210                 215                 220

Glu Leu Ile His Ala Gly His Arg Leu Tyr Gly Ile Ala Ile Asn Pro
225                 230                 235                 240

Asn Arg Val Phe Lys Val Asn Thr Asn Ala Tyr Tyr Glu Met Ser Gly
                245                 250                 255

Leu Glu Val Ser Phe Glu Glu Leu Arg Thr Phe Gly Gly His Asp Ala
            260                 265                 270
```

```
Lys Phe Ile Asp Ser Leu Gln Glu Asn Glu Phe Arg Leu Tyr Tyr Tyr
        275                 280                 285

Tyr Lys Phe Lys Asp Ile Ala Ser Thr Leu Asn Lys Ala Lys Ser Ile
    290                 295                 300

Val Gly Thr Thr Ala Ser Leu Gln Tyr Met Lys Asn Val Phe Lys Glu
305                 310                 315                 320

Lys Tyr Leu Leu Ser Glu Asp Thr Ser Gly Lys Phe Ser Val Asp Lys
                325                 330                 335

Leu Lys Phe Asp Lys Leu Tyr Lys Met Leu Thr Glu Ile Tyr Thr Glu
            340                 345                 350

Asp Asn Phe Val Lys Phe Phe Lys Val Leu Asn Arg Lys Thr Tyr Leu
        355                 360                 365

Asn Phe Asp Lys Ala Val Phe Lys Ile Asn Ile Val Pro Lys Val Asn
    370                 375                 380

Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
                405                 410                 415

Leu Lys Asn Phe Thr Gly Leu Phe Glu Phe Tyr Lys Leu Leu Cys Val
            420                 425                 430

Arg Gly Ile Ile Thr Ser Lys Thr Lys Ser Leu Asp Lys Gly Tyr Asn
        435                 440                 445

Lys Ala Leu Asn Asp Leu Cys Ile Lys Val Asn Asn Trp Asp Leu Phe
    450                 455                 460

Phe Ser Pro Ser Glu Asp Asn Phe Thr Asn Asp Leu Asn Lys Gly Glu
465                 470                 475                 480

Glu Ile Thr Ser Asp Thr Asn Ile Glu Ala Ala Glu Glu Asn Ile Ser
                485                 490                 495

Leu Asp Leu Ile Gln Gln Tyr Tyr Leu Thr Phe Asn Phe Asp Asn Glu
            500                 505                 510

Pro Glu Asn Ile Ser Ile Glu Asn Leu Ser Ser Asp Ile Ile Gly Gln
        515                 520                 525

Leu Glu Leu Met Pro Asn Ile Glu Arg Phe Pro Asn Gly Lys Lys Tyr
    530                 535                 540

Glu Leu Asp Lys Tyr Thr Met Phe His Tyr Leu Arg Ala Gln Glu Phe
545                 550                 555                 560

Glu His Gly Lys Ser Arg Ile Ala Leu Thr Asn Ser Val Asn Glu Ala
                565                 570                 575

Leu Leu Asn Pro Ser Arg Val Tyr Thr Phe Phe Ser Ser Asp Tyr Val
            580                 585                 590

Lys Lys Val Asn Lys Ala Thr Glu Ala Ala Met Phe Leu Gly Trp Val
        595                 600                 605

Glu Gln Leu Val Tyr Asp Phe Thr Asp Glu Thr Ser Glu Val Ser Thr
    610                 615                 620

Thr Asp Lys Ile Ala Asp Ile Thr Ile Ile Ile Pro Tyr Ile Gly Pro
625                 630                 635                 640

Ala Leu Asn Ile Gly Asn Met Leu Tyr Lys Asp Asp Phe Val Gly Ala
                645                 650                 655

Leu Ile Phe Ser Gly Ala Val Ile Leu Leu Glu Phe Ile Pro Glu Ile
            660                 665                 670

Ala Ile Pro Val Leu Gly Thr Phe Ala Leu Val Ser Tyr Ile Ala Asn
        675                 680                 685

Lys Val Leu Thr Val Gln Thr Ile Asp Asn Ala Leu Ser Lys Arg Asn
```

```
                        690                 695                 700
Glu Lys Trp Asp Glu Val Tyr Lys Tyr Ile Val Thr Asn Trp Leu Ala
705                 710                 715                 720

Lys Val Asn Thr Gln Ile Asp Leu Ile Arg Lys Lys Met Lys Glu Ala
                    725                 730                 735

Leu Glu Asn Gln Ala Glu Ala Thr Lys Ala Ile Ile Asn Tyr Gln Tyr
                740                 745                 750

Asn Gln Tyr Thr Glu Glu Lys Asn Asn Ile Asn Phe Asn Ile Asp
            755                 760                 765

Asp Leu Ser Ser Lys Leu Asn Glu Ser Ile Asn Lys Ala Met Ile Asn
        770                 775                 780

Ile Asn Lys Phe Leu Asn Gln Cys Ser Val Ser Tyr Leu Met Asn Ser
785                 790                 795                 800

Met Ile Pro Tyr Gly Val Lys Arg Leu Glu Asp Phe Asp Ala Ser Leu
                    805                 810                 815

Lys Asp Ala Leu Leu Lys Tyr Ile Arg Asp Asn Tyr Gly Thr Leu Ile
                820                 825                 830

Gly Gln Val Asp Arg Leu Lys Asp Lys Val Asn Asn Thr Leu Ser Thr
            835                 840                 845

Asp Ile Pro Phe Gln Leu Ser Lys Tyr Val Asp Asn Gln
        850                 855                 860

<210> SEQ ID NO 22
<211> LENGTH: 1329
<212> TYPE: DNA
<213> ORGANISM: Artificial Sequence
<220> FEATURE:
<223> OTHER INFORMATION: Synthetic polynucleotide sequence for the
      light chain of C. botulinum Type B,
      optimized for expression in E. coli.

<400> SEQUENCE: 22
atgccagtta ccatcaacaa cttcaactac aacgacccaa tcgacaacaa caacatcatt    60
atgatggagc caccattcgc tagaggtacc ggtagatact acaaggcttt caagatcacc   120
gacagaattt ggattattcc agagagatac actttcggtt acaagccaga ggacttcaac   180
aagtcttctg gtattttcaa cagagacgtc tgcgagtact acgacccaga ctacctgaac   240
accaacgaca gaagaacat cttcctgcag accatgatca gctgttcaa cagaatcaag   300 tccaagccat gggtgagaa gctgctggag atgatcatta cggtatccc atacctgggt   360 gacagaagag tcccactgga ggagttcaac accaacatcg cctccgtcac cgtcaacaag   420
ctgatctcca acccgggtga ggtcgagcgt aagaagggca tcttcgccaa cctgatcatc   480
ttcggcccag gtccagtctt gaacgagaac gagactattg acattggcat tcaaaaccac   540
ttcgcctcca gagagggttt cggcggtatc atgcaaatga agttctgtcc agagtacgtc   600
tccgttttca caacgtcca agagaacaag ggtgcctcca tcttcaacag aagaggctac   660
ttctccgacc cagccttgat cttgatgcac gagttgatcc acgtcttgca cggtttgtac   720
ggtatcaagg tcgacgactt gccaattgtc ccaaacgaga gaagttctt catgcagtcc   780 accgacgcca tccaggccga ggagctgtac accttcggtg gtcaggaccc atccatcatt   840
accccatcca ccgacaagtc catctacgac aaggtcttgc agaacttcag aggtatcgtc   900
gatagactga caaggtcttt ggtctgcatc tccgacccaa acatcaacat caacatttac   960
aagaacaagt tcaaggacaa gtacaagttc gtcgaggact ccgagggtaa gtactccatc  1020
gacgtcgagt ccttcgacaa gctgtacaag tccctgatgt tcggtttcac cgagaccaac  1080
```

-continued

```
atcgccgaga actacaagat caagaccaga gcctcctact tctccgactc cctgccacca    1140
gtcaagatca agaacttgtt ggacaacgaa atctacacta ttgaggaggg tttcaacatt    1200
tccgacaagg acatggagaa ggagtacaga ggtcaaaaca aggctattaa caagcaagct    1260
tacgaggaga tttctaagga gcacttggct gtttacaaga ttcaaatgtg taagtctgtt    1320
aagtaatag                                                             1329
```

<210> SEQ ID NO 23
<211> LENGTH: 441
<212> TYPE: PRT
<213> ORGANISM: Artificial Sequence
<220> FEATURE:
<223> OTHER INFORMATION: Recombinant protein encoded by SEQ ID NO:22

<400> SEQUENCE: 23

```
Met Pro Val Thr Ile Asn Asn Phe Asn Tyr Asn Asp Pro Ile Asp Asn
 1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320
```

```
Lys Asn Lys Phe Lys Asp Lys Tyr Lys Phe Val Glu Asp Ser Glu Gly
            325                 330                 335
Lys Tyr Ser Ile Asp Val Glu Ser Phe Asp Lys Leu Tyr Lys Ser Leu
            340                 345                 350
Met Phe Gly Phe Thr Glu Thr Asn Ile Ala Glu Asn Tyr Lys Ile Lys
            355                 360                 365
Thr Arg Ala Ser Tyr Phe Ser Asp Ser Leu Pro Pro Val Lys Ile Lys
            370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
            420                 425                 430
Lys Ile Gln Met Cys Lys Ser Val Lys
            435                 440

<210> SEQ ID NO 24
<211> LENGTH: 2559
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type B, optimized for expression
      in E. coli.

<400> SEQUENCE: 24
atgccagtta ccatcaacaa cttcaactac aacgacccaa tcgacaacaa caacatcatt      60
atgatggagc caccattcgc tagaggtacc ggtagatact acaaggcttt caagatcacc     120
gacagaattt ggattattcc agagagatac actttcggtt acaagccaga ggacttcaac     180
aagtcttctg gtattttcaa cagagacgtc tgcgagtact acgacccaga ctacctgaac     240
accaacgaca gaagaaacat cttcctgcag accatgatca gctgttcaa cagaatcaag      300 tccaagccat gggtgagaa gctgctggag atgatcatta cggtatccc ataccctgggt      360 gacagaagag tcccactgga ggagttcaac accaacatcg cctccgtcac cgtcaacaag     420
ctgatctcca cccgggtga ggtcgagcgt aagaagggca tcttcgccaa cctgatcatc      480
ttcggcccag gtccagtctt gaacgagaac gagactattg acattggcat tcaaaaccac     540
ttcgcctcca gagagggttt cggcggtatc atgcaaatga agttctgtcc agagtacgtc     600
tccgttttca caacgtcca agagaacaag ggtgcctcca tcttcaacag aagaggctac      660
ttctccgacc cagccttgat cttgatgcac gagttgatcc acgtcttgca cggttttgtac     720 ggtatcaagg tcgacgactt gccaattgtc ccaaacgaga gaagttctt catgcagtcc      780 accgacgcca tccaggccga ggagctgtac accttcggtg gtcaggaccc atccatcatt     840
accccatcca ccgacaagtc catctacgac aaggtcttgc agaacttcag aggtatcgtc      900
gatagactga caaggtcttg gtctgcatc tccgacccaa acatcaacat caacatttac     960
aagaacaagt tcaaggacaa gtacaagttc gtcgaggact ccgagggtaa gtactccatc     1020
gacgtcgagt ccttcgacaa gctgtacaag tccctgatgt tcggtttcac cgagaccaac     1080
atcgccgaga actacaagat caagaccaga gcctcctact ctccgactc cctgccacca     1140 gtcaagatca gaacttgtt ggacaacgaa atctacacta tgaggaggg tttcaacatt      1200 tccgacaagg acatggagaa ggagtacaga ggtcaaaaca aggctattaa caagcaagct     1260
tacgaggaga tttctaagga gcacttggct gtttacaaga ttcaaatgtg taagtctgtt     1320
```

```
aaggctccag gaatctgtat cgacgtcgac aacgaggact tgttcttcat cgctgacaag    1380
aactccttct ccgacgactt gtccaagaac gagagaatcg agtacaacac ccagtccaac    1440
tacatcgaga acgacttccc aatcaacgag ttgatcttgg acaccgactt gatctccaag    1500
atcgagttgc catccgagaa caccgagtcc ttgactgact caacgtcga cgtcccagtc    1560 tacgagaagc aaccagctat caagaagatt tcaccgacg agaacaccat cttccaatac    1620
ctgtactctc agaccttccc tttggacatc agagacatct ccttgacctc ttccttcgac    1680
gacgccctgc tgttctccaa caaggtctac tccttcttct ccatggacta catcaagact    1740
gctaacaagg tcgtcgaggc cggttttgttc gctggttggg tcaagcagat cgtcaacgat    1800
ttcgtcatcg aggctaacaa gtccaacacc atggacaaga ttgccgacat ctccttgatt    1860
gtcccataca tcggtttggc cttgaacgtc ggtaacgaga ccgccaaggg taacttcgag    1920
aacgctttcg agatcgctgg tgcctccatc ttgttggagt tcatcccaga gttgttgatc    1980
ccagtcgtcg gtgccttctt gttggagtcc tacatcgaca acaagaacaa gatcatcaag    2040
accatcgaca acgctttgac caagagaaac gagaagtggt ccgacatgta cggtttgatc    2100
gtcgcccaat ggttgtccac cgtcaacacc caattctaca ccatcaagga gggtatgtac    2160
aaggccttga actaccaggc ccaagctttg gaggagatca tcaagtacag atacaacatc    2220
tactccgaga aggagaagtc caacattaac atcgacttca cgacatcaa ctccaagctg    2280 aacgagggta ttaaccaggc catcgacaac atcaacaact tcatcaacgg ttgttccgtc    2340
tcctacttga tgaagaagat gattccattg gccgtcgaga gttgttgga cttcgacaac    2400 accctgaaga gaacttgtt gaactacatc gacgagaaca agttgtactt gatcggttcc    2460
gctgagtacg agaagtccaa ggtcaacaag tacttgaaga ccatcatgcc attcgacttg    2520
tccatctaca ccaacgacac catcttgatc gagatgttc                           2559
```

<210> SEQ ID NO 25  
<211> LENGTH: 852  
<212> TYPE: PRT  
<213> ORGANISM: Artificial Sequence  
<220> FEATURE:  
<223> OTHER INFORMATION: Recombinant protein encoded by SEQ ID NO:24

<400> SEQUENCE: 25

```
Pro Val Thr Ile Asn Phe Asn Tyr Asn Asp Pro Ile Asp Asn Asn
 1               5                  10                  15

Asn Ile Ile Met Met Glu Pro Pro Phe Ala Arg Gly Thr Gly Arg Tyr
            20                  25                  30

Tyr Lys Ala Phe Lys Ile Thr Asp Arg Ile Trp Ile Ile Pro Glu Arg
        35                  40                  45

Tyr Thr Phe Gly Tyr Lys Pro Glu Asp Phe Asn Lys Ser Ser Gly Ile
    50                  55                  60

Phe Asn Arg Asp Val Cys Glu Tyr Tyr Asp Pro Asp Tyr Leu Asn Thr
65                  70                  75                  80

Asn Asp Lys Lys Asn Ile Phe Leu Gln Thr Met Ile Lys Leu Phe Asn
                85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
    130                 135                 140
```

```
Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190

Lys Phe Cys Pro Glu Tyr Val Ser Val Phe Asn Asn Val Gln Glu Asn
        195                 200                 205

Lys Gly Ala Ser Ile Phe Asn Arg Arg Gly Tyr Phe Ser Asp Pro Ala
    210                 215                 220

Leu Ile Leu Met His Glu Leu Ile His Val Leu His Gly Leu Tyr Gly
225                 230                 235                 240

Ile Lys Val Asp Asp Leu Pro Ile Val Pro Asn Glu Lys Lys Phe Phe
                245                 250                 255

Met Gln Ser Thr Asp Ala Ile Gln Ala Glu Glu Leu Tyr Thr Phe Gly
            260                 265                 270

Gly Gln Asp Pro Ser Ile Ile Thr Pro Ser Thr Asp Lys Ser Ile Tyr
        275                 280                 285

Asp Lys Val Leu Gln Asn Phe Arg Gly Ile Val Asp Arg Leu Asn Lys
    290                 295                 300

Val Leu Val Cys Ile Ser Asp Pro Asn Ile Asn Ile Asn Ile Tyr Lys
305                 310                 315                 320

Asn Lys Phe Lys Asp Lys Tyr Lys Phe Val Glu Asp Ser Glu Gly Lys
                325                 330                 335

Tyr Ser Ile Asp Val Glu Ser Phe Asp Lys Leu Tyr Lys Ser Leu Met
            340                 345                 350

Phe Gly Phe Thr Glu Thr Asn Ile Ala Glu Asn Tyr Lys Ile Lys Thr
        355                 360                 365

Arg Ala Ser Tyr Phe Ser Asp Ser Leu Pro Pro Val Lys Ile Lys Asn
    370                 375                 380

Leu Leu Asp Asn Glu Ile Tyr Thr Ile Glu Glu Gly Phe Asn Ile Ser
385                 390                 395                 400

Asp Lys Asp Met Glu Lys Glu Tyr Arg Gly Gln Asn Lys Ala Ile Asn
                405                 410                 415

Lys Gln Ala Tyr Glu Glu Ile Ser Lys Glu His Leu Ala Val Tyr Lys
            420                 425                 430

Ile Gln Met Cys Lys Ser Val Lys Ala Pro Gly Ile Cys Ile Asp Val
        435                 440                 445

Asp Asn Glu Asp Leu Phe Phe Ile Ala Asp Lys Asn Ser Phe Ser Asp
    450                 455                 460

Asp Leu Ser Lys Asn Glu Arg Ile Glu Tyr Asn Thr Gln Ser Asn Tyr
465                 470                 475                 480

Ile Glu Asn Asp Phe Pro Ile Asn Glu Leu Ile Leu Asp Thr Asp Leu
                485                 490                 495

Ile Ser Lys Ile Glu Leu Pro Ser Glu Asn Thr Glu Ser Leu Thr Asp
            500                 505                 510

Phe Asn Val Asp Val Pro Val Tyr Glu Lys Gln Pro Ala Ile Lys Lys
        515                 520                 525

Ile Phe Thr Asp Glu Asn Thr Ile Phe Gln Tyr Leu Tyr Ser Gln Thr
    530                 535                 540

Phe Pro Leu Asp Ile Arg Asp Ile Ser Leu Thr Ser Ser Phe Asp Asp
545                 550                 555                 560

Ala Leu Leu Phe Ser Asn Lys Val Tyr Ser Phe Phe Ser Met Asp Tyr
                565                 570                 575
```

```
Ile Lys Thr Ala Asn Lys Val Val Glu Ala Gly Leu Phe Ala Gly Trp
            580                 585                 590
Val Lys Gln Ile Val Asn Asp Phe Val Ile Glu Ala Asn Lys Ser Asn
        595                 600                 605
Thr Met Asp Lys Ile Ala Asp Ile Ser Leu Ile Val Pro Tyr Ile Gly
    610                 615                 620
Leu Ala Leu Asn Val Gly Asn Glu Thr Ala Lys Gly Asn Phe Glu Asn
625                 630                 635                 640
Ala Phe Glu Ile Ala Gly Ala Ser Ile Leu Leu Glu Phe Ile Pro Glu
                645                 650                 655
Leu Leu Ile Pro Val Val Gly Ala Phe Leu Leu Glu Ser Tyr Ile Asp
            660                 665                 670
Asn Lys Asn Lys Ile Ile Lys Thr Ile Asp Asn Ala Leu Thr Lys Arg
        675                 680                 685
Asn Glu Lys Trp Ser Asp Met Tyr Gly Leu Ile Val Ala Gln Trp Leu
    690                 695                 700
Ser Thr Val Asn Thr Gln Phe Tyr Thr Ile Lys Glu Gly Met Tyr Lys
705                 710                 715                 720
Ala Leu Asn Tyr Gln Ala Gln Ala Leu Glu Glu Ile Ile Lys Tyr Arg
                725                 730                 735
Tyr Asn Ile Tyr Ser Glu Lys Glu Lys Ser Asn Ile Asn Ile Asp Phe
            740                 745                 750
Asn Asp Ile Asn Ser Lys Leu Asn Glu Gly Ile Asn Gln Ala Ile Asp
        755                 760                 765
Asn Ile Asn Asn Phe Ile Asn Gly Cys Ser Val Ser Tyr Leu Met Lys
    770                 775                 780
Lys Met Ile Pro Leu Ala Val Glu Lys Leu Leu Asp Phe Asp Asn Thr
785                 790                 795                 800
Leu Lys Lys Asn Leu Leu Asn Tyr Ile Asp Glu Asn Lys Leu Tyr Leu
                805                 810                 815
Ile Gly Ser Ala Glu Tyr Glu Lys Ser Lys Val Asn Lys Tyr Leu Lys
            820                 825                 830
Thr Ile Met Pro Phe Asp Leu Ser Ile Tyr Thr Asn Asp Thr Ile Leu
        835                 840                 845
Ile Glu Met Phe
    850

<210> SEQ ID NO 26
<211> LENGTH: 1311
<212> TYPE: DNA
<213> ORGANISM: Artificial Sequence
<220> FEATURE:
<223> OTHER INFORMATION: Synthetic polynucleotide sequence for the
      light chain of of C. botulinum Type C,
      optimized for expression in E. coli.

<400> SEQUENCE: 26
atgccaatca ccatcaacaa cttcaactac tcagaccctg tcgacaacaa gaacattctg      60
tacctggaca ctcacctgaa caccctagct aacgagcctg agaaggcctt cggatcacc     120 ggaaacatct gggtcatccc tgatcgtttc tcccgtaact ccaaccccaa cctgaacaag    180
cctcctcggg tcaccagccc taagagtggt actacgacc ctaactacct gagtaccgac     240
tctgacaagg acaccttcct gaaggagatc atcaagctgt caagcgtat caactcccgt     300 gagatcggag aggagctcat ctacagactt cgaccgata tccccttccc tggtaacaac    360
aatactccaa tcaacaccct tcgacttcgac gtcgacttca actccgtcga cgtcaagact    420
```

```
cggcagggta caactgggt  taagactggt  agcatcaacc  cttccgtcat  catcactgga    480
cctcgtgaga acatcatcga cccagagact  tccacgttca  agctgactaa  caacaccttc    540
gcggctcaag aaggattcgg tgctctgtca  atcatctcca  tctcacctcg  tttcatgctg    600
acctactcga acgcaaccaa cgacgtcgga  gagggtaggt  tctctaagtc  tgagttctgc    660
atggacccaa tcctgatcct gatgcatgag  ctgaaccatg  caatgcacaa  cctgtacgga    720
atcgctatcc caaacgacca gaccatctcc  tccgtgacct  ccaacatctt  ctactcccag    780
tacaacgtga agctggagta cgcagagatc  tacgctttcg  gaggtccaac  tatcgacctt    840
atccctaagt ccgctaggaa gtacttcgag  gagaaggctt  tggattacta  cagatccatc    900
gctaagagac tgaacagtat caccaccgca  aacccttcca  gcttcaacaa  gtacatcggt    960
gagtacaagc agaagctgat cagaaagtac  cgtttcgtcg  tcgagtcttc  aggtgaggtc    1020
acagtaaacc gtaacaagtt cgtcgagctg  tacaacgagc  ttacccagat  cttcacagag    1080
ttcaactacg ctaagatcta caacgtccag  aacaggaaga  tctacctgtc  caacgtgtac    1140
actccggtga cggcgaacat cctggacgac  aacgtctacg  acatccagaa  cggattcaac    1200
atccctaagt ccaacctgaa cgtactattc  atgggtcaaa  acctgtctcg  aaacccagca    1260
ctgcgtaagg tcaaccctga gaacatgctg  tacctgttca  ccaagttctg  c             1311
```

<210> SEQ ID NO 27
<211> LENGTH: 436
<212> TYPE: PRT
<213> ORGANISM: Artificial Sequence
<220> FEATURE:
<223> OTHER INFORMATION: Recombinant protein encoded by SEQ ID NO:26

<400> SEQUENCE: 27

```
Pro Ile Thr Ile Asn Asn Phe Asn Tyr Ser Asp Pro Val Asp Asn Lys
 1               5                  10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205
```

```
Gly Glu Gly Arg Phe Ser Lys Ser Glu Phe Cys Met Asp Pro Ile Leu
            210                 215                 220
Ile Leu Met His Glu Leu Asn His Ala Met His Asn Leu Tyr Gly Ile
225                 230                 235                 240
Ala Ile Pro Asn Asp Gln Thr Ile Ser Ser Val Thr Ser Asn Ile Phe
                245                 250                 255
Tyr Ser Gln Tyr Asn Val Lys Leu Glu Tyr Ala Glu Ile Tyr Ala Phe
            260                 265                 270
Gly Gly Pro Thr Ile Asp Leu Ile Pro Lys Ser Ala Arg Lys Tyr Phe
                275                 280                 285
Glu Glu Lys Ala Leu Asp Tyr Tyr Arg Ser Ile Ala Lys Arg Leu Asn
            290                 295                 300
Ser Ile Thr Thr Ala Asn Pro Ser Ser Phe Asn Lys Tyr Ile Gly Glu
305                 310                 315                 320
Tyr Lys Gln Lys Leu Ile Arg Lys Tyr Arg Phe Val Val Glu Ser Ser
                325                 330                 335
Gly Glu Val Thr Val Asn Arg Asn Lys Phe Val Glu Leu Tyr Asn Glu
            340                 345                 350
Leu Thr Gln Ile Phe Thr Glu Phe Asn Tyr Ala Lys Ile Tyr Asn Val
            355                 360                 365
Gln Asn Arg Lys Ile Tyr Leu Ser Asn Val Tyr Thr Pro Val Thr Ala
370                 375                 380
Asn Ile Leu Asp Asp Asn Val Tyr Asp Ile Gln Asn Gly Phe Asn Ile
385                 390                 395                 400
Pro Lys Ser Asn Leu Asn Val Leu Phe Met Gly Gln Asn Leu Ser Arg
                405                 410                 415
Asn Pro Ala Leu Arg Lys Val Asn Pro Glu Asn Met Leu Tyr Leu Phe
            420                 425                 430
Thr Lys Phe Cys
        435

<210> SEQ ID NO 28
<211> LENGTH: 2436
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type C, optimized for expression
      in E. coli.

<400> SEQUENCE: 28
atgccaatca ccatcaacaa cttcaactac tcagaccctg tcgacaacaa gaacattctg      60
tacctggaca ctcacctgaa caccctagct aacgagcctg agaaggcctt tcggatcacc     120
ggaaacatct gggtcatccc tgatcgtttc tcccgtaact ccaaccccaa cctgaacaag     180
cctcctcggg tcaccagccc taagagtggt actacgacc taactacct gagtaccgac      240 tctgacaagg acaccttcct gaaggagatc atcaagctgt tcaagcgtat caactcccgt     300
gagatcggag aggagctcat ctacagactt cgaccgata tcccttccc tggtaacaac      360 aatactccaa tcaacaccct tcgacttcgac gtcgacttca actccgtcga cgtcaagact    420
cggcagggta caactgggt taagactggt agcatcaacc cttccgtcat catcactgga     480
cctcgtgaga acatcatcga cccagagact tccacgttca gctgactaa caacaccttc    540 gcggctcaag aaggattcgg tgctctgtca atcatctcca tctcacctcg tttcatgctg     600
acctactcga acgcaaccaa cgacgtcgga gagggtaggt tctctaagtc tgagttctgc    660
```

```
atggacccaa tcctgatcct gatgcatgag ctgaaccatg caatgcacaa cctgtacgga    720
atcgctatcc caaacgacca gaccatctcc tccgtgacct ccaacatctt ctactcccag    780
tacaacgtga agctggagta cgcagagatc tacgctttcg aggtccaac tatcgacctt     840 atccctaagt ccgctaggaa gtacttcgag gagaaggctt tggattacta cagatccatc    900
gctaagagac tgaacagtat caccaccgca aacccttcca gcttcaacaa gtacatcggt    960
gagtacaagc agaagctgat cagaaagtac cgtttcgtcg tcgagtcttc aggtgaggtc   1020
acagtaaacc gtaacaagtt cgtcgagctg tacaacgagc ttacccagat cttcacagag   1080
ttcaactacg ctaagatcta caacgtccag aacaggaaga tctacctgtc caacgtgtac   1140
actccggtga cggcgaacat cctggacgac aacgtctacg acatccagaa cggattcaac   1200
atccctaagt ccaacctgaa cgtactattc atgggtcaaa acctgtctcg aaacccagca   1260
ctgcgtaagg tcaaccctga acatgctg tacctgttca ccaagttctg ctccctgtac      1320
aacaagaccc ttgactgtag agagctgctg gtgaagaaca ctgacctgcc attcatcggt   1380
gacatcagtg acgtgaagac tgacatcttc ctgcgtaagg acatcaacga ggagactgag   1440
gtgatctact acccagacaa cgtgtcagta gaccaagtga tcctcagtaa gaacacctcc   1500
gagcatggac aactagacct gctctaccct agtatcgaca gtgagagtga gatcctgcca   1560
ggggagaatc aagtcttcta cgacaaccgt acccagaacg tggactacct gaactcctac   1620
tactacctag agtctcagaa gctgagtgac aacgtggagg acttcactttt cacgcgttca   1680 atcgaggagg ctctggacaa cagtgcaaag gtgtacactt acttccctac cctggctaac   1740
aaggtgaatg ccggtgtgca aggtggtctg ttcctgatgt gggcaaacga cgtggttgag   1800
gacttcacta ccaacatcct gcgtaaggac acactggaca agatctcaga tgtgtcagct   1860
atcatcccct acatcggacc cgcactgaac atctccaact ctgtgcgtcg tggaaacttc   1920
actgaggcat tcgcagtcac tggtgtcacc atcctgctgg aggcattccc tgagttcaca   1980
atccctgctc tgggtgcatt cgtgatctac agtaaggtcc aggagcgaaa cgagatcatc   2040
aagaccatcg acaactgtct ggagcagagg atcaagagat ggaaggactc ctacgagtgg   2100
atgatgggaa cgtggttgtc caggatcatc acccagttca caacatctc ctaccagatg    2160 tacgactccc tgaactacca ggcaggtgca atcaaggcta agatcgacct ggagtacaag   2220
aagtactccg aagcgacaa ggagaacatc aagagccagg ttgagaacct gaagaacagt     2280
ctggacgtca agatctcgga ggcaatgaac aacatcaaca agttcatccg agagtgctcc   2340
gtcacctacc tgttcaagaa catgctgcct aaggtcatcg acgagctgaa cgagttcgac   2400
cgaaacacca aggcaaagct gatcaacctg atcgac                             2436
```

<210> SEQ ID NO 29
<211> LENGTH: 811
<212> TYPE: PRT
<213> ORGANISM: Artificial Sequence
<220> FEATURE:
<223> OTHER INFORMATION: Recombinant protein encoded by SEQ ID NO:28

<400> SEQUENCE: 29

```
Pro Ile Thr Ile Asn Asn Phe Asn Tyr Ser Asp Pro Val Asp Asn Lys
1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
```

```
                 50                  55                  60
Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Leu Ile Tyr Arg Leu Ser Thr Asp
            100                 105                 110

Ile Pro Phe Pro Gly Asn Asn Thr Pro Ile Asn Thr Phe Asp Phe
            115                 120                 125

Asp Val Asp Phe Asn Ser Val Asp Val Lys Thr Arg Gln Gly Asn Asn
        130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
            195                 200                 205

Gly Glu Gly Arg Phe Ser Lys Ser Glu Phe Cys Met Asp Pro Ile Leu
        210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
            275                 280                 285

Glu Glu Lys Ala Leu Asp Tyr Tyr Arg Ser Ile Ala Lys Arg Leu Asn
        290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335

Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
            420                 425                 430

Thr Lys Phe Cys Ser Leu Tyr Asn Lys Thr Leu Asp Cys Arg Glu Leu
        435                 440                 445

Leu Val Lys Asn Thr Asp Leu Pro Phe Ile Gly Asp Ile Ser Asp Val
    450                 455                 460

Lys Thr Asp Ile Phe Leu Arg Lys Asp Ile Asn Glu Glu Thr Glu Val
465                 470                 475                 480
```

Ile Tyr Tyr Pro Asp Asn Val Ser Val Asp Gln Val Ile Leu Ser Lys
                485                 490                 495

Asn Thr Ser Glu His Gly Gln Leu Asp Leu Leu Tyr Pro Ser Ile Asp
                500                 505                 510

Ser Glu Ser Glu Ile Leu Pro Gly Glu Asn Gln Val Phe Tyr Asp Asn
            515                 520                 525

Arg Thr Gln Asn Val Asp Tyr Leu Asn Ser Tyr Tyr Leu Glu Ser
            530                 535                 540

Gln Lys Leu Ser Asp Asn Val Glu Asp Phe Thr Phe Thr Arg Ser Ile
545                 550                 555                 560

Glu Glu Ala Leu Asp Asn Ser Ala Lys Val Tyr Thr Tyr Phe Pro Thr
                565                 570                 575

Leu Ala Asn Lys Val Asn Ala Gly Val Gln Gly Gly Leu Phe Leu Met
                580                 585                 590

Trp Ala Asn Asp Val Val Glu Asp Phe Thr Thr Asn Ile Leu Arg Lys
                595                 600                 605

Asp Thr Leu Asp Lys Ile Ser Asp Val Ser Ala Ile Ile Pro Tyr Ile
            610                 615                 620

Gly Pro Ala Leu Asn Ile Ser Asn Ser Val Arg Arg Gly Asn Phe Thr
625                 630                 635                 640

Glu Ala Phe Ala Val Thr Gly Val Thr Ile Leu Leu Glu Ala Phe Pro
                645                 650                 655

Glu Phe Thr Ile Pro Ala Leu Gly Ala Phe Val Ile Tyr Ser Lys Val
                660                 665                 670

Gln Glu Arg Asn Glu Ile Ile Lys Thr Ile Asp Asn Cys Leu Glu Gln
                675                 680                 685

Arg Ile Lys Arg Trp Lys Asp Ser Tyr Glu Trp Met Met Gly Thr Trp
690                 695                 700

Leu Ser Arg Ile Ile Thr Gln Phe Asn Asn Ile Ser Tyr Gln Met Tyr
705                 710                 715                 720

Asp Ser Leu Asn Tyr Gln Ala Gly Ala Ile Lys Ala Lys Ile Asp Leu
                725                 730                 735

Glu Tyr Lys Lys Tyr Ser Gly Ser Asp Lys Glu Asn Ile Lys Ser Gln
                740                 745                 750

Val Glu Asn Leu Lys Asn Ser Leu Asp Val Lys Ile Ser Glu Ala Met
                755                 760                 765

Asn Asn Ile Asn Lys Phe Ile Arg Glu Cys Ser Val Thr Tyr Leu Phe
                770                 775                 780

Lys Asn Met Leu Pro Lys Val Ile Asp Glu Leu Asn Glu Phe Asp Arg
785                 790                 795                 800

Asn Thr Lys Ala Lys Leu Ile Asn Leu Ile Asp
                805                 810

<210> SEQ ID NO 30
<211> LENGTH: 1323
<212> TYPE: DNA
<213> ORGANISM: Artificial Sequence
<220> FEATURE:
<223> OTHER INFORMATION: Synthetic polynucleotide sequence for the
      light chain of of C. botulinum Type D,
      optimized for expression in E. coli.

<400> SEQUENCE: 30
atgacctggc cagtcaagga cttcaactac tccgacccag tcaacgacaa cgacatcttg      60
tacttgagaa tccacaaaaa caagttgatc accaccccag tcaaggcttt catgatcacc     120
cagaacacct gggttatccc agagagattc tcctccgaca ccaacccatc cctgtccaag     180

```
ccaccaagac caacctccaa gtaccagtct tactacgacc catcttactt gtctaccgac    240
gagcaaaagg acaccttctt gaagggtatt atcaagctgt tcaagagaat caacgagaga    300
gacatcggta agaagttgat caactacttg gtcgttggtt ccccattcat gggtgactcc    360 tctacccag aggacaccctt cgacttcacc agacacacca ccaacattgc cgtcgagaag    420
ttcgagaacg gttcctggaa ggtcaccaac atcatcaccc catctgtttt gatcttcggt    480
ccattgccaa acatcttgga ctacaccgcc tccctgacct tgcaaggtca gcaatccaac    540
ccatccttcg agggtttcgg taccctgtct attttgaagg tcgctccaga gttcttgttg    600
accttctccg acgtcacctc caaccaatcc tccgccgtct gggtaagtc catcttctgt     660 atggacccag tcatcgcttt gatgcacgag ttgacccact ccctgcacca gttgtacggt    720
attaacatcc catctgacaa gagaatcaga ccacaggtct ctgagggttt cttctcccaa    780
gacggtccaa acgttcagtt cgaggagttg tacaccttcg gtggtttgga cgtcgagatt    840
atccaaattg agagatccca attgagagag aaggctttgg gtcactacaa ggacatcgcc    900
aagagactga caacatcaa caagaccatt ccatcttcct ggatctccaa cattgacaag     960
tacaagaaga ttttctccga agtacaac ttcgacaagg acaacaccgg taacttcgtc     1020
gttaacatcg acaagttcaa ctctttgtac tccgacttga ccaacgttat gtctgaggtt    1080
gtctactcct cccaatacaa cgtcaagaac agaaccact acttctccag acactacttg      1140
ccagttttcg ctaacatctt ggacgacaac atttacacca tcagagacgg tttcaacttg    1200
accaacaagg gtttcaacat cgagaactcc ggtcaaaaca tcgagagaaa cccagccctg    1260
caaaagctgt cctccgagtc tgtcgtcgac ttgttcacca aggtctgttt gagattgacc    1320
aag                                                                  1323
```

<210> SEQ ID NO 31
<211> LENGTH: 440
<212> TYPE: PRT
<213> ORGANISM: Artificial Sequence
<220> FEATURE:
<223> OTHER INFORMATION: Recombinant protein encoded by SEQ ID NO:30

<400> SEQUENCE: 31

```
Thr Trp Pro Val Lys Asp Phe Asn Tyr Ser Asp Pro Val Asn Asp Asn
 1               5                  10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Thr Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160
```

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Gln Ile Glu Arg Ser Gln Leu Arg
        275                 280                 285

Glu Lys Ala Leu Gly His Tyr Lys Asp Ile Ala Lys Arg Leu Asn Asn
    290                 295                 300

Ile Asn Lys Thr Ile Pro Ser Ser Trp Ile Ser Asn Ile Asp Lys Tyr
305                 310                 315                 320

Lys Lys Ile Phe Ser Glu Lys Tyr Asn Phe Asp Lys Asp Asn Thr Gly
                325                 330                 335

Asn Phe Val Val Asn Ile Asp Lys Phe Asn Ser Leu Tyr Ser Asp Leu
            340                 345                 350

Thr Asn Val Met Ser Glu Val Val Tyr Ser Ser Gln Tyr Asn Val Lys
        355                 360                 365

Asn Arg Thr His Tyr Phe Ser Arg His Tyr Leu Pro Val Phe Ala Asn
    370                 375                 380

Ile Leu Asp Asp Asn Ile Tyr Thr Ile Arg Asp Gly Phe Asn Leu Thr
385                 390                 395                 400

Asn Lys Gly Phe Asn Ile Glu Asn Ser Gly Gln Asn Ile Glu Arg Asn
                405                 410                 415

Pro Ala Leu Gln Lys Leu Ser Ser Glu Ser Val Val Asp Leu Phe Thr
            420                 425                 430

Lys Val Cys Leu Arg Leu Thr Lys
        435                 440

<210> SEQ ID NO 32
<211> LENGTH: 2475
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type D, optimized for expression
      in E. coli.

<400> SEQUENCE: 32
atgacctggc cagtcaagga cttcaactac tccgacccag tcaacgacaa cgacatcttg      60
tacttgagaa tcccacaaaa caagttgatc accaccccag tcaaggcttt catgatcacc     120
cagaacacct gggttatccc agagagattc cctccgacac caacccatcc cctgtccaag     180
ccaccaagac caacctccaa gtaccagtct tactacgacc catcttactt gtctaccgac     240
gagcaaaagg acaccttctt gaagggtatt atcaagctgt tcaagagaat caacgagaga     300
gacatcggta agaagttgat caactacttg gtcgttggtt ccccattcat gggtgactcc     360

-continued

```
tctacccag aggacacctt cgacttcacc agacacacca ccaacattgc cgtcgagaag      420
ttcgagaacg gttcctggaa ggtcaccaac atcatcaccc catctgtttt gatcttcggt     480
ccattgccaa acatcttgga ctacaccgcc tccctgacct tgcaaggtca gcaatccaac     540
ccatccttcg agggtttcgg taccctgtct attttgaagg tcgctccaga gttcttgttg     600
accttctccg acgtcacctc caaccaatcc tccgccgtct tgggtaagtc catcttctgt    660
atggacccag tcatcgcttt gatgcacgag ttgacccact ccctgcacca gttgtacggt    720
attaacatcc catctgacaa gagaatcaga ccacaggtct ctgagggttt cttctcccaa    780
gacggtccaa acgttcagtt cgaggagttg tacaccttcg gtggtttgga cgtcgagatt   840
atccaaattg agagatccca attgagagag aaggctttgg gtcactacaa ggacatcgcc    900
aagagactga acaacatcaa caagaccatt ccatcttcct ggatctccaa cattgacaag    960
tacaagaaga tttctccga gaagtacaac ttcgacaagg acaacaccgg taacttcgtc    1020
gttaacatcg acaagttcaa ctctttgtac tccgacttga ccaacgttat gtctgaggtt    1080
gtctactcct cccaatacaa cgtcaagaac agaacccact acttctccag acactacttg    1140
ccagttttcg ctaacatctt ggacgacaac atttacacca tcagagacgg tttcaacttg    1200
accaacaagg gtttcaacat cgagaactcc ggtcaaaaca tcgagagaaa cccagccctg    1260
caaaagctgt cctccgagtc tgtcgtcgac ttgttcacca aggtctgttt gagattgacc    1320
aagaactccc gtgacgactc cacctgcatc aaggtcaaga caacagact gccatacgtt     1380 gccgacaagg actccatctc caggagatc ttcgagaaca agatcatcac cgacgagacc    1440
aacgttcaaa actactccga caagttctct ttggacgagt ccatcctgga cggtcaggtc   1500
ccaatcaacc cagagatcgt cgacccactg ttgccaaacg tcaacatgga gccattgaac    1560
ttgccaggtg aggagatcgt cttctacgac gacatcacca agtacgtcga ctacttgaac    1620
tcctactact acttggagtc tcaaaagttg tctaacaacg tcgagaacat caccttgacc    1680
acctccgtcg aggaggcctt gggttactct aacaagatct acaccttcct gccatccttg    1740
gctgagaagg ttaacaaggg tgttcaagct ggtttgttcc tgaactgggc caacgaggtc    1800
gtcgaggact caccaccaa catcatgaag aaggacaccc tggacaagat ctccgacgtc     1860
tccgtcatca tcccatacat cggtccagcc ttgaacatcg gtaactccgc cctgagaggt    1920
aacttcaacc aggccttcgc caccgccggt gtcgccttcc tgctggaggg tttcccagag    1980
ttcaccatcc cagccctggg tgtcttcacc ttctactcct ccatccagga gagagagaag    2040
atcatcaaga ccatcgagaa ctgcttggag cagagagtca agagatggaa ggactcctac    2100
cagtggatgg tttccaactg gctgtccaga atcaccaccc aattcaacca catcaactac    2160
cagatgtacg actccctgtc ctaccaggcc gacgccatca aggccaagat cgacctggag    2220
tacaagaagt actccggttc cgacaaggag aacatcaagt cccaggtcga gaacctgaag    2280
aactccttgg acgtcaagat ctccgaggcc atgaacaaca tcaacaagtt catccgtgag    2340
tgttccgtca cctacctgtt caagaacatg ctgccaaagg tcatcgacga gctgaacaag    2400
ttcgacctga gaccaagac cgagctgatc aacctgatcg actcccacaa catcatcctg     2460
gttggtgagg ttgac                                                      2475
```

<210> SEQ ID NO 33
<211> LENGTH: 824
<212> TYPE: PRT
<213> ORGANISM: Artificial Sequence
<220> FEATURE:
<223> OTHER INFORMATION: Recombinant protein encoded by SEQ ID NO:32

<400> SEQUENCE: 33

```
Thr Trp Pro Val Lys Asp Phe Asn Tyr Ser Asp Pro Val Asn Asp Asn
 1               5                  10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Thr Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
 65                 70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Gln Ile Glu Arg Ser Gln Leu Arg
        275                 280                 285

Glu Lys Ala Leu Gly His Tyr Lys Asp Ile Ala Lys Arg Leu Asn Asn
290                 295                 300

Ile Asn Lys Thr Ile Pro Ser Ser Trp Ile Ser Asn Ile Asp Lys Tyr
305                 310                 315                 320

Lys Lys Ile Phe Ser Glu Lys Tyr Asn Phe Asp Lys Asp Asn Thr Gly
                325                 330                 335

Asn Phe Val Val Asn Ile Asp Lys Phe Asn Ser Leu Tyr Ser Asp Leu
            340                 345                 350

Thr Asn Val Met Ser Glu Val Val Tyr Ser Ser Gln Tyr Asn Val Lys
        355                 360                 365

Asn Arg Thr His Tyr Phe Ser Arg His Tyr Leu Pro Val Phe Ala Asn
370                 375                 380

Ile Leu Asp Asp Asn Ile Tyr Thr Ile Arg Asp Gly Phe Asn Leu Thr
385                 390                 395                 400

Asn Lys Gly Phe Asn Ile Glu Asn Ser Gly Gln Asn Ile Glu Arg Asn
                405                 410                 415
```

Pro Ala Leu Gln Lys Leu Ser Ser Glu Ser Val Val Asp Leu Phe Thr
                420                 425                 430

Lys Val Cys Leu Arg Leu Thr Lys Asn Ser Arg Asp Asp Ser Thr Cys
            435                 440                 445

Ile Lys Val Lys Asn Asn Arg Leu Pro Tyr Val Ala Asp Lys Asp Ser
        450                 455                 460

Ile Ser Gln Glu Ile Phe Glu Asn Lys Ile Ile Thr Asp Glu Thr Asn
465                 470                 475                 480

Val Gln Asn Tyr Ser Asp Lys Phe Ser Leu Asp Glu Ser Ile Leu Asp
                485                 490                 495

Gly Gln Val Pro Ile Asn Pro Glu Ile Val Asp Pro Leu Leu Pro Asn
            500                 505                 510

Val Asn Met Glu Pro Leu Asn Leu Pro Gly Glu Glu Ile Val Phe Tyr
        515                 520                 525

Asp Asp Ile Thr Lys Tyr Val Asp Tyr Leu Asn Ser Tyr Tyr Tyr Leu
530                 535                 540

Glu Ser Gln Lys Leu Ser Asn Asn Val Glu Asn Ile Thr Leu Thr Thr
545                 550                 555                 560

Ser Val Glu Glu Ala Leu Gly Tyr Ser Asn Lys Ile Tyr Thr Phe Leu
                565                 570                 575

Pro Ser Leu Ala Glu Lys Val Asn Lys Gly Val Gln Ala Gly Leu Phe
            580                 585                 590

Leu Asn Trp Ala Asn Glu Val Val Glu Asp Phe Thr Thr Asn Ile Met
        595                 600                 605

Lys Lys Asp Thr Leu Asp Lys Ile Ser Asp Val Ser Val Ile Ile Pro
610                 615                 620

Tyr Ile Gly Pro Ala Leu Asn Ile Gly Asn Ser Ala Leu Arg Gly Asn
625                 630                 635                 640

Phe Asn Gln Ala Phe Ala Thr Ala Gly Val Ala Phe Leu Leu Glu Gly
                645                 650                 655

Phe Pro Glu Phe Thr Ile Pro Ala Leu Gly Val Phe Thr Phe Tyr Ser
            660                 665                 670

Ser Ile Gln Glu Arg Glu Lys Ile Ile Lys Thr Ile Glu Asn Cys Leu
        675                 680                 685

Glu Gln Arg Val Lys Arg Trp Lys Asp Ser Tyr Gln Trp Met Val Ser
690                 695                 700

Asn Trp Leu Ser Arg Ile Thr Thr Gln Phe Asn His Ile Asn Tyr Gln
705                 710                 715                 720

Met Tyr Asp Ser Leu Ser Tyr Gln Ala Asp Ala Ile Lys Ala Lys Ile
                725                 730                 735

Asp Leu Glu Tyr Lys Lys Tyr Ser Gly Ser Asp Lys Glu Asn Ile Lys
            740                 745                 750

Ser Gln Val Glu Asn Leu Lys Asn Ser Leu Asp Val Lys Ile Ser Glu
        755                 760                 765

Ala Met Asn Asn Ile Asn Lys Phe Ile Arg Glu Cys Ser Val Thr Tyr
770                 775                 780

Leu Phe Lys Asn Met Leu Pro Lys Val Ile Asp Glu Leu Asn Lys Phe
785                 790                 795                 800

Asp Leu Arg Thr Lys Thr Glu Leu Ile Asn Leu Ile Asp Ser His Asn
                805                 810                 815

Ile Ile Leu Val Gly Glu Val Asp
            820

<210> SEQ ID NO 34

<211> LENGTH: 1283
<212> TYPE: DNA
<213> ORGANISM: Artificial Sequence
<220> FEATURE:
<223> OTHER INFORMATION: Synthetic polynucleotide sequence for the
      light chain of of C. botulinum Type E,
      optimized for expression in E. coli.

<400> SEQUENCE: 34

```
catatgccga aaatcaactc gttcaactac aacgacccgg tgaatgaccg cacaatcctg      60
tacattaagc cgggcggttg ccaggagttc tacaagagct taacattat gaagaacatc     120
tggatcatcc ctgaacgcaa tgtgatcggg acaacgccac aagatttcca ccctccgact    180
tcgctcaaaa acggggactc ctcctactac gacccaaatt acttgcaaag cgatgaggag    240
aaagatcggt tcctgaagat tgtgacaaag atcttcaacc gtattaacaa caatctctcg    300
gggggcatcc tcctggagga attatccaag gcgaacccct tacctgggca cgacaacact    360
ccagacaacc agttccacat tggcgacgcc tccgcggtgg agatcaagtt ctcgaatggc    420
agtcaggaca tccttctccc taatgtcatt attatgggcg ccgagccgga cctttttgaa    480
accaattcca gcaacatctc gctgcgcaac aactacatgc cgagcaatca cggctttggg    540
tcgatcgcga tcgtgacttt ctcgccggag tactcctttc gcttcaacga caactccatg    600
aacgagttca ttcaggaccc ggcgctcacc ctcatgcacg agctgatcca ctcgttacat    660
ggcttgtacg gcgcgaaggg gatcacgacc aagtatacca ttacgcagaa acagaaccca    720
cttatcacga acatccgtgg gacgaacatc gaggagttcc tcacgttcgg ggggaccgac    780
ctgaacatta tcaccagcgc ccagtccaac gacatttaca cgaacctgct ggcagattac    840
aaaaaaattg cctccaagct ctccaaggtc caggtatcga acccgttgct caatccttac    900
aaggacgtct tcgaggctaa gtatgggctg ataaggatg cctcaggaat ctactctgtg    960
aacatcaaca aattcaacga catcttcaag aagctgtaca gcttcaccga gtttgacctc   1020
gccaccaagt tccaggtcaa atgtcggcaa acgtacattg ccagtataa atattttaag   1080
ctgtcgaatc ttctcaacga ctctatctat aacatctccg aggggtacaa tattaacaac   1140
ttaaaagtca acttccgagg gcagaacgca atctcaacc cacggattat tactcctatt   1200
acaggccgcg ggctcgtcaa gaagatcatc cgattttgca aaaacattgt cagcgttaaa   1260
ggcatccgta agtaatagga tcc                                           1283
```

<210> SEQ ID NO 35
<211> LENGTH: 427
<212> TYPE: PRT
<213> ORGANISM: Artificial Sequence
<220> FEATURE:
<223> OTHER INFORMATION: Recombinant protein encoded by SEQ ID NO:34
<220> FEATURE:
<221> NAME/KEY: UNSURE
<222> LOCATION: (424)...(425)
<223> OTHER INFORMATION: Any amino acid at each position
<220> FEATURE:
<221> NAME/KEY: UNSURE
<222> LOCATION: (427)...(427)
<223> OTHER INFORMATION: Any amino acid

<400> SEQUENCE: 35

```
Met Pro Lys Ile Asn Ser Phe Asn Tyr Asn Asp Pro Val Asn Asp Arg
  1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45
```

Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Xaa Xaa Asp Xaa
            420                 425

<210> SEQ ID NO 36
<211> LENGTH: 2415
<212> TYPE: DNA
<213> ORGANISM: Artificial Sequence
<220> FEATURE:
<223> OTHER INFORMATION: Synthetic polynucleotide gene sequence for the light chain with Hn segment of of C.
botulinum Type E, optimized for expression
in E. coli.

<400> SEQUENCE: 36

```
catatgccga aaatcaactc gttcaactac aacgacccgg tgaatgaccg cacaatcctg      60
tacattaagc cgggcggttg ccaggagttc tacaagagct ttaacattat gaagaacatc     120
tggatcatcc ctgaacgcaa tgtgatcggg acaacgccac aagatttcca ccctccgact     180
tcgctcaaaa acggggactc ctcctactac gacccaaatt acttgcaaag cgatgaggag     240
aaagatcggt tcctgaagat tgtgacaaag atcttcaacc gtattaacaa caatctctcg     300
gggggcatcc tcctggagga attatccaag gcgaacccct acctgggcaa cgacaacact     360
ccagacaacc agttccacat tggcgacgcc tccgcggtgg agatcaagtt ctcgaatggc     420
agtcaggaca tccttctccc taatgtcatt attatgggcg ccgagccgga cctttttgaa     480
accaattcca gcaacatctc gctgcgcaac aactacatgc cgagcaatca cggctttggg     540
tcgatcgcga tcgtgacttt ctcgccggag tactcctttc gcttcaacga caactccatg     600
aacgagttca ttcaggaccc ggcgctcacc ctcatgcacg agctgatcca ctcgttacat     660
ggcttgtacg gcgcgaaggg gatcacgacc aagtatacca ttacgcagaa acagaacccca    720
cttatcacga catccgtgg gacgaacatc gaggagttcc tcacgttcgg ggggaccgac     780
ctgaacatta tcaccagcgc ccagtccaac gacatttaca gaacctgct ggcagattac     840
aaaaaaattg cctccaagct ctccaaggtc caggtatcga acccgttgct caatccttac     900
aaggacgtct tcgaggctaa gtatgggctg gataaggatg cctcaggaat ctactctgtg     960
aacatcaaca aattcaacga catcttcaag aagctgtaca gcttcaccga gtttgacctc    1020
gccaccaagt tccaggtcaa atgtcggcaa acgtacattg ccagtataaa atattttaag    1080
ctgtcgaatc ttctcaacga ctctatctat aacatctccg aggggtacaa tattaacaac    1140
ttaaaagtca cttccgagg gcagaacgca atctcaacc cacggattat tactcctatt    1200
acaggccgcg ggctcgtcaa gaagatcatc cgattttgca aaaacattgt cagcgttaaa    1260
ggcatccgta agtccatctg catcgagatc aacaacggtg agctgttctt cgtggcttcc    1320
gagaacagtt acaacgatga caacatcaac actcctaagg agattgacga caccgtcact    1380
tctaacaaca actacgaaaa cgacctggac caggtcatcc taaacttcaa ctccgagtcc    1440
gcccctggtc tgtccgacga aagctgaac ctgaccatcc agaacgacgc ttacatccca    1500
aagtacgact ccaacggtac atccgatatc gagcagcatg acgttaacga gcttaacgtc    1560
ttcttctact agacgctca gaaggtgccc gagggtgaga acaacgtcaa tctcacctct    1620
tcaattgaca cagccttgtt ggagcagcct aagatctaca ccttcttctc ctccgagttc    1680
atcaacaacg tcaacaagcc tgtgcaggcc gcattgttcg taagctggat tcagcaggtg    1740
ttagtagact tcactactga ggctaaccag aagtccactg ttgacaagat cgctgacatc    1800
tccatcgtcg tcccatacat cggtctggct ctgaacatcg caacgaggc acagaagggc    1860
aacttcaagg atgcccttga gttgttgggt gccggtattt tgttggagtt cgaacccgag    1920
ctgctgatcc ctaccatcct ggtcttcacg atcaagtcct tcctgggttc ctccgacaac    1980
aagaacaagg tcattaaggc catcaacaac gccctgaagg agcgtgacga gaagtggaag    2040
gaagtctatt ccttcatcgt ctcgaactgg atgaccaaga tcaacaccca gttcaacaag    2100
cgaaaggagc agatgtacca ggctctgcag aaccaggtca cgccatcaa gaccatcatc    2160
gagtccaagt acaactccta caccctggag gagaagaacg agcttaccaa caagtacgat    2220
```

```
atcaagcaga tcgagaacga gctgaaccag aaggtctcca tcgccatgaa caacatcgac    2280
aggttcctga ccgagtcctc catctcctac ctgatgaagc tcatcaacga ggtcaagatc    2340
aacaagctgc gagagtacga cgagaatgtc aagacgtacc tgctgaacta catcatccag    2400
cacggatcca tcctg                                                     2415
```

```
<210> SEQ ID NO 37
<211> LENGTH: 804
<212> TYPE: PRT
<213> ORGANISM: Artificial Sequence
<220> FEATURE:
<223> OTHER INFORMATION: Recombinant protein encoded by SEQ ID NO:36

<400> SEQUENCE: 37
```

| | | | | | | | | | | | | | | |
|---|---|---|---|---|---|---|---|---|---|---|---|---|---|---|
| Met | Pro | Lys | Ile | Asn | Ser | Phe | Asn | Tyr | Asn | Asp | Pro | Val | Asn | Asp | Arg |
| 1 | | | | 5 | | | | | 10 | | | | | 15 | |
| Thr | Ile | Leu | Tyr | Ile | Lys | Pro | Gly | Gly | Cys | Gln | Glu | Phe | Tyr | Lys | Ser |
| | | | 20 | | | | | 25 | | | | | 30 | | |
| Phe | Asn | Ile | Met | Lys | Asn | Ile | Trp | Ile | Ile | Pro | Glu | Arg | Asn | Val | Ile |
| | | 35 | | | | | 40 | | | | | 45 | | | |
| Gly | Thr | Thr | Pro | Gln | Asp | Phe | His | Pro | Pro | Thr | Ser | Leu | Lys | Asn | Gly |
| | 50 | | | | | 55 | | | | | 60 | | | | |
| Asp | Ser | Ser | Tyr | Tyr | Asp | Pro | Asn | Tyr | Leu | Gln | Ser | Asp | Glu | Glu | Lys |
| 65 | | | | | 70 | | | | | 75 | | | | | 80 |
| Asp | Arg | Phe | Leu | Lys | Ile | Val | Thr | Lys | Ile | Phe | Asn | Arg | Ile | Asn | Asn |
| | | | | 85 | | | | | 90 | | | | | 95 | |
| Asn | Leu | Ser | Gly | Gly | Ile | Leu | Leu | Glu | Glu | Leu | Ser | Lys | Ala | Asn | Pro |
| | | | 100 | | | | | 105 | | | | | 110 | | |
| Tyr | Leu | Gly | Asn | Asp | Asn | Thr | Pro | Asp | Asn | Gln | Phe | His | Ile | Gly | Asp |
| | | 115 | | | | | 120 | | | | | 125 | | | |
| Ala | Ser | Ala | Val | Glu | Ile | Lys | Phe | Ser | Asn | Gly | Ser | Gln | Asp | Ile | Leu |
| | 130 | | | | | 135 | | | | | 140 | | | | |
| Leu | Pro | Asn | Val | Ile | Ile | Met | Gly | Ala | Glu | Pro | Asp | Leu | Phe | Glu | Thr |
| 145 | | | | | 150 | | | | | 155 | | | | | 160 |
| Asn | Ser | Ser | Asn | Ile | Ser | Leu | Arg | Asn | Asn | Tyr | Met | Pro | Ser | Asn | His |
| | | | | 165 | | | | | 170 | | | | | 175 | |
| Gly | Phe | Gly | Ser | Ile | Ala | Ile | Val | Thr | Phe | Ser | Pro | Glu | Tyr | Ser | Phe |
| | | | 180 | | | | | 185 | | | | | 190 | | |
| Arg | Phe | Asn | Asp | Asn | Ser | Met | Asn | Glu | Phe | Ile | Gln | Asp | Pro | Ala | Leu |
| | | 195 | | | | | 200 | | | | | 205 | | | |
| Thr | Leu | Met | His | Glu | Leu | Ile | His | Ser | Leu | His | Gly | Leu | Tyr | Gly | Ala |
| | 210 | | | | | 215 | | | | | 220 | | | | |
| Lys | Gly | Ile | Thr | Thr | Lys | Tyr | Thr | Ile | Thr | Gln | Lys | Gln | Asn | Pro | Leu |
| 225 | | | | | 230 | | | | | 235 | | | | | 240 |
| Ile | Thr | Asn | Ile | Arg | Gly | Thr | Asn | Ile | Glu | Glu | Phe | Leu | Thr | Phe | Gly |
| | | | | 245 | | | | | 250 | | | | | 255 | |
| Gly | Thr | Asp | Leu | Asn | Ile | Ile | Thr | Ser | Ala | Gln | Ser | Asn | Asp | Ile | Tyr |
| | | | 260 | | | | | 265 | | | | | 270 | | |
| Thr | Asn | Leu | Leu | Ala | Asp | Tyr | Lys | Lys | Ile | Ala | Ser | Lys | Leu | Ser | Lys |
| | | 275 | | | | | 280 | | | | | 285 | | | |
| Val | Gln | Val | Ser | Asn | Pro | Leu | Leu | Asn | Pro | Tyr | Lys | Asp | Val | Phe | Glu |
| | 290 | | | | | 295 | | | | | 300 | | | | |
| Ala | Lys | Tyr | Gly | Leu | Asp | Lys | Asp | Ala | Ser | Gly | Ile | Tyr | Ser | Val | Asn |
| 305 | | | | | 310 | | | | | 315 | | | | | 320 |
| Ile | Asn | Lys | Phe | Asn | Asp | Ile | Phe | Lys | Lys | Leu | Tyr | Ser | Phe | Thr | Glu |
| | | | | 325 | | | | | 330 | | | | | 335 | |

```
Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
            405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
            450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
```

```
                    755                 760                 765
Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu

<210> SEQ ID NO 38
<211> LENGTH: 1334
<212> TYPE: DNA
<213> ORGANISM: Artificial Sequence
<220> FEATURE:
<223> OTHER INFORMATION: Synthetic polynucleotide sequence for the
      light chain of of C. botulinum Type F,
      optimized for expression in E. coli.

<400> SEQUENCE: 38
catatgccgg ttgtcatcaa ttcttttaac tacaacgacc cggtgaacga cgacacgatt      60
ctgtacatgc aaatccctta cgaggagaag tctaaaaagt attataaggc gttcgagatc     120
atgcgcaacg tgtggatcat cccggaacgc aacactattg gacagaccc gtcggacttc      180 gatccgcctg cgtcgcttga aaacggctca tcagcatact atgacccaaa ttatttgact     240
acggacgcgg aaaaggaccg ttatctcaag accacaatca agctcttcaa gcgtattaac     300
tccaacccgg cgggcgaggt attgcttcag gagatttcct acgccaagcc ttacctcggc     360
aatgagcata ctcctatcaa cgagttccac cctgtgaccc gaaccacgtc tgtaaacatt     420
aagagttcga cgaatgtaaa gtcgtcaatt attctcaacc tcttggtcct tggcgcgggg     480
ccggacatct tcgagaactc ttcctacccg gttcgcaagc tcatggacag tgggggggtc     540
tatgacccga gcaacgacgg gttcggttcc atcaatatcg tgaccttctc acctgagtac     600
gagtatacat ttaacgacat cagcggcggc tacaacagta gcaccgagtc ctttatcgcc     660
gacccggcca tcagcctcgc tcacgagctc atccacgccc tgcacgggct gtacggggcc     720
cggggcgtta catataagga gaccatcaaa gtgaagcagg cgccactcat gattgccgaa     780
aagccaatcc gattggagga gttcctgaca ttcggggggcc aggacctgaa tattatcact     840
agtgcaatga ggagaagat ttataacaac ctgctcgcga actatgagaa gatcgccact     900
cgcttatccc gggtgaactc cgccccaccg gagtatgaca ttaacgagta taagactac     960 ttccagtgga gtatggact ggataaaaac gcggacgggt cttacaccgt gaacgagaac    1020
aaattcaacg agatctacaa gaagctctac agcttcacgg agatcgacct cgcgaacaag    1080
ttcaaggtga agtgccggaa cacgtatttc atcaagtacg gcttcttaaa ggtgccaaac    1140
ctgttagacg acgacatttta taccgtatcg gagggcttca atattggtaa tctggccgtg    1200
aacaatcgcg gccagaatat taaacttaac ccgaaaatta tcgactcgat cccagacaag    1260
gggttagttg agaagatcgt caagttctgc aagtcggtca tccctcgcaa ggggacgaag    1320
aattaatagg atcc                                                     1334

<210> SEQ ID NO 39
<211> LENGTH: 443
<212> TYPE: PRT
<213> ORGANISM: Artificial Sequence
<220> FEATURE:
<223> OTHER INFORMATION: Recombinant protein encoded by SEQ ID NO:38
<220> FEATURE:
<221> NAME/KEY: UNSURE
<222> LOCATION: (441)...(442)
<223> OTHER INFORMATION: Any amino acid at each position
```

<400> SEQUENCE: 39

```
Met Pro Val Val Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asp Pro Ser Asp Phe Asp Pro Pro Ala Ser
    50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415
```

Pro Asp Lys Gly Leu Val Glu Lys Ile Val Lys Phe Cys Lys Ser Val
            420                 425                 430

Ile Pro Arg Lys Gly Thr Lys Asn Xaa Xaa Asp
            435                 440

<210> SEQ ID NO 40
<211> LENGTH: 2577
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type F, optimized for expression
      in E. coli.

<400> SEQUENCE: 40

```
catatgccgg ttgtcatcaa ttcttttaac tacaacgacc cggtgaacga cgacacgatt      60
ctgtacatgc aaatcccttc cgaggagaag tctaaaaagt attataaggc gttcgagatc     120
atgcgcaacg tgtggatcat cccggaacgc aacactattg gacagaccc gtcggacttc     180
gatccgcctg cgtcgcttga aaacggctca tcagcatact atgacccaaa ttatttgact     240
acggacgcg aaaaggaccg ttatctcaag accacaatca agctcttcaa gcgtattaac     300
tccaacccgg cgggcgaggt attgcttcag gagattcct acgccaagcc ttacctcggc     360
aatgagcata ctcctatcaa cgagttccac cctgtgaccc gaaccacgtc tgtaaacatt     420
aagagttcga cgaatgtaaa gtcgtcaatt attctcaacc tcttggtcct ggcgcgggg     480
ccggacatct tcgagaactc ttcctacccg gttcgcaagc tcatgacag tgggggggtc     540
tatgacccga gcaacgacgg gttcggttcc atcaatatcg tgaccttctc acctgagtac     600
gagtataact taacgacat cagcggcggc tacaacagta gcaccgagtc ctttatcgcc     660
gacccggcca tcagcctcgc tcacgagctc atccacgccc tgcacgggct gtacggggcc     720
cggggcgtta catataagga gaccatcaaa gtgaagcagg cgccactcat gattgccgaa     780
aagccaatcc gattggagga gttcctgaca tcgggggcc aggacctgaa tattatcact     840
agtgcaatga ggagaagat ttataacaac ctgctcgcga actatgagaa gatcgccact     900
cgcttatccc gggtgaactc cgccccaccg gagtatgaca ttaacgagta taagactac     960
ttccagtgga gtatggact ggataaaaac gcggacgggt cttacaccgt gaacgagaac    1020
aaattcaacg agatctacaa gaagctctac agcttcacgg gatcgacct cgcgaacaag    1080
ttcaaggtga agtgccggaa cacgtattc atcaagtacg gcttcttaaa ggtgccaaac    1140
ctgttagacg acgacattta taccgtatcg gagggcttca atattggtaa tctggccgtg    1200
aacaatcgcg gccagaatat taaacttaac ccgaaaatta tcgactcgat cccagacaag    1260
gggttagttg agaagatcgt caagttctgc aagtcggtca tccctcgcaa ggggacgaag    1320
aattgcaagt ccgtcatccc acgtaagggt accaaggccc caccacgtct gtgtattaga    1380
gtcaacaact cagaattatt ctttgtcgct tccgagtcaa gctacaacga aacgatatt    1440
aacacaccta aagagattga cgatactacc aacctaaaca caactaccg gaacaacttg    1500
gatgaggtta ttttggatta caactcacag accatccctc aaatttccaa ccgtaccta    1560
aacactcttg tccaagacaa ctcctacgtt ccaagatacg attctaacgg tacctcagag    1620
atcgaggagt atgatgttgt tgactttaac gtcttttttct atttgcatgc ccagaaggtg    1680
ccagaaggtg aaaccaacat ctcattgact tcttccattg ataccgcctt gttggaagag    1740
tccaaggata tcttcttttc ttcggagttt atcgatacta tcaacaagcc tgtcaacgcc    1800
gctctgttca ttgattggat tagcaaggtc atcagagatt ttaccactga agctactcaa    1860
```

```
aagtccactg ttgataagat tgctgacatc tctttgattg tccccctatgt cggtcttgct  1920 ttgaacatca ttattgaggc agaaaagggt aactttgagg aggcttttga attgttggga  1980
gttggtattt tgttggagtt tgttccagaa cttaccattc ctgtcatttt agttttttacg  2040 atcaagtcct acatcgattc atacgagaac aagaataaag caattaaagc tattaacaac  2100
tccttgatcg aaagagaggc taagtggaag gaaatctact catggattgt atcaaactgg  2160
cttactagaa ttaacactca atttaacaag agaaaggagc aaatgtacca ggctctgcaa  2220
aaccaagtcg atgctatcaa gactgcaatt gaatacaagt acaacaacta tacttccgat  2280
gagaagaaca gacttgaatc tgaatacaat atcaacaaca ttgaagaaga gttgaacaag  2340
aaagtttctt tggctatgaa gaatatcgaa agatttatga ccgaatcctc tatctcttac  2400
ttgatgaagt tgatcaatga ggccaaggtt ggtaagttga agaagtacga taaccacgtt  2460
aagagcgatc tgctgaacta cattctcgac cacagatcaa tcctgggaga gcagacaaac  2520
gagctgagtg atttggttac ttccactttg aactcctcca ttccatttga gctttct    2577
```

<210> SEQ ID NO 41
<211> LENGTH: 858
<212> TYPE: PRT
<213> ORGANISM: Artificial Sequence
<220> FEATURE:
<223> OTHER INFORMATION: Recombinant protein encoded by SEQ ID NO:40

<400> SEQUENCE: 41

```
Met Pro Val Val Ile Asn Ser Phe Asn Tyr Asn Asp Pro Val Asn Asp
  1               5                  10                  15

Asp Thr Ile Leu Tyr Met Gln Ile Pro Tyr Glu Glu Lys Ser Lys Lys
             20                  25                  30

Tyr Tyr Lys Ala Phe Glu Ile Met Arg Asn Val Trp Ile Ile Pro Glu
         35                  40                  45

Arg Asn Thr Ile Gly Thr Asp Pro Ser Asp Phe Asp Pro Pro Ala Ser
     50                  55                  60

Leu Glu Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240
```

```
Gly Val Thr Tyr Lys Glu Thr Ile Lys Val Lys Gln Ala Pro Leu Met
                245                 250                 255

Ile Ala Glu Lys Pro Ile Arg Leu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Arg Val
        290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Asn Cys Lys Ser Val Ile Pro Arg Lys
        435                 440                 445

Gly Thr Lys Ala Pro Pro Arg Leu Cys Ile Arg Val Asn Asn Ser Glu
450                 455                 460

Leu Phe Phe Val Ala Ser Glu Ser Ser Tyr Asn Glu Asn Asp Ile Asn
465                 470                 475                 480

Thr Pro Lys Glu Ile Asp Asp Thr Thr Asn Leu Asn Asn Asn Tyr Arg
                485                 490                 495

Asn Asn Leu Asp Glu Val Ile Leu Asp Tyr Asn Ser Gln Thr Ile Pro
            500                 505                 510

Gln Ile Ser Asn Arg Thr Leu Asn Thr Leu Val Gln Asp Asn Ser Tyr
        515                 520                 525

Val Pro Arg Tyr Asp Ser Asn Gly Thr Ser Glu Ile Glu Glu Tyr Asp
    530                 535                 540

Val Val Asp Phe Asn Val Phe Phe Tyr Leu His Ala Gln Lys Val Pro
545                 550                 555                 560

Glu Gly Glu Thr Asn Ile Ser Leu Thr Ser Ser Ile Asp Thr Ala Leu
                565                 570                 575

Leu Glu Glu Ser Lys Asp Ile Phe Phe Ser Ser Glu Phe Ile Asp Thr
            580                 585                 590

Ile Asn Lys Pro Val Asn Ala Ala Leu Phe Ile Asp Trp Ile Ser Lys
        595                 600                 605

Val Ile Arg Asp Phe Thr Thr Glu Ala Thr Gln Lys Ser Thr Val Asp
    610                 615                 620

Lys Ile Ala Asp Ile Ser Leu Ile Val Pro Tyr Val Gly Leu Ala Leu
625                 630                 635                 640

Asn Ile Ile Ile Glu Ala Glu Lys Gly Asn Phe Glu Glu Ala Phe Glu
                645                 650                 655

Leu Leu Gly Val Gly Ile Leu Leu Glu Phe Val Pro Glu Leu Thr Ile
            660                 665                 670
```

```
Pro Val Ile Leu Val Phe Thr Ile Lys Ser Tyr Ile Asp Ser Tyr Glu
        675                 680                 685

Asn Lys Asn Lys Ala Ile Lys Ala Ile Asn Asn Ser Leu Ile Glu Arg
    690                 695                 700

Glu Ala Lys Trp Lys Glu Ile Tyr Ser Trp Ile Val Ser Asn Trp Leu
705                 710                 715                 720

Thr Arg Ile Asn Thr Gln Phe Asn Lys Arg Lys Glu Gln Met Tyr Gln
                725                 730                 735

Ala Leu Gln Asn Gln Val Asp Ala Ile Lys Thr Ala Ile Glu Tyr Lys
            740                 745                 750

Tyr Asn Asn Tyr Thr Ser Asp Glu Lys Asn Arg Leu Glu Ser Glu Tyr
        755                 760                 765

Asn Ile Asn Asn Ile Glu Glu Leu Asn Lys Lys Val Ser Leu Ala
    770                 775                 780

Met Lys Asn Ile Glu Arg Phe Met Thr Glu Ser Ser Ile Ser Tyr Leu
785                 790                 795                 800

Met Lys Leu Ile Asn Glu Ala Lys Val Gly Lys Leu Lys Lys Tyr Asp
                805                 810                 815

Asn His Val Lys Ser Asp Leu Leu Asn Tyr Ile Leu Asp His Arg Ser
            820                 825                 830

Ile Leu Gly Glu Gln Thr Asn Glu Leu Ser Asp Leu Val Thr Ser Thr
        835                 840                 845

Leu Asn Ser Ser Ile Pro Phe Glu Leu Ser
    850                 855

<210> SEQ ID NO 42
<211> LENGTH: 1337
<212> TYPE: DNA
<213> ORGANISM: Artificial Sequence
<220> FEATURE:
<223> OTHER INFORMATION: Synthetic polynucleotide sequence for the
      light chain of of C. botulinum Type G,
      optimized for expression in E. coli.

<400> SEQUENCE: 42
catatgccgg tcaatattaa gaacttcaat tacaacgacc cgatcaataa tgacgatatc      60
attatgatgg agcctttcaa cgacccaggt ccaggcacgt attacaaggc ttttcggatc     120
atcgaccgca tttggatcgt cccggagcgc ttcacgtacg gcttccaacc tgaccagttc     180
aatgcaagca cagggttttt cagcaaggac gtctacgagt actatgaccc aacttacctg     240
aagactgacg cggagaagga caaattcctg aagacgatga tcaagttgtt caaccgcatt     300
aactccaagc cgtccggcca gcgactgctt gatatgattg tggacgccat ccttacctc     360 ggaaacgcct ctacgccacc ggacaagttc gcggcaaacg ttgcaaacgt gtccatcaac     420
aagaaaatta ttcagccggg ggccgaggac cagattaagg gactatgac taatctgatc     480 atcttcgggc cggggcctgt actctcggac aacttcacgg acagcatgat tatgaacggc     540
cattcaccga tctcagaagg attcggggca cgtatgatga tccggttctg cccgagttgc     600
ctcaacgtct tcaacaacgt tccaggaaaat aaggatacat cgatcttctc ccgccgtgcc     660
tacttcgcgg acccagcgtt aaccctatg cacgagttaa tccacgtatt gcacggcctc     720
tacggcatta agatctcgaa cttacctatt accccaaaca cgaaagagtt cttcatgcaa     780
cacagcgacc cggttcaggc cgaggaatta tacaccttcg gcgggcacga cccaagtgtt     840
atctcaccgt ctaccgatat gaatatctac aacaaggccc tgcaaaactt ccaggacatc     900
gcaaaccggc ttaacattgt ctcatcggca caggggtctg gtatcgacat ctccctgtat     960
```

```
aagcagatct acaagaataa gtacgacttc gtagaagacc cgaacggcaa gtactcggtg    1020
gacaaggaca agtttgacaa actctacaaa gctctcatgt tcggtttcac agagacaaat    1080
cttgccggag agtacgggat caagacgcgg tactcgtatt tttccgagta cctgccgcct    1140
attaagacgg agaagttgct cgataacacc atttacactc agaatgaggg gttcaacatc    1200
gcctctaaga atctcaagac cgagttcaat ggtcagaaca aggcggtgaa caaagaggcg    1260
tatgaggaga ttagtctgga acacttggtg atctaccgaa ttgcgatgtg taagcctgtg    1320
atgtactaat aggatcc                                                   1337
```

<210> SEQ ID NO 43
<211> LENGTH: 444
<212> TYPE: PRT
<213> ORGANISM: Artificial Sequence
<220> FEATURE:
<223> OTHER INFORMATION: Recombinant protein encoded by SEQ ID NO:42
<220> FEATURE:
<221> NAME/KEY: UNSURE
<222> LOCATION: (442)...(443)
<223> OTHER INFORMATION: Any amino acid at each position
<400> SEQUENCE: 43

```
Met Pro Val Asn Ile Lys Asn Phe Asn Tyr Asn Asp Pro Ile Asn Asn
 1               5                  10                  15

Asp Asp Ile Ile Met Met Glu Pro Phe Asn Asp Gly Pro Gly Thr
             20                  25                  30

Tyr Tyr Lys Ala Phe Arg Ile Ile Asp Arg Ile Trp Ile Val Pro Glu
         35                  40                  45

Arg Phe Thr Tyr Gly Phe Gln Pro Asp Gln Phe Asn Ala Ser Thr Gly
     50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                 85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270
```

```
Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
        290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Xaa Xaa Asp
            435                 440

<210> SEQ ID NO 44
<211> LENGTH: 2547
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type G, optimized for expression
      in E. coli.

<400> SEQUENCE: 44
catatgccgg tcaatattaa gaacttcaat tacaacgacc cgatcaataa tgacgatatc     60
attatgatgg agccttttcaa cgacccaggt ccaggcacgt attacaaggc ttttcggatc    120
atcgaccgca tttggatcgt cccggagcgc ttcacgtacg gcttccaacc tgaccagttc    180
aatgcaagca caggggtttt cagcaaggac gtctacgagt actatgaccc aacttacctg    240
aagactgacg cggagaagga caaattcctg aagacgatga tcaagttgtt caaccgcatt    300
aactccaagc cgtccggcca cgactgcttt gatatgattg tggacgccat cccttacctc    360
ggaaacgcct ctacgccacc ggacaagttc gcggcaaacg ttgcaaacgt gtccatcaac    420
aagaaaatta ttcagccggg ggccgaggac cagattaagg gacttatgac taatctgatc    480
atcttcgggc cggggcctgt actctcggac aacttcacgg acagcatgat tatgaacggc    540
cattcaccga tctcagaagg attcggggca cgtatgatga tccggttctg cccgagttgc    600
ctcaacgtct tcaacaacgt ccaggaaaat aaggatacat cgatcttctc ccgccgtgcc    660
tacttcgcgg acccagcgtt aaccctttatg cacgagttaa tccacgtatt gcacggcctc    720
tacggcatta agatctcgaa cttacctatt accccaaaca cgaaagagtt cttcatgcaa    780
cacagcgacc cggttcaggc cgaggaatta tacaccttcg gcgggcacga cccaagtgtt    840
atctcaccgt ctaccgatat gaatatctac aacaaggccc tgcaaaactt ccaggacatc    900
gcaaaccggc ttaacattgt ctcatcggca caggggtctg gtatcgacat ctccctgtat    960
aagcagatct acaagaataa gtacgacttc gtagaagacc cgaacggcaa gtactcggtg   1020
```

```
gacaaggaca agtttgacaa actctacaaa gctctcatgt tcggtttcac agagacaaat    1080
cttgccggag agtacgggat caagacgcgg tactcgtatt tttccgagta cctgccgcct    1140
attaagacgg agaagttgct cgataacacc atttacactc agaatgaggg gttcaacatc    1200
gcctctaaga atctcaagac cgagttcaat ggtcagaaca aggcggtgaa caaagaggcg    1260
tatgaggaga ttagtctgga acacttggtg atctaccgaa ttgcgatgtg taagcctgtg    1320
atgtacaaga acaccggtaa gtccgagcag tgtatcatcg tcaacaacga ggacttgttc    1380
ttcatcgcca acaaggactc cttctccaag gacttggcca aggctgagac catcgcctac    1440
aacacccaga caacaccat cgagaacaac ttctccatcg accagctgat cttggacaac    1500
gacctgtcct ccggtatcga cctgccaaac gagaacaccg agccattcac caacttcgac    1560
gacatcgaca tcccagtcta catcaagcag tccgccctga agaagatctt cgtcgacggt    1620
gactccttgt tcgagtacct gcacgcccag accttcccat ccaacatcga gaaccagttg    1680
accaactccc tgaacgacgc tttgagaaac aacaacaagg tctacacctt cttctccact    1740
aacttggtcg agaaggccaa cactgtcgtc ggtgcctcct tgttcgtcaa ctgggtcaag    1800
ggtgtcatcg acgacttcac ctccgagtcc acccaaaagt ccaccatcga caaggtctcc    1860
gacgtctcca tcatcatccc atacatcggt ccagccctga acgtcggtaa cgagaccgct    1920
aaggagaact tcaagaacgc cttcgagatc ggtggtgccg ccatcctgat ggagttcatc    1980
ccagagttga tcgtcccaat cgtcggtttc ttcaccttgg agtcctacgt cggtaacaag    2040
ggtcacatca tcatgaccat ctccaacgcc ctgaagaaga gagaccagaa gtggaccgac    2100
atgtacggtt tgatcgtctc ccagtggttg tccaccgtca cacccagtt ctacaccatc    2160
aaggagagaa tgtacaacgc cttgaacaac cagtcccagg ccatcgagaa gatcatcgag    2220
gaccagtaca accgttactc cgaggaggac aagatgaaca tcaacatcga cttcaacgac    2280
atcgacttca agctgaacca gtccatcaac ctggccatca caacatcga cgacttcatc    2340
aaccagtgtt ccatctccta cctgatgaac cgtatgatcc cactggccgt caagaagttg    2400
aaggacttcg acgacaacct gaagcgtgac ctgctggagt acatcgacac caacgagttg    2460
tacctgctgg acgaggtcaa catcttgaag tccaaggtca cagacacttt gaaggactcc    2520
atcccattcg acttgtcctt gtacacc                                        2547
```

<210> SEQ ID NO 45
<211> LENGTH: 848
<212> TYPE: PRT
<213> ORGANISM: Artificial Sequence
<220> FEATURE:
<223> OTHER INFORMATION: Recombinant protein encoded by SEQ ID NO:44

<400> SEQUENCE: 45

```
Met Pro Val Asn Ile Lys Asn Phe Asn Tyr Asn Asp Pro Ile Asn Asn
 1               5                  10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95
```

```
Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
            210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
            290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Tyr Gly Ile Lys Thr
            355                 360                 365

Arg Tyr Ser Tyr Phe Ser Glu Tyr Leu Pro Pro Ile Lys Thr Glu Lys
            370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys
            450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
            515                 520                 525
```

-continued

```
Gln Ser Ala Leu Lys Lys Ile Phe Val Asp Gly Asp Ser Leu Phe Glu
    530                 535                 540
Tyr Leu His Ala Gln Thr Phe Pro Ser Asn Ile Glu Asn Gln Leu Thr
545                 550                 555                 560
Asn Ser Leu Asn Asp Ala Leu Arg Asn Asn Lys Val Tyr Thr Phe
                565                 570                 575
Phe Ser Thr Asn Leu Val Glu Lys Ala Asn Thr Val Val Gly Ala Ser
                580                 585                 590
Leu Phe Val Asn Trp Val Lys Gly Val Ile Asp Asp Phe Thr Ser Glu
                595                 600                 605
Ser Thr Gln Lys Ser Thr Ile Asp Lys Val Ser Asp Val Ser Ile Ile
    610                 615                 620
Ile Pro Tyr Ile Gly Pro Ala Leu Asn Val Gly Asn Glu Thr Ala Lys
625                 630                 635                 640
Glu Asn Phe Lys Asn Ala Phe Glu Ile Gly Gly Ala Ala Ile Leu Met
                645                 650                 655
Glu Phe Ile Pro Glu Leu Ile Val Pro Ile Val Gly Phe Phe Thr Leu
                660                 665                 670
Glu Ser Tyr Val Gly Asn Lys Gly His Ile Ile Met Thr Ile Ser Asn
                675                 680                 685
Ala Leu Lys Lys Arg Asp Gln Lys Trp Thr Asp Met Tyr Gly Leu Ile
    690                 695                 700
Val Ser Gln Trp Leu Ser Thr Val Asn Thr Gln Phe Tyr Thr Ile Lys
705                 710                 715                 720
Glu Arg Met Tyr Asn Ala Leu Asn Asn Gln Ser Gln Ala Ile Glu Lys
                725                 730                 735
Ile Ile Glu Asp Gln Tyr Asn Arg Tyr Ser Glu Asp Lys Met Asn
                740                 745                 750
Ile Asn Ile Asp Phe Asn Asp Ile Asp Phe Lys Leu Asn Gln Ser Ile
                755                 760                 765
Asn Leu Ala Ile Asn Asn Ile Asp Asp Phe Ile Asn Gln Cys Ser Ile
    770                 775                 780
Ser Tyr Leu Met Asn Arg Met Ile Pro Leu Ala Val Lys Lys Leu Lys
785                 790                 795                 800
Asp Phe Asp Asp Asn Leu Lys Arg Asp Leu Leu Glu Tyr Ile Asp Thr
                805                 810                 815
Asn Glu Leu Tyr Leu Leu Asp Glu Val Asn Ile Leu Lys Ser Lys Val
                820                 825                 830
Asn Arg His Leu Lys Asp Ser Ile Pro Phe Asp Leu Ser Leu Tyr Thr
                835                 840                 845
```

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide; competitive inhibitor of
      Zn protease

<400> SEQUENCE: 46

```
Cys Arg Ala Thr Lys Met Leu
  1               5
```

<210> SEQ ID NO 47
<211> LENGTH: 449
<212> TYPE: PRT
<213> ORGANISM: Artificial Sequence
<220> FEATURE:
<223> OTHER INFORMATION: Synthetic botulinum neurotoxin light chain of
      serotype A based on wild-type Clostridium
      botulinum sequence

<400> SEQUENCE: 47

```
Met Val Gln Phe Val Asn Lys Gln Phe Asn Tyr Lys Asp Pro Val Asn
 1               5                  10                  15

Gly Val Asp Ile Ala Tyr Ile Lys Ile Pro Asn Val Gly Gln Met Gln
             20                  25                  30

Pro Val Lys Ala Phe Lys Ile His Asn Lys Ile Trp Val Ile Pro Glu
         35                  40                  45

Arg Asp Thr Phe Thr Asn Pro Glu Glu Gly Asp Leu Asn Pro Pro Pro
 50                  55                  60

Glu Ala Lys Gln Val Pro Val Ser Tyr Tyr Asp Ser Thr Tyr Leu Ser
 65                  70                  75                  80

Thr Asp Asn Glu Lys Asp Asn Tyr Leu Lys Gly Val Thr Lys Leu Phe
                 85                  90                  95

Glu Arg Ile Tyr Ser Thr Asp Leu Gly Arg Met Leu Leu Thr Ser Ile
                100                 105                 110

Val Arg Gly Ile Pro Phe Trp Gly Gly Ser Thr Ile Asp Thr Glu Leu
            115                 120                 125

Lys Val Ile Asp Thr Asn Cys Ile Asn Val Ile Gln Pro Asp Gly Ser
130                 135                 140

Tyr Arg Ser Glu Glu Leu Asn Leu Val Ile Ile Gly Pro Ser Ala Asp
145                 150                 155                 160

Ile Ile Gln Phe Glu Cys Lys Ser Phe Gly His Glu Val Leu Asn Leu
                165                 170                 175

Thr Arg Asn Gly Tyr Gly Ser Thr Gln Tyr Ile Arg Phe Ser Pro Asp
                180                 185                 190

Phe Thr Phe Gly Phe Glu Glu Ser Leu Glu Val Asp Thr Asn Pro Leu
            195                 200                 205

Leu Gly Ala Gly Lys Phe Ala Thr Asp Pro Ala Val Thr Leu Ala His
210                 215                 220

Glu Leu Ile His Ala Gly His Arg Leu Tyr Gly Ile Ala Ile Asn Pro
225                 230                 235                 240

Asn Arg Val Phe Lys Val Asn Thr Asn Ala Tyr Tyr Glu Met Ser Gly
                245                 250                 255

Leu Glu Val Ser Phe Glu Glu Leu Arg Thr Phe Gly Gly His Asp Ala
                260                 265                 270

Lys Phe Ile Asp Ser Leu Gln Glu Asn Glu Phe Arg Leu Tyr Tyr Tyr
            275                 280                 285

Asn Lys Phe Lys Asp Ile Ala Ser Thr Leu Asn Lys Ala Lys Ser Ile
290                 295                 300

Val Gly Thr Thr Ala Ser Leu Gln Tyr Met Lys Asn Val Phe Lys Glu
305                 310                 315                 320

Lys Tyr Leu Leu Ser Glu Asp Thr Ser Gly Lys Phe Ser Val Asp Lys
                325                 330                 335

Leu Lys Phe Asp Lys Leu Tyr Lys Met Leu Thr Glu Ile Tyr Thr Glu
                340                 345                 350

Asp Asn Phe Val Lys Phe Phe Lys Val Leu Asn Arg Lys Thr Tyr Leu
            355                 360                 365

Asn Phe Asp Lys Ala Val Phe Lys Ile Asn Ile Val Pro Lys Val Asn
370                 375                 380

Tyr Thr Ile Tyr Asp Gly Phe Asn Leu Arg Asn Thr Asn Leu Ala Ala
```

-continued

```
385                 390                 395                 400
Asn Phe Asn Gly Gln Asn Thr Glu Ile Asn Asn Met Asn Phe Thr Lys
                405                 410                 415
Leu Lys Asn Phe Thr Gly Leu Phe Glu Phe Tyr Lys Leu Leu Cys Val
            420                 425                 430
Arg Gly Ile Ile Thr Ser Lys Thr Lys Ser Leu Asp Lys Gly Tyr Asn
            435                 440                 445
Lys
```

RECOMBINANT LIGHT CHAINS OF BOTULINUM NEUROTOXINS AND LIGHT CHAIN FUSION PROTEINS FOR USE IN RESEARCH AND CLINICAL THERAPY

This application is a divisional of U.S. patent application Ser. No. 11/293,582 filed on Dec. 2, 2005, abandoned, which is a divisional of U.S. patent application Ser. No. 10/011,588 filed Nov. 6, 2001, issued as U.S. Pat. No. 7,037,680, based on U.S. Provisional Application No. 60/246,774, filed on Nov. 6, 2000 and U.S. provisional Application No. 60/311,966 filed Aug. 9, 2001. U.S. patent application Ser. No. 10/011,588 is a continuation-in-part of U.S. patent application Ser. No. 09/910,186 filed Jul. 20, 2001 issued as U.S. Pat. No. 7,081,529, which is a continuation of U.S. patent application Ser. No. 09/611,419 filed Jul. 6, 2000 issued as U.S. Pat. No. 7,214,787, which is a continuation of U.S. patent application Ser. No. 08/123,975, filed Sep. 21, 1993, abandoned, wherein said application Ser. No. 09/611,419, is based on U.S. Provisional Applications Nos. 60/133,866, 60/133,868, 60/133,869, 60/133,865, 60/133,873, and 60/133,867, all filed May 12, 1999. All priority applications are hereby incorporated herein by reference in their entirety.

FIELD OF THE INVENTION

This invention is directed to construction, expression, and purification of synthetic DNA molecules encoding polypeptides comprising botulinum neurotoxin (BoNT) light chains. The invention is also directed to methods of vaccination against botulism using the expressed peptides.

BACKGROUND OF THE INVENTION

The sporulating, obligate anaerobic, gram-positive bacillus *Clostridium* produces eight forms of antigenically distinct exotoxins. Tetanus neurotoxin (TeNT) is produced by *Clostridium tetani* while *Clostridium botulinum* produces seven different neurotoxins which are differentiated serologically by specific neutralization. The botulinum neurotoxins (BoNT) have been designated as serotypes A, B, $C_1$, D, E, F, and G. Botulinum neurotoxins (BoNT) are the most toxic substances known and are the causative agents of the disease botulism. BoNT exert their action by inhibiting the release of the neurotransmitter acetylcholine at the neuromuscular junction (Habermann, E., et al., (1986), "Clostridial Neurotoxins: Handling and Action at the Cellular and Molecular Level," *Cur. Top. Microbiol. Immunol.*, 129:93-179; Schiavo, G., et al., (1992a), "Tetanus and Botulinum-B Neurotoxins Block Neurotransmitter Release by Proteolytic Cleavage of Synaptobrevin," *Nature*, 359:832-835; Simpson, L. L., (1986), "Molecular Pharmacology of Botulinum Toxin and Tetanus Toxin," *Annu. Rev. Pharmacol. Toxicol.*, 26:427-453) which leads to a state of flaccid paralysis. Indeed, only a few molecules of toxin are required to abolish the action of a nerve cell. Polyclonal antibodies derived from a specific neurotoxin can neutralize the toxic effects of that toxin but will not cross-neutralize another toxin serotype. Thus, to protect against all seven toxins, one needs seven vaccines.

Human botulism poisoning is generally caused by type A, B, E or rarely, by type F toxin. Type A and B are highly poisonous proteins which resist digestion by the enzymes of the gastrointestinal tract. Foodborne botulism poisoning is caused by the toxins present in contaminated food, but wound and infant botulism are caused by in vivo growth in closed wounds and the gastrointestinal tract respectively. The toxins primarily act by inhibiting the neurotransmitter acetylcholine at the neuromuscular junction, causing paralysis. Another means for botulism poisoning to occur is the deliberate introduction of the toxin(s) into the environment as might occur in biological warfare or a terrorist attack. When the cause of botulism is produced by toxin rather than by in vivo infection the onset of neurologic symptoms is usually abrupt and occurs within 18 to 36 hours after ingestion. The most common immediate cause of death is respiratory failure due to diaphragmatic paralysis. Home canned foods are the most common sources of toxins. The most frequently implicated toxin is toxin A, which is responsible for more than 50% of morbidity resulting from botulinum toxin.

Botulinum and tetanus neurotoxins are a new class of zinc-endopeptidases that act selectively at discrete sites on three synaptosomal proteins of the neuroexocytotic apparatus. See Montecucco and Schiavo, 1995, and Schiavo, 1995, for review. These neurotoxins are the most potent of all the known toxins. The botulinum neurotoxins (BoNT), designed A-G, produced by seven immunologically distinct strains of *Clostridium botulinum* cause death by flaccid muscle paralysis at the neuromuscular junction. Extreme toxicity of these toxins and their lability in purified preparations have limited any detailed characterizations.

These neurotoxins are expressed as 150-kDa single polypeptides (termed dichains) containing a disulfide bond between the 50-kDa N-terminal light chain (LC) and the 100-kDa C-terminal heavy chain (HC). A post-translational cryptic cleavage generates the two chains connected by a disulfide bond. The LC contains the toxic, zinc-endopeptidase catalytic domain. The 100-kDa HC may be further proteolyzed into a 50-kDa N-terminal membrane-spanning domain ($H_n$) and a 50-kDa C-terminal receptor-binding domain ($H_c$).

With three functional domains, the mechanism of action of these neurotoxins is multiphasic: (1) The $H_c$ domain plays a role in binding the toxins to specific receptors located exclusively on the peripheral cholinergic nerve endings (Black and Dolly, 1986). (2) The $H_n$ domain is believed to participate in a receptor-mediated endocytic pore formation in an acidic environment, allowing translocation of the catalytic LC into the cytosol. Reducing the disulfide bond connecting the LC with the H upon exposure to the cytosol or within the acidic endosome (Montal et al., 1992) releases the catalytic LC into the cytosol. (3) The LC then cleaves at specific sites of one of the three different soluable NSF attachment protein receptor (SNARE) proteins, synaptobrevin, syntaxin, or synaptosomal associated protein of 25 kDa (SNAP-25) (Blasi et al., 1993; Schiavo et al., 1993, 1994; Shone et al., 1993; Foran et al., 1996). These proteins are essential for synaptic vesicle fusion in exocytosis. Their proteolysis inhibits exocytosis and blocks acetylcholine secretion, leading ultimately to muscular paralysis. The LC itself is nontoxic because it cannot translocate through the cholinergic nerve ending into the cytosol. However, in digitonin-permeabilized chromaffin cells, the LC inhibits exocytosis (Bittner et al., 1989), and direct microinjection of the LC into the cytosol results in blockage of membrane exocytosis (Bittner et al., 1989; Bi et al., 1995).

The LC of all known clostridial neurotoxins contain the sequence HExxH that is characteristic of zinc-endoproteinases (Thompson et al., 1990). The essential role of zinc on the structure and catalysis of the neurotoxins is established (Fu et al., 1998). A unique feature of the neurotoxins' protease activity is their substrate requirement. Short peptides encompassing only the cleavage sites are not hydrolyzed (Foran et al., 1994; Shone and Roberts, 1994). A specific secondary and/or tertiary structure of the substrate is most probably recognized (Washbourne et al., 1997; Lebeda and Olson, 1994; Rossetto et al., 1994) rather than a primary structure alone, as is the case with most other proteases. Most importantly, their identified natural substrates are proteins involved in the fundamental process of exocytosis (Blasi et al., 1993; Schiavo et al., 1993, 1994; Shone et al., 1993; Foran et al., 1996). Light chain also is the target of an intensive effort to design drugs, inhibitors, and vaccines. A detailed understanding of its structure and function is thus very important.

The present invention describes the construction and overexpression of a synthetic gene for the nontoxic LC of BoNT/A in *E. coli*. The high level of expression obtained enabled purification of gram quantities of LC from 1 L of culture as well as extensive characterization. The preparation of the rBoNT/A LC was highly soluble, stable at 4° C. for at least 6 months, and had the expected enzymatic and functional properties. For the first time, a cysteine residue was tentatively identified in the vicinity of the active site which, when modified by mercuric compounds, led to complete loss of enzymatic activity.

The BoNTs and their LCs are targets of vaccine development, drug design, and mechanism studies because of their potential role in biological warfare, wide therapeutic applications, and potential to facilitate elucidation of the mechanism of membrane exocytosis. In spite of such immense importance, studies of the LC have been limited by its availability. Commercially available LC is prepared by separating it from the dichain toxins under denaturing conditions. These preparations therefore retain some contaminating toxicity of the dichain, have low solubility, and often begin to proteolytically degrade and start losing activity within hours of storage in solution.

The LC of serotype A has been separated and purified from the full-length toxin by QAE-Sephadex™ chromatography from 2 M urea; however, the preparation suffers from low solubility (Shone and Tranter, 1995). The LC of serotype C was similarly obtained at a level of <5 mg/10 L culture of *C. botulinum* (Syuto and Kubo, 1981). These preparations almost invariably contain contaminating full-length toxins, and the commercially available preparations precipitate from solution or undergo proteolytic degradation upon hours of storage in solution. More recently the LC of tetanus neurotoxin (Li et al., 1994) and of BoNT/A (Zhou et al., 1995) were expressed in *E. coli* as maltose-binding proteins and purified in 0.5 mg quantities from 1-L cultures (Zhou et al., 1995). However, the poor expression of the cloned products, probably due to rare codon usage in clostridial DNA (Makoff et al., 1989, Winkler and Wood, 1988), remained a major hurdle in obtaining adequate amount of the protein for structural and functional studies.

Most of the clostridial strains contain specific endogenous proteases which activate the toxins at a protease-sensitive loop located approximately one third of the way into the molecule from the amino-terminal end. Upon reduction and fractionation (electrophoretically or chromatographically), the two chains can be separated; one chain has a Mr of ~100 kDa and is referred to as the heavy chain while the other has a Mr ~50 kDa and is termed the light chain.

The mechanism of nerve intoxication is accomplished through the interplay of three key events, each of which is performed by a separate portion of the neurotoxin protein. First, the carboxy half of the heavy chain (fragment C or $H_c$ is required for receptor-specific binding to cholinergic nerve cells (Black, J. D., et al., (1986), "Interaction of $^{125}$I-botulinum. Neurotoxins with Nerve Terminals. I. Ultrastructural Autoradiographic Localization and Quantitation of Distinct Membrane Acceptors for Types A and B on Motor Nerves," *J. Cell Biol.*, 103:521-534; Nishiki, T.-I., et al., (1994), "Identification of Protein Receptor for *Clostridium botulinum* Type B Neurotoxin in Rat Brain Synaptosomes," *J. Biol. Chem.*, 269:10498-10503; Shone, C. C., et al., (1985), "Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activity, *Eur. J. Biochem.*, 151:75-82). Evidence suggests that polysialogangliosides (van Heyningen, W. E., (1968), "Tetanus," *Sci. Am.*, 218:69-77) could act as receptors for the toxins but the data supporting a specific receptor remains equivocal (Middlebrook, J. L., (1989), "Cell Surface Receptors for Protein Toxins," *Botulinum Neurotoxins and Tetanus Toxin*, (Simpson, L. L., Ed.) pp. 95-119, Academic Press, New York). After binding, the toxin is internalized into an endosome through receptor-mediated endocytosis (Shone, C. C., et al., (1987), "A 50-kDa Fragment from the $NH_2$-terminus of the Heavy Subunit of *Clostridium botulinum* Type A Neurotoxin Forms Channels in Lipid Vesicles, *Euro. J. Biochem.*, 167:175-180).

The amino terminal half of the heavy chain is believed to participate in the translocation mechanism of the light chain across the endosomal membrane (Simpson, 1986; Poulain, B., et al., (1991), "Heterologous Combinations of Heavy and Light Chains from Botulinum Neurotoxin A and Tetanus Toxin Inhibit Neurotransmitter Release in *Aplysia*," *J. Biol. Chem.*, 266:9580-9585; Montal, M. S., et al., (1992), "Identification of an Ion Channel-Forming Motif in the Primary Structure of Tetanus and Botulinum Neurotoxins," *FEBS*, 313:12-18). The low pH environment of the endosome may trigger a conformational change in the translocation domain, thus forming a channel for the light chain.

The final event of intoxication involves enzymatic activity of the light chain, a zinc-dependent endoprotease (Schiavo, 1992a; Schiavo, G., et al., (1992b), "Tetanus Toxin is a Zinc Protein and its Inhibition of Neurotransmitter Release and Protease Activity Depend on Zinc," *EMBO J.*, 11:3577-3583), on key synaptic vesicle proteins (Schiavo, 1992a; Oguma, K., et al., (1995), "Structure and Function of *Clostridium botulinum* Toxins," *Microbiol. Immunol.*, 39:161-168; Schiavo, G., et al., (1993), "Identification of the Nerve Terminal Targets of Botulinum Neurotoxin Serotypes A, D, and E," *J. Biol. Chem.*, 268:23784-23787; Shone, C. C., et al., (1993), "Proteolytic Cleavage of Synthetic Fragments of Vesicle-Associated Membrane Protein, Isoform-2 by Botulinum Type B Neurotoxin," *Eur. J. Biochem.*, 217:965-971) necessary for neurotransmitter release. The light chains of BoNT serotypes A, $C_1$, and E cleave SNAP-25 (synaptosomal-associated protein of M25,000), serotypes B, D, F, and G cleave vesicle-associated membrane protein (VAMP)/synaptobrevin (synaptic vesicle-associated membrane protein); and serotype $C_1$ cleaves syntaxin. Inactivation of SNAP-25, VAMP, or syntaxin by BoNT leads to an inability of the nerve cells to release acetylcholine resulting in neuromuscular paralysis and possible death, if the condition remains untreated.

The majority of research related to botulinum toxin has focused on the development of vaccines. Currently, a pentavalent toxoid vaccine against serotypes A through E (Anderson, J. H., et al., (1981), "Clinical Evaluation of Botulinum Toxoids," *Biomedical Aspects of Botulism*, (Lewis, G. E., Ed.), pp. 233-246, Academic Press, New York; Ellis, R. J., (1982), "Immunobiologic Agents and Drugs Available from the Centers for Disease Control. Descriptions, Recommendations, Adverse Reactions and Serologic Response," 3rd ed., Centers for Disease Control. Atlanta, Ga.; Fiock, M. A., et al., (1963), "Studies of Immunities to Toxins of *Clostridium*

*botulinum*. IX. Immunologic Response of Man to Purified Pentavalent ABCDE Botulinum Toxoid," *J. Immunol.*, 90:697-702; Siegel, L. S., (1988), "Human Immune Response to Botulinum Pentavalent (ABCDE) Toxoid Determined by a Neutralization Test and by an Enzyme-Linked Immunosorbent Assay," *J. Clin. Microbiol.*, 26:2351-2356), available under Investigational New Drug (IND) status, is used to immunize specific populations of at-risk individuals, i.e., scientists and health care providers who handle BoNT and military personnel who may be subjected to weaponized forms of the toxin. Though serotypes A, B, and E are most associated with botulism outbreaks in humans, type F has also been diagnosed (Midura, T. F., et al., (1972), "*Clostridium botulinum* Type F: Isolation from Venison Jerky," *Appl. Microbiol.*, 24:165-167; Green, J., et al., (1983), "Human Botulism (Type F)—A Rare Type," *Am. J. Med.*, 75:893-895; Sonnabend, W. F., et al., (1987), "Intestinal Toxicoinfection by *Clostridium botulinum* Type F in an Adult. Case Associated with Guillian-Barre Syndrome," *Lancet*, 1:357-361; Hatheway, C. L., (1976), "Toxoid of *Clostridium botulinum* Type F: Purification and Immunogenicity Studies," *Appl. Environ. Microbiol.*, 31:234-242). A separate monovalent toxoid vaccine against BoNTF is available under IND status. Hatheway demonstrated that the BoNTF toxoid could protect guinea pigs against a homologous challenge (Wadsworth, J. D. F., et al., (1990), "Botulinum Type F Neurotoxin," *Biochem. J.*, 268:123-128).

New-generation, recombinant vaccines have also been developed by USAMRIID (e.g. Dertzbaugh M T, Sep. 11, 2001, U.S. Pat. No. 6,287,566; U.S. application Ser. No. 09/910,186 filed Jul. 20, 2001; and U.S. application Ser. No. 09/611,419 filed Jul. 6, 2000) and commercial sources (e.g. Ophidian Pharmaceuticals, Inc. Williams J A, Jul. 6, 1999, U.S. Pat. No. 5,919,665; using clones supplied by USAMRIID).

Most vaccine studies have focused on the botulinum toxin heavy chain, leaving the light chain largely ignored. In 1995, Zhou et al. discovered that a single mutation in the light chain of botulinum neurotoxin serotype A abolished its neurotoxicity and its ability to cleave SNAP-25, one of the natural substrates, when reconstituted with the heavy chain. See Zhou, L. et al., (1995), "Expression and Purification of Botulinum Neurotoxin A: A Single Mutation Abolishes its Cleavage of SNAP-25 and Neurotoxicity after Reconstitution with the Heavy Chain," *Biochem.*, 34:15175-15181.) This raised the possibility that the mutated light chain might have various research or therapeutic uses. Further research produced a recombinant light chain (Li, L. and Singh, B. R., (1999), "High-Level Expression, Purification, and Characterization of Recombinant Type A Botulinum Neurotoxin Light Chain," *Protein Expression and Purification*, 17:339-344) and a construct comprising the minimum essential light chain domain (Kadkhodayan, S., et al., (2000), "Cloning, Expression, and One-Step Purification of the Minimal Essential Domain of the Light Chain of Botulinum Neurotoxin Type A," *Protein Expression and Purification*, 19:125-130).

Recombinant production methods alleviate many of the problems associated with the toxoid, such as the need for a dedicated manufacturing facility. Presently, many cGMP facilities are in existence and available that could manufacture a recombinant product. There would be no need to culture large quantities of a hazardous toxin-producing bacterium. Production yields from a genetically engineered product are expected to be high. Recombinant products would be purer, less reactogenic, and more fully characterized. Thus, the cost of a recombinant product would be expected to be much lower than a toxoid because there would be no expenditures required to support a dedicated facility, and the higher production yields would reduce the cost of therapeutic and research products.

However, recombinant methods as described in the publications above do not yield optimal results because botulinum codons are not translated well in other organisms commonly used for production, such as *E. coli* or yeast. Furthermore, no easily translatable, recombinant form of the non-neurotoxic, mutated light chain presently exists. Recombinant forms of both functional and non-neurotoxic botulinum neurotoxin that may be translated efficiently in either *E. coli* or yeast are needed for research and therapeutic purposes.

Commercially available BoNT LC is prepared by separation from the di-chain toxins. These preparations, therefore, retain some contaminating toxicity, have low solubility, and undergo proteolytic degradation within hours and days of storage in solution. Many clinical disorders are presently being treated with a botulinum neurotoxin complex that is isolated from the bacterium, *Clostridium botulinum*. There is no data to demonstrate that the binding proteins play any role in the therapeutic effects of the drug. The binding proteins, however, probably contribute to the immunological response in those patients that become non-responsive to drug treatment. Recombinant products could be manufactured under conditions that are more amenable to product characterization. Chimeras of the drug product could also be produced by domain switching. Chimeras could potentially increase the number of potential useful drug products.

Recently, the BoNT LC of serotype A has been expressed as a maltose-binding protein and purified in 0.5 mg quantities from 1 liter culture (Zhou et al., 1995). The poor expression of the native gene was probably due to the high A+T composition found in the clostridial DNA.

SUMMARY OF THE INVENTION

The present invention relates to the design and construction of synthetic DNA molecules that encode one of the seven light chains of *Clostridium botulinum* neurotoxin and are capable of being expressed in heterologous prokaryotic or eukaryotic hosts. The invention is based, in part, on modifying the wild-type BoNT sequence according to the codon usage normally found in genes that are highly expressed in the host organism. By selecting codons rich in G+C content, the synthetic DNA molecules may further be designed to lower the high A+T rich base composition found in clostridial genes.

The invention further relates to methods of expressing and purifying recombinant BoNT light chains. According to the invention, BoNT LC may be expressed in a heterologous host system by itself or as a fusion to another protein or carrier. For example, the BoNT LC may be fused to a synthetic or wild-type BoNT heavy chain or a fragment thereof. BoNT LC of the invention may or may not have catalytic activity as a zinc protease. In some embodiments of the invention, catalytically inactive BoNT LC is fused to a BoNT heavy chain forming a mutant holotoxin. Non-enzymatic, non-toxic mutant holotoxins are capable of being internalized into nerve cells. In addition, mutant holotoxins may be used as transporters to carry other molecules into colinergic nerve cells.

The invention further provides methods and compositions for eliciting an immune response to BoNT LC and BoNT HN. The invention provides preparations of BoNT LC and BoNT HN that are capable of eliciting protective immunity in a mammal.

BRIEF DESCRIPTION OF THE DRAWINGS

FIG. 3. UV-visible absorption spectrum of the rBoNT/A LC.

FIG. 4. Long-term stability at 4° C. (A) and thermal stability (B) of the rBoNT/A LC. (A) Aliquots of the LC from one single preparation were assayed at the indicated times; (B) 50 μl aliquots of the LC in buffer G containing 1 mM DTT and 50 μM $ZnCl_2$ were taken in Eppendorf tubes and heated for 5 min at the indicated temperatures. After cooling on ice for 60 min, the supernatants were assayed for proteolytic activity.

FIG. 18. Purification of LcA, LcA+Belt, and LcA+Hn from *E. coli* cells.

DETAILED DESCRIPTION OF THE INVENTION

Figures 1, 2:
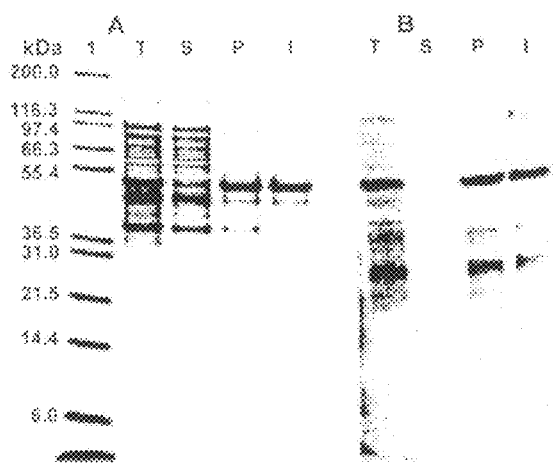
FIG. 1. Nucleotide sequence of rBoNT/A LC and the corresponding amino acid sequence. The codon in italics (i.e., encoding the penultimate Val residue) and at the 5' end of the gene was introduced to create and maintain the Nco I restriction enzyme site. Codons in italics (i.e., encoding LVPRGS; residues 450-455 of SEQ ID NO:5) at the 3' end of the gene encode a thrombin protease cleavage site for removing the His tag after purification.
FIG. 2. SDS-PAGE followed by Coomassie stain (A) and Western blot (B) of crude and purified BONT/A LC expressed in *E. coli* containing the synthetic gene for BONT/A LC in a multicopy plasmid pET24. Total cellular protein (T), soluble supernatant (S), insoluble pellet (P), and purified inclusion bodies (I) were prepared as described in Section 2. Lane 1 shows Novex wide-range molecular-mass markers (0.8-3.0 μg/band). The sarkosyl solubilized inclusion bodies of the LC had the same electrophoretic behavior as (I). About 20 μg of protein was applied per lane. Western blot used affinity-purified rabbit polyclonal antibodies against a 16-residue N-terminal sequence of the BONT/A LC as the primary antibody and a peroxidase-coupled goat anti-rabbit IgG (H+L) as the secondary antibody. Bands were visualized by a chromogenic substrate.

In some embodiments the invention provides methods and nucleic acids for expressing *Clostridium botulinum* genes in other prokaryotes and eukaryotes. More specifically, the invention provides methods and nucleic acids for expressing botulinum neurotoxin (BoNT) light chains (LC) in *Escherichia coli* or *Pichia pastoris*. In order to be expressed in *Escherichia coli* or *Pichia pastoris*, the sequence of DNA encoding wild-type BoNT LC is engineered to replace some *Clostridium* codons that are rare or unrecognized in the host organism and to reduce the A+T content. The recombinant or synthetic DNA molecules of the invention are preferably designed with codon usage normally found in genes that are highly expressed in the host organism, e.g. *Escherichia coli* or *Pichia pastoris*. By selecting codons rich in G+C content, synthetic DNA molecules may also be designed to lower the A+T-rich base composition found in the Clostridial genes. According to the invention, a host cell is a cell of any organism other than *Clostridium*. Nonlimiting examples of host cells include gram negative bacteria, yeast, mammalian cells, and plant cells.

In some embodiments of the invention, upon expression of the DNA, a BoNT LC is produced in a heterologous host system by itself or as a fusion with another protein or a carrier. Proteins with which BoNT LCs may be fused include BoNT HCs, maltose-bonding proteins, other neurotoxins, neuropeptides, and autofluorescent proteins. A synthetic light chain gene may be genetically fused to a gene encoding a BoNT HC, producing recombinant botulinum toxin.

In some embodiments of the invention, BoNT LC is produced that is (i) substantially free of contaminating toxicity, (ii) moderately to highly soluble in aqueous media, (iii) stable for at least about six months at 4° C., (iv) catalytically active, (v) functionally active, or combinations thereof. In some embodiments of the invention, gram quantities of BoNT LC may be obtained per liter of culture medium. In some embodiments of the invention, a recombinant BoNT LC may reduce any immunological response that may result from the presence of binding proteins associated with the recombinant BoNT LC.

In some embodiments, the invention provides BoNT LC that substantially lacks catalytic activity as a zinc protease as measured by the SNAP-25 assay described in Examples 8, 17, and, 25 below. In some embodiments, the invention provides nucleic acids that encode recombinant BoNT LC substantially lacking catalytic activity as a zinc protease, wherein amino acids in or spatially near the active site are deleted, replaced or modified relative to wild-type native BoNT. Catalytically inactive BoNT LC may be fused with BoNT HC to form a mutant recombinant holotoxin. Such holotoxins may be used to carry molecules, e.g., drugs, into cholinergic nerve cells.

In some embodiments, this invention provides a nucleic acid comprising a nucleic acid sequence encoding the N-terminal portion of a full length botulinum neurotoxin (BoNT) selected from the group consisting of BoNT serotype A, BoNT serotype B, BoNT serotype C1, BoNT serotype D, BoNT serotype E, BoNT serotype F, and BoNT serotype G, wherein said nucleic acid is expressible in a recombinant organism selected from *Escherichia coli* and *Pichia pastoris*. In some preferred embodiments, the nucleic acid corresponds in length and encoded amino acid sequence to the BoNT light chain (LC). In some particularly preferred embodiments, the nucleic acid comprises a nucleic acid sequence selected from SEQ ID NO:4 (serotype A), SEQ ID NO:6 (serotype B), SEQ Id NO:8 (serotype C1), SEQ ID NO:10 (serotype D), SEQ ID NO:12 (serotype E), SEQ ID NO:14 (serotype F), SEQ ID NO:16 (serotype G), SEQ ID NO:22 (serotype B), SEQ Id NO:26 (serotype C1), SEQ ID NO:30 (serotype D), SEQ ID NO:34 (serotype E), SEQ ID NO:38 (serotype F), and SEQ ID NO:42 (serotype G).

In preferred embodiments, nucleic acids of the invention are synthetic nucleic acids. In some preferred embodiments, the sequence of the nucleic acid is designed by selecting at least a portion of the codons encoding BoNT LC from codons preferred for expression in a host organism, which may be selected from gram negative bacteria, yeast, and mammalian cell lines; preferably, the host organism is *Escherichia coli* or *Pichia pastoris*. The nucleic acid sequence encoding LC may be designed by replacing *Clostridium* codons with host organism codons that encode the same amino acid, but have a higher G+C content. Conservative amino acid substitutions are within the contemplation and scope of the invention. In preferred embodiments of the invention, a nucleic acid encoding a recombinant BoNT or fragment thereof is capable of being expressed in a recombinant host organism with higher yield than a second nucleic acid encoding substantially the same amino acid sequence, said second nucleic acid fragment having the wild-type *Clostridium botulinum* nucleic acid sequence.

Codon usage tables for microorganisms have been published. See e.g. Andersson S G E, Kurland C G, 1990, "Codon preferences in free-living microorganisms" Microbiol. Rev 54:198-210; Sreekrishna, 1993, "Optimizing protein expression and secretion in *Pichia pastoris*" in Industrial Microorganisms Basic and Applied Molecular Genetics, Baltz, Hegeman, Skatrud, eds, Washington D.C., p. 123; Makofl A J, Oxer M D, Romanos M A, Fairweather N F, Ballantine S, 1989, "Expression of tetanus toxin fragment C in *E. coli*: high level expression by removing rare codons" Nuc. Acids Res. 17(24): 10191-10202. Table 3 of Skreekrishna is a chart depicting codon usage in *Pichia pastoris*. This table was generated by listing the codons found in a number of highly expressed genes in *P. pastoris*. The codon data was obtained by sequencing the genes and then listing which codons were found in the genes.

From such tables, it is clear that amino acid residues can be encoded by multiple codons. When constructing synthetic DNA molecules using *P. pastoris* codon usage, it is preferred to use only those codons that are found in naturally occurring genes of *P. pastoris*, and it should be attempted to keep them in the same ratio found in the genes of the natural organism. When the clostridial gene has an overall A+T richness of greater than 70% and A+T regions that have spikes of A+T of 95% or higher, they have to be lowered for expression in expression systems like yeast. Preferably, the overall A+T richness is lowered below 60% and the A+T content in spikes is also lowered to 60% or below. In preferred embodiments of the invention, maintaining the same codon ratio (e.g., for glycine GGG was not found, GGA was found 22% of the time, GGT was found 74% of the time, GGC was found 3% of the time) is balanced with reducing the high A+T content. In the construction of the DNA molecules of the invention, it is preferred to avoid spikes where the A+T content exceeds about 55%.

According to the invention, a spike may be a set of about 20 to about 100 consecutive nucleotides. A spike having a high A+T content greater than 80% or 90% may function as transcription termination sites in host systems, thereby interfering with expression. Preferred synthetic DNA molecules of the invention are substantially free of spikes of 50 consecutive nucleotides having an A+T content higher than about 75%. Alternatively, preferred synthetic DNA molecules of the invention are substantially free of spikes of 75 consecutive nucleotides having an A+T content higher than about 70%. Alternatively, preferred synthetic DNA molecules of the invention are substantially free of spikes of 100 consecutive nucleotides having an A+T content higher than about 60%.

A synthetic DNA molecule of the invention designed by using *E. coli* codons is expressed fairly well in *P. pastoris*. Similarly, a synthetic gene using *P. pastoris* codons also appears to be expressed well in *E. coli*.

In some embodiments, this invention provides an expression vector comprising a nucleic acid of this invention, whereby LC is produced upon transfection of a host organism with the expression vector. Another embodiment of this invention provides a method of preparing a polypeptide comprising the BoNT LC selected from the group consisting of BoNT serotype A, BoNT serotype B, BoNT serotype C, BoNT serotype D, BoNT serotype E, BoNT serotype F, and BoNT serotype G, said method comprising culturing a recombinant host organism transfected with an expression vector of this invention under conditions wherein BoNT LC is expressed. Preferably, the recombinant host organism is a eukaryote. In another preferred embodiment, the method of this invention further comprises recovering insoluble protein from the host organism, whereby a fraction enriched in BoNT LC is obtained. *E. coli* is a preferred host for expressing catalytically active (i.e., proteolytically active) LC. *Pichia pastoris* is a preferred host organism for expressing inactive or mutated LC. *Pichia pastoris* has SNARE proteins which probably get inactivated by catalytically-active LC.

In some embodiments, the invention provides an immunogenic composition comprising a suitable carrier and a BoNT LC selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding BoNT LC. More preferably, the immunogenic composition is prepared by a method wherein an insoluble protein fraction enriched in BoNT LC is recovered from said recombinant organism. More preferably, the immunogenic composition is prepared by the method of Example 30.

According to some non-limiting embodiments, the invention provides reagents and compositions that are useful for developing therapeutic interventions against BoNT. For example, the recombinant BoNT nucleic acids and polypeptides of the invention may be used to screen for botulinum neurotoxin inhibitors.

In some embodiments, the invention provides therapeutic agents for clinical disorders such as dystonias, spasticity, and pain. According to these embodiments, the agents may be prepared by first expressing and purifying BoNT LC independently of any portion of the heavy chain. The BoNT LC so produced is then fused to the heavy chain or fragments thereof, e.g., HN and HC. Alternatively, BoNT LC may be coexpressed and/or copurified with BoNT HC or fragments thereof and then fused to BoNT HC or fragments thereof. These agents may be used in clinical (human) or veterinary (non-human animal) applications.

In some embodiments, the invention provides agents that may be useful for treating disorders associated with cholinergic nerve function, SNAP-25, VAMP, syntaxin or combinations thereof. In some embodiments, the invention provides agents that may be useful for reducing any immunological response that may result from the presence of binding proteins associated with the agents. For example, the native BoNT holotoxin is highly immunogenic and some patients become refractory to continued treatment with it over time as their protective antitoxin titer rises. The efficacy of holotoxin-based drugs (e.g., BOTOX, Myobloc/Neurobloc, Dysport) may be improved by pretreating patients having a high titer of anti-holotoxin antibodies with a holotoxin fragment such as Lc, Hn, or Hc. These fragments may bind the anti-holotoxin antibodies making them unavailable for binding the subsequently administered holotoxin. This may work for a short time (months to a few years) realizing eventually that the antibody level may be built up so much that the drug can no longer be effective even with the addition of fragments. At this point in time, the patients will have to use a different serotype toxin drug or a chimera of the toxin (i.e., mixing toxin domains).

In further embodiments, the invention provides an immunogenic composition comprising a suitable carrier and a BoNT LC selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding BoNT LC. More preferably, the immunogenic composition is prepared by a method wherein an insoluble protein fraction enriched in BoNT LC is recovered from said recombinant organism.

The LC is present in immunogenic compositions of the invention in an amount sufficient to induce an immunogenic response thereto.

Two of the major advantages of the recombinant botulinum neurotoxins and fragments of the invention are the safety and high yields possible. First, the recombinantly produced botulinum neurotoxin (rBoNT) protein fragments are completely nontoxic and are, thus, very safe. The fermentation of the host cell harboring the rBoNT gene (e.g., *Escherichia coli* or *Pichia pastoris*) does not require the high biological containment facilities presently needed to ferment the spore-forming *Clostridium botulinum* required for the production of the neurotoxin light chains. Second, synthetic DNA molecules of the invention can be placed in high expression systems and used to make much larger quantities of the BoNT fragments than toxin produced by the parent organism, *Clostridium botulinum*. Thus, there may be immense cost savings because it will be easier and safer to produce much larger quantities of the proteins for various uses including vaccination.

Synthetic DNA molecules as described herein may be transfected into suitable host organisms to create recombinant production organisms. Cultures of these recombinant organisms can then be used to produce recombinant BoNT fragments or holotoxins. Exemplary techniques for transfection and production of BoNT fragments are shown in the Examples. Alternative techniques are well documented in the literature See, e.g., Maniatis, Fritsch & Sambrook, "Molecular Cloning: A Laboratory Manual" (1982); Ausubel, "Current Protocols in Molecular Biology" (1991); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989). Such techniques are explained fully in the literature. Modification of these techniques within the scope of this invention is within the skill in the art.

Recombinant forms of botulinum neurotoxin light chain may be useful in one or more of the following applications: strabismus and other disorders of ocular motility, dystonia, blepharospasm, cervical dystonia, oromandibular dystonia, laryngeal dystonia (spasmodic dysphonia), limb dystonia, hemifacial spasm and other facial dyskinesias, tremors of the head and hands, eyelid, cervical, and other tics, spasticity (e.g. anal), Stiff-Person syndrome, bladder dysfunction (e.g. in patients with spinal-cord injury), segmental myoclonus and other hyperkinetic disorders, cosmetic treatment of glabelar frown lines and other facial wrinkles, and all conditions characterized by hyperactivity of the lower motor neuron. See Cardoso and Jankovic, 1995, "Clinical use of botulinum neurotoxins" Curr Top Microbiol Immunol. 195:123-41 and references cited therein. The light chain may further be used to control autonomic nerve function (U.S. Pat. No. 5,766,605) or tiptoe-walking due to stiff muscles common in children with cerebral palsy, according to findings published in the November 2001 issue of *Pediatrics*.

Absolute contraindications to the use of BONT are allergy to the drug and infection or inflammation at the proposed injection site whereas myasthenia gravis, Eaton-Lambert syndrome, motor neuron disease, and coagulopathy are relative contraindications (National Institutes Of Health Consensus Development Conference Statement On Clinical Use Of Botulinum Toxin 1991; Report Of The Therapeutics And Technology Assessment Subcommittee Of The American Academy Of Neurology 1990). Safety for use during pregnancy and lactation has not been firmly established (National Institutes Of Health Consensus Development Conference Statement On Clinical Use Of Botulinum Toxin 1991).

The invention contemplates isoforms of the light chain as well as chimeras with other domains of the toxin or other proteins. In other words, gene fragments with DNA sequences and amino acid sequences not identical to those disclosed herein may be discovered in nature or created in a laboratory. The invention contemplates the production of any protein or polypeptide that has biological activity/functionality similar to the wild-type botulinum neurotoxin light chain, e.g. cell binding, translocation across membrane, catalytic activity sufficient to inactivate critical proteins in a cell involved with protein trafficking, release of various chemical transmitters (i.e., acetylcholine, glutamate, etc), hormones, etc.

For example, the light chain and translocation domain may be combined with a protein or peptide that targets a different receptor and/or cell-type. In addition, the invention contemplates therapeutic delivery of synthetic DNA molecules of the invention to cells via viral vectors such as adenovirus or other gene therapy techniques.

EXAMPLES

In order to facilitate a more complete understanding of the invention, a number of nonlimiting Examples are provided below for illustration purposes only. To advance these purposes, the Examples are arranged in four sets: Examples 1-13, Examples 14-20, Examples 21-29, and Example 30.

Example 1

Chemicals, Buffers, and Reagents

Buffer T (20 mM Tris-HCl, pH 9.2) and buffer G (50 mM sodium glycine, pH 9.0) were used as indicated. SKL (sodium N-lauryl sarcosine or sarkosyl) was from Sigma. Highly purified (>95%) full-length BoNT/A was purchased from List Biologicals (Campbell, Calif.). Rabbit polyclonal antibodies against a 16-residue N-terminal sequence (PFVNKQFNYKDPVNGV; SEQ ID NO:1) of the BONT/A LC were produced and affinity purified by Research Genetics (Huntsville, Ala.). Peroxidase-coupled goat anti-rabbit and anti-mouse IgG (H+L) and ABTS substrate were from Kirkegaard Perry Laboratories (Gaithersburg, Md.). Oligonucleotides, designed for *E. coli* codon usage (Anderson and Kurland, 1990) and ranging in size from 70 to 100 nucleotides, were synthesized by Macromolecular Resources (Fort Collins, Colo.).

Example 2

Construction and Expression of a Synthetic DNA Encoding rBoNT/A LC

The DNA encoding the enzymatic LC domain of BoNT/A was assembled from three segments, a 335-base pair (bp) Sal I-Sph I fragment, a 600-bp Sph I-Kpn I fragment, and a 460-bp Kpn I EcoR I fragment. To construct the first segment, six oligonucleotide pairs were annealed, ligated, and, after PCR amplification, inserted into pGEM3Zf at Sal I-Sph I restriction enzyme sites. The second segment was built by annealing and ligating eight oligonucleotide pairs, followed by its amplification and insertion into the Sph I and Kpn I sites of pGEM3Zf. The final segment was constructed by annealing and ligating six oligonucleotide pairs, followed by its amplification and insertion into the Kpn I-EcoR I sites of pGEM3Zf. Nucleotide sequencing of gene fragments in pGEM3Zf was performed to identify clones in each group with minimal misincorporations. In vitro mutagenesis was performed to correct the misincorporations in the BoNT/A LC minigene fragments. Directional gene assembly via 600-bp and 460-bp fragments in pGEM3Zf was followed by the insertion of the 335-bp fragment.

In the design of the synthetic DNA, the 5' oligonucleotide for amplifying the gene's 5' terminus consisted of an anchored Sal I site followed by an EcoR I site and an Nco I site to facilitate directional subcloning into the E. coli expression vector, pET24d. The 3' oligonucleotide contained a hexahistidine tag with a thrombin protease cleavage site for creating a carboxyl-terminal removable histidine tag. The 3' end also included the restriction enzyme sites for BamH I and EcoR I.

The full-length gene was excised from pGEM3Zf5 with an Nco I-EcoR I and subcloned into a similarly digested pET24d vector. The resulting ligated construct was used to transform E. coli BL21(DE3) cells. Two clones were assayed for their ability to express rBoNTA LC. Single colonies were inoculated into 5 ml of Luria broth (LB) containing 50 μg/ml of kanamycin and grown overnight at 37° C. The overnight cultures (500 μL) were used to inoculate 50 ml of LB containing 50 μg/ml of kanamycin. When the cultures reached $OD_{600}$ of 0.8, induction was initiated by addition of isopropyl-β-D-thiogalactoside (IPTG) (final concentration, 1.0 mM). The cultures were induced for 2 hr at 37° C., harvested, and analyzed for expressed products on SDS-PAGE.

Results

A synthetic DNA encoding rBoNTA LC was designed with E. coli codon usage, constructed, and expressed in E. coli. The native nucleic acid sequence from C. botulinum type A NTCC 2916 (Thompson et al., 1990) was used as the template for preparing synthetic LC sequences of the invention.

At the 5' end of the DNA, an Nco I restriction enzyme site was employed as a cloning site and palindrome to provide an initiation codon. The use of this Nco I site necessitated the use of a filler codon (GTT) between the Met initiation codon (ATG) and the codon (CAG) specifying the first amino acid residue in the LC (i.e., Q). This resulted in the introduction of one extra amino acid, Val, as the N-terminal residue (after the initiating Met). This extra and new amino acid, however, did not interfere with expression or activity. The length of the LC (448 residues) to be expressed was chosen from the sequence of amino acids around the nicking site (DasGupta and Dekleva, 1990) (FIG. 1). At the C-terminal end (i.e., DKGYNK; residues 444-449 of SEQ ID NO:5), a hexa-His tag was incorporated for affinity purification and a thrombin cleavage site (LVPRGS; residues 450-455 of SEQ ID NO:5) was incorporated for removing the hexa-His tag. The expressed protein therefore contained a total of 461 (1+448+6+6) residues (FIG. 1 and SEQ ID NO:5). The synthetic gene thus constructed in pET24d vector was highly and efficiently expressed in E. coli, accounting for about 25% of the total protein (FIG. 2).

Example 3

Fermentation

A frozen stock seed culture of recombinant E. coli harboring the synthetic DNA encoding the LC of BoNT/A was grown at 37° C. to an $OD_{600}$ of 2.682 in a shake flask containing 100 ml of the following defined medium: casamino acids (1.4 g/L); yeast extract (2 g/L); $(NH_4)_2SO_4$ (1.85 g/L); $K_2HPO_4$ (30 g/L); $MgSO_4.7H_2O$ (2 g/L); thiamine.HCl (0.015 g/L); glucose (18.1 g/L); trace elements solution (3 ml/L) consisting of $FeCl_3.6H_2O$, 27 g; $ZnCl_2.4H_2O$, 1.3 g, $CoCl_2.H_2O$, 2 g; $Na_2Mo_4.2H_2O$, 2 g; $CaCl_2.2H_2O$, 1 g; $CuCl_2.2H_2O$, 1 g; $H_3BO_3$, 0.5 g; distilled $H_2O$, 1000 ml; and HCl, 100 ml. In addition, 0.0156 g/L of ZnCl was added to trace minerals to make the concentration of Zn five times greater in the shake flask and fermentor. Kanamycin (50 μg/L) was added as an antibiotic. The shake flask culture was used to inoculate a 5-L BioFlo III fermentor (New Brunswick Scientific, Edison, N.J.) containing 4.3 L of the medium described above. Later in the growth (5.5 hr), 14.1 g/L of casamino acids was added and a glucose feed was initiated to maintain a glucose concentration of 1 g/L. Growth continued for 8 hr until an $OD_{600}$ of 49.9 was reached. Cell induction was then initiated at this time by adding IPTG (final concentration, 1.5 mM). Induction continued for 4 hr after adding IPTG, and cells ($OD_{600}$ of 112.62) were harvested by centrifugation (Beckman, Palo Alto, Calif.) at 7000 rpm for 15 min at 4° C. Cells were washed with cold 0.9% saline and centrifuged at 7000 rpm for min and frozen at −70° C. Wet cell yield was 58 g/L.

Example 4

Extraction and Purification of Light Chain as Inclusion Bodies

In a typical preparation, 12 g of E. coli cells was suspended in a total volume of 30 ml of buffer T containing 5 mM $MgCl_2$, 1.5 mM PMSF, 10 mM β-mercaptoethanol, and 2 mg of DNase. The cell suspension was subjected to 10 cycles of 2-min sonication (at 60% power in a Fisher Model 300 Sonic Dismembrator) and 2-min cooling on ice. After centrifugation for 15 min at 10,000×g, the supernatant was discarded. The pellet was suspended in 30 ml the above buffer. The cycle of sonication and centrifugation was repeated five more times; $MgCl_2$ and DNase were omitted from the buffer during the last two cycles. The resulting pellet contained the rBoNT/A LC, that appeared ~70% pure by SDS PAGE (FIG. 2). The pellet was stored at 4° C. as a white suspension in 15 ml of buffer T containing 1.5 mM PMSF and 10 mM β-mercaptoethanol.

Results

The expressed LC appeared exclusively in the insoluble pellet fraction (FIG. 2). Including $MgCl_2$ and DNase in the cell suspension ensured a clean separation of the pellet from the supernatant after sonication and centrifugation. The white suspension of the purified BoNT/A LC migrated as a 52-kDa band and appeared to be ~70% pure on SDS-PAGE (FIG. 2A), as determined by densitometric analysis. Minor contaminant bands with ~100-kDa, 37-40 kDa, and ~25 kDa also reacted with the antibody in the Western blot (FIG. 2B). While fragments smaller than 50 kDa may have arisen from proteolysis of the LC (DasGupta and Foley, 1989), the origin of the 100-kDa species in the reducing SDS-PAGE gels is not clear since the species also reacts with the affinity-purified antibodies against a small sequence of the LC. Molecular mass determination by MALDI-MS gave 52.774 (±50) kDa as the predominant species along with minor species of 106.028 (±100) kDa and 25.00 (±25) kDa. Amino acid sequence determination of the LC identified V-Q-F-V-N-K-Q (residues 2 to 8 of SEQ ID NO:5) as the amino-terminal sequence, as expected for the constructed gene (FIG. 1) and identical (with the exception of the penultimate valine) to that of the published sequence of BoNT/A (Thompson et al., 1990).

Example 5

Solubilization of the Inclusion Bodies to Obtain Active rBoNT/A LC

In a typical experiment, 0.75 ml of the white rBoNT/A LC suspension (from an equivalent of 600 mg of wet cells) was centrifuged in a 2-ml Eppendorf tube and the supernatant was discarded. The pellet was suspended by mild sonication in 0.9 ml of 50 mM Tris-HCl, pH 9. A 20% solution (0.9 ml) of SKL in water was added to the suspension at room temperature and was mixed by inversion several times. Within 2 min, the pellet became completely soluble. Any remaining turbidity was cleared by further diluting with 50 mM Tris-HCl, pH 9.0, or was removed by centrifugation. The SKL-solubilized LC was dialyzed against 200 volumes of buffer G containing 1 mM DTT with one to two daily changes at 4° C. for 1 week. The yield of the soluble rBoNT/A LC was 12 mg (3.9 mg/ml), which was stored in a glass tube at 4° C.

Results

The purified inclusion bodies were solubilized in 10% SKL and the SKL was removed by dialysis against buffer G containing 1 mM DTT (see Section 2). The use of a 10% SKL solution ensured solubilization within 2 min of incubation, and the LC solution was immediately subjected to extensive dialysis to remove the detergent. Starting with an equivalent of 600 mg of the wet E. coli cells, 12 mg of the soluble LC was obtained, corresponding to 20 mg LC per gram of wet cells. This corresponds to a yield of 1.16 g of the pure protein per liter of cell culture.

Example 6

Properties of the Purified BoNT/A LC

Figures 3, 4:
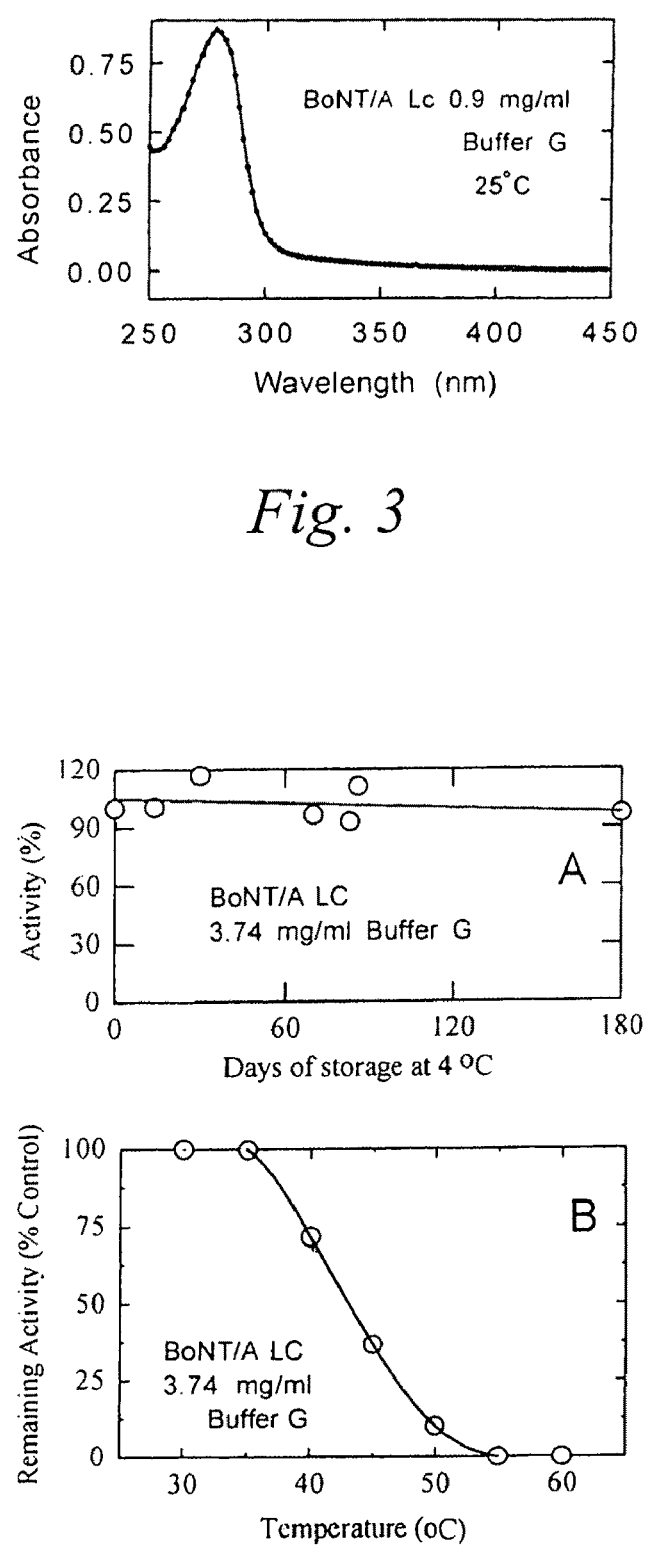

The UV-visible absorption spectrum (FIG. 3) shows the rBoNT/A LC with a single maximum at 278 nm as a simple protein. Although a number of minor band were observed in the SDS-PAGE gel (FIG. 2), absence of any other absorbance bands in the UV-visible range suggests the absence of any nonmetal cofactor in the preparation. The LC was expressed as a C-terminally His-tagged protein. In the presence of 6 M GuHCl, the rBoNT/A LC was bound to Ni-resin and was eluted with imidazole-containing buffers as a more purified form. Without GuHCl, the rBoNT/A LC did not bind to Ni-resin. This result suggests that the LC retained the His-tag after expression and purification, but in the absence of GuHCl, the His-tag was not exposed to solvent to chelate with the Ni-resin. Because the rBoNT/A LC had catalytic properties comparable to those of the dichain (see below), removal of the His-tag from the purified protein was not attempted.

The purified LC was stable for at least 6 months when stored at 4° C. in buffer G containing 1 mM DTT (FIG. 4A). During this period, the protein remained fully soluble, did not show any degradation as analyzed SDS-PAGE, and retained its initial catalytic activity. An LC preparation obtained by prolonged solubilization in 0.5% SKL at room temperature, however, precipitated after 3 months of storage at 4° C. and lost most of its initial catalytic activity. The LC (1 mg/ml of 50 mM Na-phosphate) precipitated from solution below pH 8 either at 4° C. or at 25° C. Thermal stability of the LC (3.74 mg/ml of buffer G containing 1 mM DTT and 50 µM $ZnCl_2$) was investigated by incubating aliquots for 45 min at various temperatures. After cooling on ice for 45 min, the catalytic activities in the supernatants were measured. The midpoint of thermal unfolding $T_m$ as measured by activity was 43° C. (FIG. 4B). At room temperature, increasing concentration of $MgCl_2$ also precipitated the LC from solution: at 6 mM $MgCl_2$, >80% of the LC precipitated.

Example 7

Preparation of Apo-rBoNT/A LC

One milliliter of rBoNT/A LC (2.73 mg) was dialyzed overnight against 250 ml of buffer G containing 5 mM EDTA and 1 mM DTT. EDTA was removed by further dialysis for 60 hr against three changes of 250 ml of buffer G containing 1 mM DTT.

Example 8

Assay of Proteolytic Activity of BoNT/A LC

BoNT/A cleaves the glutamyl-arginine bond between residues 197 and 198 of the 206-residue SNAP-25. Schmidt and Bostian (1995) showed that a synthetic 17-residue peptide representing residues 187-203 of SNAP-25 was sufficient for detecting endopeptidase activity of BONT/A and allowing routine assay for the neurotoxin activity. The peptide thus probably mimics the structure of SNAP-25 in vivo (Bi et al., 1995). The same peptide was used in an identical method to assay the proteolytic activity of the BONT/A LC.

The assay is based on HPLC separation and measurement of the nicked products from a 17-residue C-terminal peptide of SNAP-25 (FIG. 5), corresponding to residues 187-203, which is the minimum length required for BoNT/A proteolytic activity (Schmidt and Bostian, 1995, 1997). Unless otherwise noted, a 0.03-ml assay mixture containing 0.8-1.0 mM substrate, 0.25 mM $ZnCl_2$, 5.0 mM DTT, 50 mM Na-HEPES buffer (pH 7.4), and BONT/A LC was incubated at 37° C. for 15-80 min. The amounts of uncleaved substrate and the products were measured after separation by reverse-phase HPLC (Waters) on a Hi-Pore C18™ column, 0.45×25 cm (Bio-Rad Laboratories, Hercules, Calif.) with the Millenium software (Waters) package. Solvent A was 0.1% TFA and solvent B was 70% acetonitrile/0.1% TFA. The flow rate was 1.0 ml/min at 25° C. After the column was equilibrated with 10% B, the sample was injected, and the column was held at 10% B for 2.5 min. A linear gradient to 36% B over 21 min was followed by 100% B for 6 min. Kinetic parameters for the synthetic substrate were calculated from Lineweaver-Burk plots of activity with peptide concentrations from 0.26 to 1.7 mM.

Catalytic Activity of the LC

Figure 5:
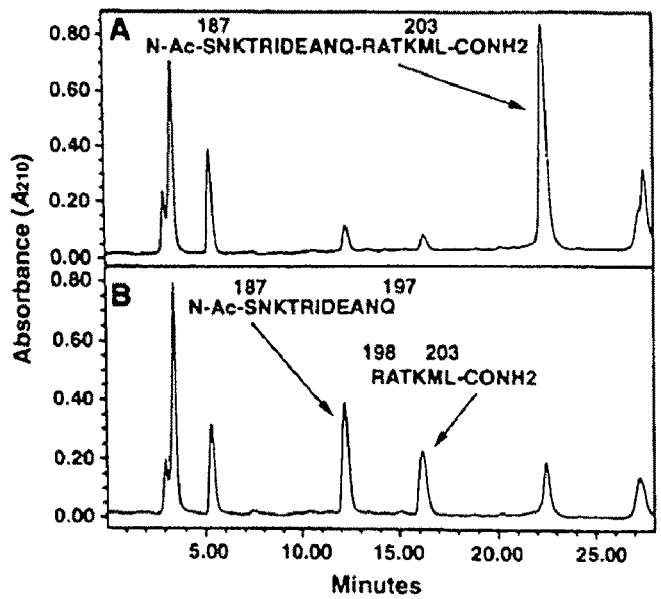
FIG. 5. Proteolysis of the synthetic peptide substrate by the rBoNT/A LC. The peptide (1.1 mM) was incubated for 5 min (A) or 200 min (B) with the rBoNT/A LC. The reaction products were analyzed by reverse-phase HPLC. The first three peaks represent the solvent front (<4 min) and reduced DTT (5.2 min) in the reaction mixture. Sequence of the substrate (SEQ ID NO:2) and the sequences of the products (residues 1 to 11 and residues 12 to 17 of SEQ ID NO:2) are shown in panels A and B, respectively. The numbers above the sequences represent the LC residue numbers corresponding to the sequence of SNAP-25. The product peaks (not labeled in Panel A) were identified by sequence determination by MS-MS.

The BoNT/A LC is zinc-endopeptidase specific for the cleaving the peptide bond between residues 197 (Glu) to and 198 (Arg) of SNAP-25. Incubating the 17-mer synthetic peptide representing residues 187-203 of SNAP-25 with the LC at 37° C. for 5-200 min generated only two peptides (FIG. 5). That no other peptide fragments were generated by this prolonged incubation proves that the contaminants present in the LC preparation were devoid of any proteolytic activity. Incubating the LC with BSA also failed to produce any proteolytic fragment. In contrast to the BoNT/A dichain, whose activity ruin is greatly enhanced by BSA (Schmidt and Bostian, 1997), the rate of cleavage of the synthetic peptide substrate was unaffected by the presence of BSA.

Proteolytic activity of the purified rBoNT/A LC linearly increased with the increasing amount of the LC in the reaction mixture. The time course of activity (at 0.8-1.0 mM substrate concentration), however, was not linear, but progressively declined, possibly due to a high $K_m$ for the substrate peptide (see below). Therefore, routine assays depended on initial activities representing <30% substrate conversion.

Substrate $K_m$ for the LC was fourfold lower than that reported for the dichain (Schmidt and Bostian, 1995). This may be due to shielding of the active site by a 'belt' from the translocation domain ($H_n$) in the dichain neurotoxin (Lacy et al., 1998; Lacy and Stevens, 1999). Thus, the 'belt' may pose a steric hindrance for substrate binding by the dichain (high $K_m$). Nonetheless, the catalytic efficiency $k_{cat}/K_m$ of the free rBoNT/A LC was somewhat higher than that of the dichain.

Optimum pH, Salts, and Buffers

Figure 6:
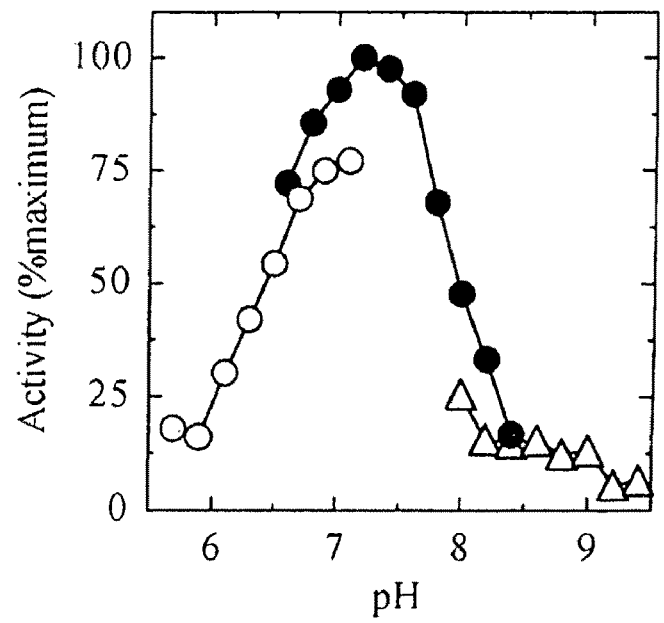
FIG. 6. Effect of pH on the endopeptidase activity of the rBoNT/A LC. Activities were measured at various pH of 0.1 M buffers: MES (-±-), HEPES (-●-), and tris-HCl (-)-) containing 0.9 mM substrate peptide Maximum activity (100%) was 334 nmol/min/mg LC.
Figure 7:
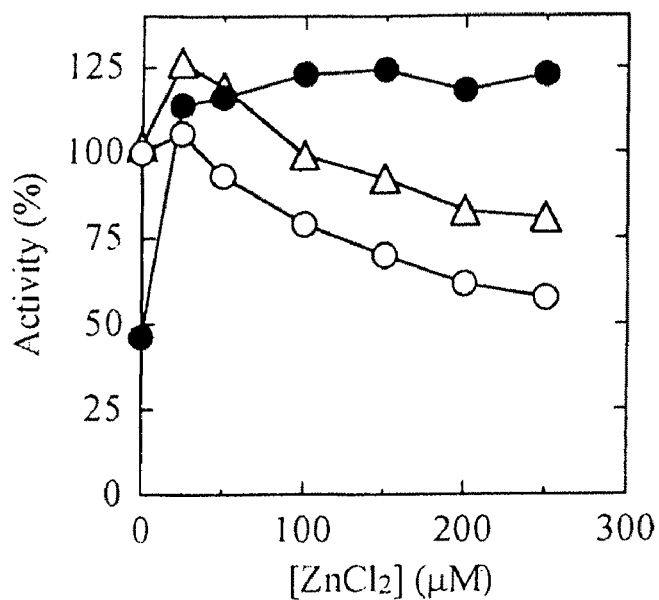
FIG. 7. Inhibition of endopeptidase activity of the rBoNT/A LC by excess $Zn^{2+}$ and protection from inhibition by DTT. The LC was assayed in SO mM HEPES, pH 7.4, containing 0.9 mM substrate peptide in the absence (-±-) and presence of 5 mM DTT (-●-) or 5 mM mercaptoethanol (–)-) containing the indicated concentrations of $ZnCl_2$. One hundred percent activity (290 nmol/min/mg LC) represents the activity obtained in the absence of any added thiol or $Zn^{2+}$.
Figure 8:
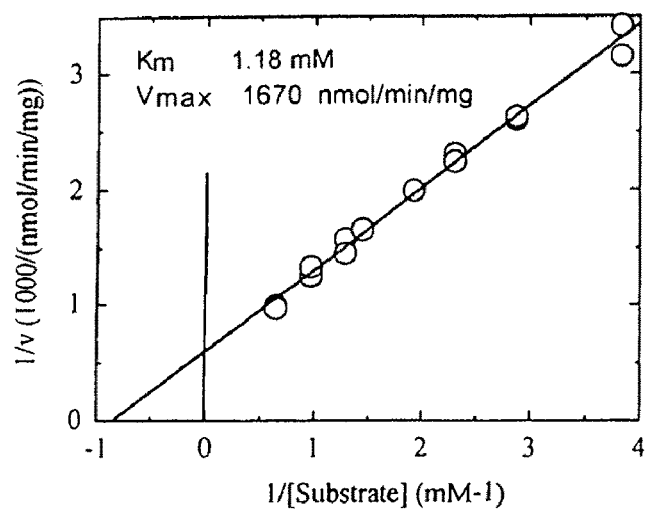
FIG. 8. Determination of $K_m$ and $V_{max}$ from the double-reciprocal (Lineweaver-Burke) plot of initial rates of proteolysis versus substrate concentration by the rBoNT/A LC. The reaction mixtures (0.03 ml) contained 0.25 mM $ZnCl_2$, 0.5 mM DTT, 50 mM HEPES, pH 7.4, and 0.016 mg rBoNT/A LC. The $K_m$ and $V_{max}$ were calculated as 0.9 mM and 1500 nmol/min/mg, respectively.
Figure 9:
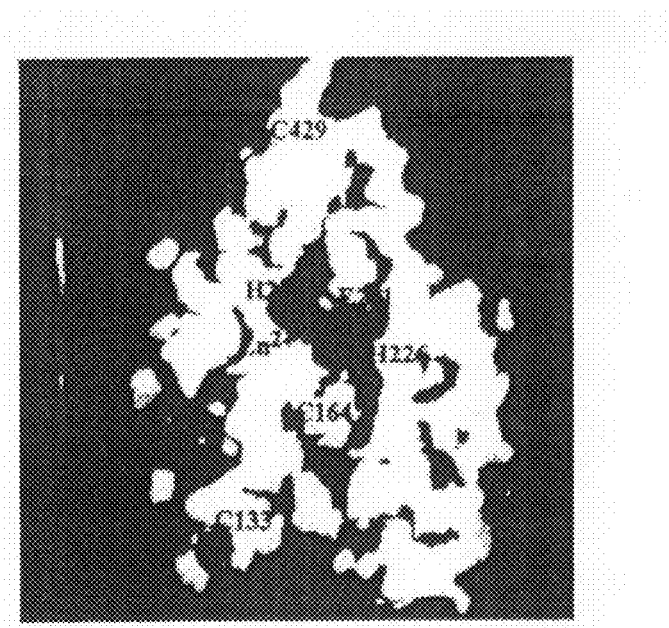
FIG. 9. Location of the three Cys residues in the BoNT/A LC. Molecular surface of the LC portion of the BoNT/A dichain based on its three-dimensional structure (Lacy and Stevens, 1999) is shown. The three Cys residues (yellow), active-site His and asp residues (red), the $Zn^{2+}$ atom (blue) at the active site, and the 'pit' leading to the active site are highlighted. The side chain of Cys-164 lines the surface and forms part of the wall of the 'pit' leading to the active site. The 'pit' acts as an access route of the substrate.

An optimum pH of 7.2 for the proteolysis of the synthetic substrate by the rBoNT/A LC was determined by assaying in three different buffer systems (0.1M) ranging in pH from 5.0 to 9.0 (FIG. 6). For comparison, the optimum pH values of BoNT/B and tetanus neurotoxin, two members of the clostridial neurotoxin family, are 6.5-7.0, and 6.5-7.5, respectively (Foran et al., 1994). Tris-HCl appeared to have an inhibitory effect on proteolysis, presumably due to chelation with the zinc at the active site. The activity at pH 7.4 was 25% higher in a 50 mM HEPES buffer than in 100 mM HEPES. Adding 50 mM NaCl, KCl, or $NaPO_4$ (pH 7.4) to the standard reaction mixture reduced activity 40-50%. Thus, high salt concentrations inhibited the proteolytic reaction.

Effect of Metals and Thiol Reagents on Activity

BoNT/A LC is a zinc-endopeptidase. Activity of the rBoNT/A LC was completely inhibited by including the metal chelator EDTA (1 mM) in the reaction mixture (Table 1). Adding low concentrations of $ZnCl_2$ (1-50 μM) in the assay mixture slightly stimulated the activity (5%-10%) and higher concentrations of $ZnCl_2$ inhibited the activity (FIG. 7). The results suggest that the active site should be almost saturated with $Zn^{2+}$ for optimum activity. The metal was tightly bound to the active site of the LC, as the extraction, purification, or dialysis buffers were devoid of $Zn^{2+}$. Like $Zn^{2+}$, other divalent metal ions, notably, $MnCl_2$ and $NiSO_4$, also inhibited the LC reaction to various extents in the absence of added thiol (Table 1). Adding 5 mM DTT to the reaction mixture neutralized the inhibitory effect of $Zn^{2+}$ (FIG. 7).

Neurotoxic or proteolytic activity of the dichain BONT/A probably requires an initial reduction of the disulfide bond between the LC and the HC (de Paiva et al., 1993). Therefore, the proteolytic assay mixture of BONT/A with the synthetic or natural substrates were supplemented with 5-10 mM DTT (Washbourne et al., 1997; Schmidt and Bostian, 1995, 1997). In the absence of $Zn^{2+}$, 5 mM DTT in the reaction mixture significantly inhibited the activity of the LC (Table 1 and FIG. 7). Similarly, L-cys, dithioerythreitol, and glutathione inhibited the activity to various extents, while β-mercaptoethanol stimulated the activity in the absence of added $Zn^{2+}$. These results were unexpected as the LC does not possess any disulfide bonds and the invariant Cys responsible for the interchain disulfide is far from the active site. One explanation for these effects is the formation of a mixed disulfide between a protein thiol and the exogenous thiol. To investigate the importance of a protein Cys residue on activity, several sulfhydryl reagents were incubated in the proteolytic assay mixture (Table 1). Both $HgCl_2$ and p-Cl-mercuric benzoate completely abolished the activity of LC. Preincubating the LC with these two reagents, then diluting with the proteolytic reaction mixture, also gave the same results. These results suggest the presence of a protein thiol in the vicinity of the active site of the LC.

TABLE 1

Effect of Metal Ions and Thiols and Thiol Reagents on the Activity of the rBoNT/A LC

| Thiol reagent | Concentration (mM) | % Activity | Metal reagent | Concentration (mM) | % Activity |
|---|---|---|---|---|---|
| None[a] | | 100 | EDTA | 1 | 00 |
| Dithiothreitol | 5 | 45 | $ZnCl_2$ | 0.25 | 60 |
| Dithioerythreitol | 5 | 60 | — | 1 | 10 |
| β-Mercaptoethanol | 5 | 120 | — | 0.25 | |
| Glutathione, reduced | 5 | 75 | +Dithiothreitol | 5 | 125 |
| Glutathione, oxidixed | 5 | 75 | $MnCl_2$ | 1 | 40 |
| S-Nitrosoglutathione | 5 | 55 | $MgCl_2$ | 1 | 90 |
| L-Cysteine | 5 | 20 | $CaCl_2$ | 1 | 75 |
| p-C1-Mercuribenzoate | 0.050 | 00 | $FeCl_2$ | 1 | 35 |
| Mercuric chloride | 0.013 | 00 | $CoCl_2$ | 1 | 90 |
| Iodoacetamide | 10 | 80 | $CuSO_4$ | 1 | 95 |
| | | | $NiSO_4$ | 1 | 55 |

[a]The reaction mixture contained only the substrate and the rBoNT/A Lc. Other conditions are as described in Examples 8-20.

Steady-State Kinetic Parameters

The dependence of reaction rates on the substrate concentration was determined at 0.26-1.7 mM substrate at pH 7.4. A double reciprocal plot of the reaction rates versus substrate concentrations (FIG. 8) yielded a $K_m$ of 1.18 mM and a $V_{max}$ of 1670 (equivalent to 2390 considering a 70% pure LC) nmol/min/mg LC ($k_{cat}$=1.39/sec or 1.99 if 70% pure). For comparison, the maximum rate of cleavage of the peptide substrate by the native, dichain toxin is reported to be 1900 nmol/min/mg ($k_{cat}$=4.7/sec), while the $K_m$ is 5 mM (Schmidt and Bostian, 1997). The lower $K_m$ for the LC may be due to a more exposed active site in the free LC than in the LC of the dichain, where the active site is shielded from the solvent by elements of the membrane-spanning domain $H_N$ (28-29). The catalytic efficiency $k_{cat}/K_m$ of the rBoNT/A LC, 1.18 (1.69 if 70% pure), is thus higher than that of the dichain, 0.94 (Schmidt and Bostian, 1995, 1997).

Apo-BoNT/A LC

The rBoNT/A LC was incubated with the metal chelator EDTA and after extensive dialysis, the activity of the apo-BoNT/A LC was measured in the standard reaction mixture. In the absence of any exogenous $Zn^{2+}$ or thiol, the preparation had 17% activity of the holo-BoNT/A LC from which the apoprotein was made (Table 2). This result suggests that the bound $Zn^{2+}$ was not completely removed by the EDTA treatment and dialysis. Nonetheless, adding 5 mM DTT and 250 μM $ZnCl_2$ to the assay mixture restored 70% of the activity of the holo-LC. Moreover, in the presence of 5 mM DTT and 250 μM $MnCl_2$, $MgCl_2$, or $CaCl_2$, 20-30% of the original activity was restored.

TABLE 2

Activities of the Apo-BoNT/A LC With and Without Addition of Divalent Metal Ions to the Reaction Mixtures

| LC form | Divalent metal | % Activity | % Activity recovered[a] |
|---|---|---|---|
| Holo-LC | $+Zn^{2+}$ | 100 | — |
| Apo-LC | +None | 15 | — |
| | $+Zn^{2+}$ | 70 | 65 |

TABLE 2-continued Activities of the Apo-BoNT/A LC With and Without Addition
of Divalent Metal Ions to the Reaction Mixtures

| LC form | Divalent metal | % Activity | % Activity recovered[a] |
|---|---|---|---|
|  | +$Mn^{2+}$ | 20 | 10 |
|  | +$Mg^{2+}$ | 20 | 10 |
|  | +$Ca^{2+}$ | 30 | 20 |
|  | +$Fe^{2+}$ | 0 | — |

[a]Represents percentage of the lost activity of Zn-free apo-rBoNT/A LC that was recovered by adding the indicated metal ions.

Example 9

Vaccination of Animals

Purified rBoNTA LC was tested for its ability to elicit protective immunity in Cr1:CD-1 (ICR) male mice (Charles River) weighing 16-22 g. Two concentrations of recombinant LC (5 and 15 micrograms) with and without adsorption to a 0.2% Alhydrogel (Superfos Biosector, Kvisgaard, Denmark) were administered in 0.9% saline in a total volume of 100 µl. Groups of 10 mice including a naive control (saline alone) received three doses of LC at 0, 2, and 4 weeks. Mice were bled from the retroorbital sinus 12 days postvaccination and their antibodies assayed for titers to toxin. Animals were challenged with native BoNT/A dichain toxin 15 days post-vaccination.

The animal room was maintained at 21±2° C. with a relative humidity 30-70%, a 12/12-hr light/dark cycle with no twilight, and 10-15 air changes/hour. Mice were housed in solid-bottom, polycarbonate Micro-Isolator™ cages (Lab Products, Inc., Seaford, Del.) with paper chip bedding (Alpha-Dri™, Shepherd Specialty Papers, Inc., Kalamazoo, Mich.) and provided food (Harlan Teklad diet No. 7022, NIH-07) and water ad libitum. All procedures were reviewed and approved by the Institutional Animal Care and Use Committee and performed in an AAALAC International-accredited facility in accordance with recommendations in the *Guide for the Care and Use of Laboratory Animals*, 1996 (National Academy Press, National Academy of Sciences, Washington, D.C.).

Example 10

ELISA

Highly purified (>95%) BoNT/A toxin was diluted to 2 ug/ml in phosphate-buffered saline (PBS), pH 7.4 (Sigma Chemical Co., St Louis, Mo.) and was dispensed (100 ul/well) into microtiter plates (Immulon 2, Dynatech Laboratories, Chantilly, Va.). The plates were incubated overnight in a humidity box at 40° C. Five percent skim milk (Difco, Detroit, Mich.) in PBS with 0.01% Thimerosal® was used to block nonspecific binding and as an antibody diluent. The plates were washed with PBS plus 0.1% Tween 20™ between each step. Mouse sera were initially diluted 1:100 and then diluted fourfold for a total of eight dilutions (1:100 to 1:1,600,000). Diluted sera were added in duplicate to toxin-coated wells (100 ul/well). The secondary antibody was horseradish peroxidase-conjugated, goat anti-mouse IgG diluted 1:1000. The primary and secondary antibodies were incubated 90 and 60 min, respectively at 37° C. ABTS substrate (100 ul/well) was added as the color developer. The plates were incubated at room temperature for 30 min. The absorbance was measured with a microplate reader at 405 nm.

A mouse monoclonal antibody, 5BA2.3, was used as the positive control in each assay; naïve mouse serum was added as a negative control in each assay. The titer was defined as the geometric mean of the ELISA titer to BoNT/A toxin.

Example 11

Biological Effects of the RBoNT/A LC

LC prepared from dichain BoNTs always had residual toxicity due to come contaminating dichain forms (Maisey et al., 1988). To demonstrate and confirm that the rBoNT/A LC was nontoxic, 5-15 ug of the LC was injected per mouse, a dose that was 15,000-45,000 times higher than an equivalent lethal dose of the BoNT/A dichain. Table 3 shows that all the mice survived three successive injections. All of their antisera had high titers against BoNT/A, but these antibodies failed to protect the animals upon subsequent challenge with relatively low doses ($10^2$ $LD_{50}$) of the toxic BoNT/A dichain. Even when the ELISA titers were boosted 20-fold by using the aluminum hydroxide adjuvant, the animals were not immune to modes levels of BoNT/A challenge (Table 3). Comparable vaccination with BoNT/A Hc protected animals from challenge with as high as $10^6$ $LD_{50}$ (Smith, 1998). These results clearly demonstrate that the rBoNT/A LC was nontoxic to the animals and confirms earlier observations that LC does not possess any neutralizing epitope(s) (Chen et al., 1997; Dertzbaugh and West, 1996).

TABLE 3

Survival of Mice After Vaccination with the rBoNT/A
LC and Subsequent Challenge by BoNT/A Dichain

| Dose[a] | | Survival at given BoNT/A dichain challenge[c] | |
|---|---|---|---|
| (µg/mouse) | ELISA Titer[b] | $10^2 LD_{50}$ | $10^3 LD_{50}$ |
| 0[d] | <100 | 0/5 | 0/5 |
| 5[d] | 18,000 | 0/10 | 0/10 |
| 15[d] | 63,100 | 0/10 | 0/10 |
| 0[e] | <100 | 0/5 | 0/5 |
| 5[e] | 985 | 0/10 | 0/10 |
| 15[e] | 2800 | 0/10 | 0/10 |

[a]Each mouse was injected at 0,2, and 4 weeks with the indicated dose.
[b]Titer is the reciprocal of the highest dilution with an A405 of greater than 0.2 after background correction. Values are geometric means of the titers of the sera obtained 12 days after final injection.
[c]LD50 is an empirically determined dose of the neurotoxin necessary to cause lethality in 50% of a population of mice.
[d]The LC was adsorbed on Alhydrogel and used as the immunogen.
[e]The LC in saline was used as the immunogen.

Although the LC by itself is nontoxic, in digitonin-permeabilized chromaffin cells (Bittner et al., 1989) and direct microinjection into the cytosol of sea urchin eggs (Bi et al., 1995; Steinhardt et al., 1994), it blocks membrane exocytosis. To demonstrate that the rBoNT/A LC preparation retained this property of inhibiting membrane exocytosis, sea urchin eggs were microinjected with the LC. Eggs of the sea urchin, *Lytechinus pictus*, are an excellent model system for the study of exocytosis. Unfertilized eggs have a layer of vesicles, the cortical granules, docked at the plasma membrane. The SNARE complexes of docked vesicles are inaccessible to the BoNTs. Thus, plasma membrane resealing of the unfertilized sea urchin egg is unaffected by microinjection with botulinum toxins A, B, and C1 (Bi et al., 1995; Steinhardt et al., 1994). Fertilization triggers exocytosis of the cortical granules. After fertilization, the vesicles available for exocytosis are largely undocked and the docking proteins of undocked vesicles are susceptible to proteolysis by injected clostridial neurotoxins.

For fertilized eggs injected with rBoNT/A LC, about 100 min at 20° C. was required to inhibit plasma membrane resealing after mechanical wounding with a glass micropipet. Eggs that successfully resealed showed a transient dye loss for about 1-2 min after micropuncture. Eggs that failed to reseal continuously lost dye and lost control of intracellular free calcium, leading to cell death. Five of five fertilized eggs wounded between 36 and 70 min after injection with the rBoNT/A LC resealed successfully, as did five of five unfertilized injected eggs. Six of six fertilized eggs wounded between 106 and 145 min after injection failed to reseal, indicating that the recombinant light chain actively inhibited exocytosis. Thus, the rBoNT/A LC had a similar effect as BoNT/B in inhibiting membrane exocytosis and resealing of plasma membrane of sea urchin eggs (Steinhardt et al., 1994).

Example 12

Exocytosis Experiments

Plasma membrane resealing after micropuncture with a glass pipette requires calcium-regulated exocytosis (Bi et al., 1995). This exocytosis is dependent on docking proteins (the SNARE complex) that are sensitive to proteolysis by the clostridial neurotoxins (Steinhardt et al., 1994). Sea urchin (*Lytechinus pictus*) eggs were used to test the biological activity of the rBoNT/A LC. The microinjection medium contained 19 volumes of the rBoNT/A LC (3.7 mg/ml) in 45 mM potassium aspartate, 5 mM HEPES, pH 8.1, and one volume of 55 mM fura-2 in 100 mM KCl and 10 mM HEPES, pH 7.1. Injection levels were 5-10% of egg volume. The plasma membrane resealing after micropuncture with a glass pipette was monitored by recording the emission from fura-2 upon excitation at 358 nm (the calcium-insensitive wave-length).

Example 13

Other Analytical Methods

Protein concentration was determined by BCA assay (Pierce) with bovine serum albumin (BSA) as a standard. Reducing SDS-PAGE with 10% tricine-gels (Novex) was according to Laemli (1970). The gels were stained with Coomassie brilliant blue. Western blots were prepared by using a primary polyclonal antibody against a 16-residue N-terminal sequence of BoNT/A LC and a peroxidase-coupled goat anti-rabbit IgG (H+L) as the secondary antibody. Absorption spectrum at 25° C. was recorded in a Hewlett-Packard 8452 diode array spectrophotometer. The N-terminal amino acid sequence of the BONT/A LC was determined by Edman degradation in an Applied Biosystems Procise Sequencer in the 0- to 20-pmol detection range. Molecular mass was determined by MALDI-MS in a PE Biosystems Voyager DE instrument. Sinapinic acid was used as the matrix and the sample was spotted on a stainless steel plate that was not washed with water or TFA. Other conditions in the experiment were accelerating voltage 25,000 V, guide wire voltage 0.3%, and laser 2500.

Example 14

Chemicals, Buffers and Reagents

Buffer P (50 mM Na-phosphate, pH 6.5) was used for Examples 14-20. TPEN and $ZnCl_2$, were from Sigma. Affinity-purified, peroxidase-coupled goat anti-rabbit and anti-mouse IgG (H+L) and ABTS substrate were from Kirkegaard Perry Laboratories (Gaithersburg, Md.). The inhibitor peptide (Ac-CRATKML-$NH_2$) (SEQ ID NO: 46) (Schmidt et al., 1998) was synthesized and purified by Cell Essentials (Boston, Mass.).

Example 15

BoNT/A LC Purification

The rBoNT/A LC was expressed by low-temperature IPTG induction in *E. coli* BL21 (DE3) cells as a soluble protein from a synthetic gene in a pET24a-derived multicopy plasmid (Clontech, Inc.). Construction of the gene and expression of the protein as described (Ahmed and Smith, 2000) was modified as follows: a stop codon replaced the histidine tag at the carboxy terminus of the gene, and induction and expression was at 18° C. for 22-24 hr. The LC was purified to near homogeneity by NaCl gradient elution from each of two successive cation exchange columns (MonoS) in buffer P. A typical preparation had a specific activity of 2-3:mol/min/mg in cleaving the 17-residue substrate peptide when assayed in the presence of 0.25 mM $ZnCl_2$; in the absence of added zinc, activity was 50%. The purified LC was thus partially resolved of the bound zinc. The purified protein (1-4 ml) in buffer P was stored at −20° C. Under this condition, the protein remains stable and retains its catalytic activity for at least 1 year.

Example 16

SDS-PAGE, Transfer on PVDF Membrane, and Western Blot

SDS-PAGE under reducing conditions (Laemmli, 1970) was carried out on a 1-mm-thick 10% tricine gels (Novex) as described (Schagger and von Jagow, 1987). Samples were prepared in 0.4% SDS, 5% Ǝ-mercaptoethanol, 12% glycerol, and 450 mM Tris-HCl, ph 8.45, by boiling for 5 min. The running buffer contained 0.1% SDS in 0.1 M Tris-0.1M Tricine, ph 8.3. The gels were stained with Coomassie Brilliant Blue. Electrophoretic transfer of peptides from SDS-PAGE gels onto PVDF membrane used 10 mM CAPS-NaOH buffer, Ph 11.0, containing 10% methanol as the transfer buffer. Protein bands on the PVDF membranes were visualized by 1 min of staining with Coomassie Brilliant Blue followed by destaining in 10% acetic acid-5% methanol. The stained bands were cut out from the dried membranes for amino-terminal sequence determination. Western blots on nitro-cellulose membranes were prepared using a primary polyclonal antibody against a 16-residue N-terminal sequence of BoNT/A LC and a peroxidase-coupled goat anti-rabbit IgG (H+L) as the secondary antibody (Ahmed and Smith, 2000).

Example 17

Proteolysis Experiments

Before each experiment, aliquots of the protein were thawed to room temperature and were immediately passed through a PD-10 column to remove the EDTA. The protein was collected in buffer P and stored on ice. The EDTA-free BoNT/A LC was mixed with predetermined concentrations of $ZnCl_2$, EDTA, TPEN, or the inhibitor peptide and 20-50:1 was distributed in screw-capped Eppendorf tubes. The tubes were incubated at 4° C. or at 22° C. The final concentration of the protein was 0.18-0.20 mg/ml in these incubation mixtures. At various time intervals an equal volume (20-50:1) of SDS-load buffer was added to a tube for SDS-PAGE analysis.

A 100 mM stock solution of TPEN was prepared in ethanol (95%). Stock solutions of the competitive inhibitor peptide Ac-CRATKML-NH$_2$ (SEQ ID NO: 46) (Schmidt et al., 1998) (5 mM), ZnCl$_2$ (1-4 mM), and EDTA (20 mM) were prepared in buffer P. Unless otherwise mentioned, final concentrations of these reagents in the incubation mixtures with the LC were TPEN 5 mM, EDTA 5 mM, peptide 1 mM, and ZnCl$_2$ 0.25 mM.

Results: Cleavage and Fragmentation of BoNT/A LC

Figure 10:
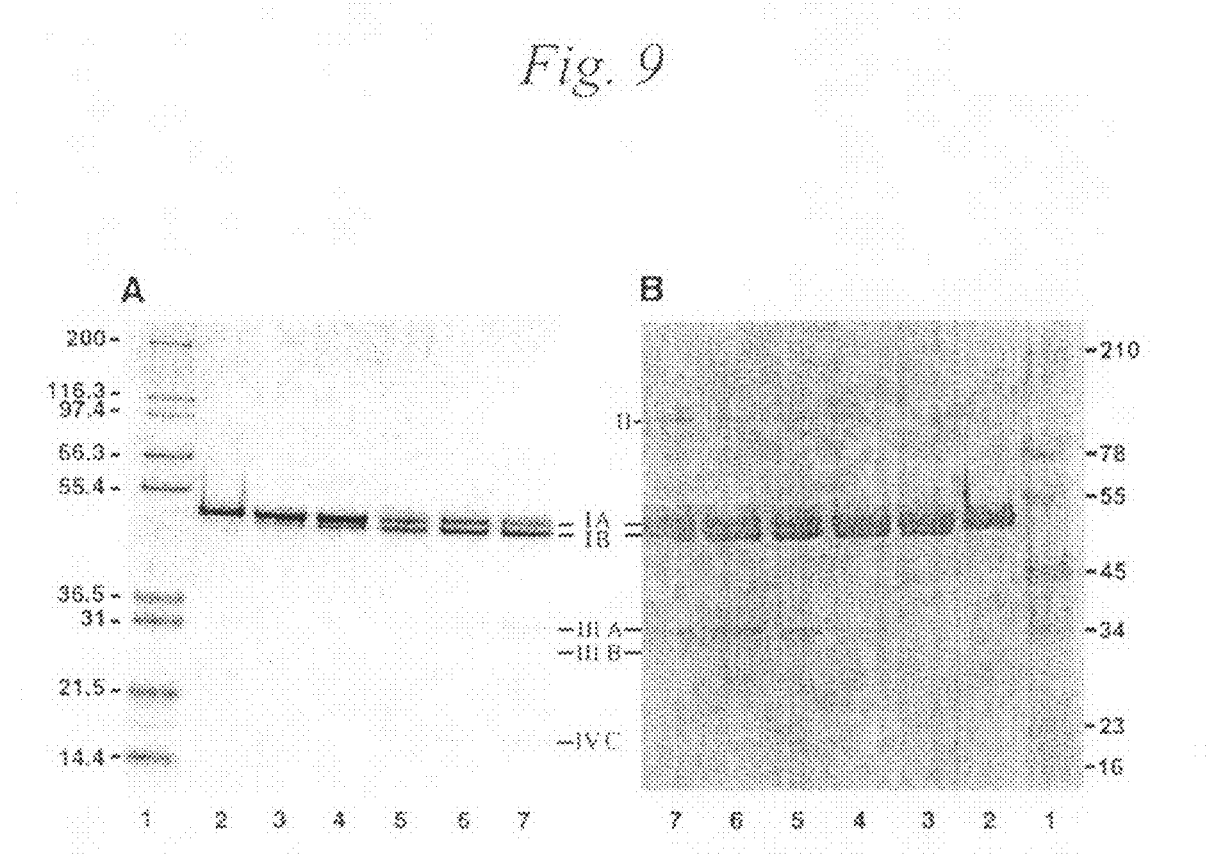
FIG. 10. Time course of proteolysis of BoNT/A LC as followed by SDS-PAGE (A) and Western blot (B). Aliquots of 25 ml of the LC (0.2 mg/ml) were incubated at 4° C. At intervals (see below), 25:1 of 2×SDS-load buffer was added to an aliquot and boiled. Two SDS gels were run in parallel. One gel was stained by Coomassie (A) and the proteins from the other were transferred to a nitrocellulose membrane for Western blot (B). Lane 1 in panel A shows Novex Mark-12 molecular weight markers and lane 1 in panel B shows the Novex prestained SeeBlue molecular weight markers. In both panels A and B, lanes 2-7 show 0, 2, 4, 14, 21, and 28 days of incubation, respectively, of LC. Identity of the protein bands between panels A and B is arbitrary, and the same nomenclature is used throughout the paper.

FIG. 10 shows that the BoNT/A LC undergoes cleavage and fragmentation that increases with time. The intensity of the band representing the full-length LC with a polypeptide mass of ~52 kDa (IA) gradually diminished with time and a new protein band of ~50 kDa (IB) appeared in its place. The results suggest truncation of about 2 kDa mass from the full-length LC. In Western blots (FIG. 10B), both IA and IB also reacted with a rabbit polyclonal antibody raised against a 16-residue amino-terminal sequence of LC. This result suggests that the truncation from the full-length LC must occur at the C-terminus. Indeed, amino-terminal sequencing of the isolated, truncated protein showed the amino terminus was intact. Interestingly, preservation of the N-terminus of full-length BoNT/A neurotoxin was also observed after its post-translation modification in bacterial culture (DasGupta and Dekleva, 1990). As the truncated protein IB accumulated, a protein band of ~100 kDa (II) appeared that was detected easily in the Western blot (FIG. 10B). FIG. 10 also shows that at 2 weeks of incubation, the LC fragmented into IIIA+IIIB and IVC. The larger fragment (IIIA) above the 34-kDa marker was followed by a fainter fragment (IIIB) just below the 34-kDa marker. The results of this time course experiment also suggested that IIIB was formed from IIIA. Both of these fragments must represent the N-terminus of the LC, as they reacted with the antibody (FIG. 10B). On the other hand, a much smaller fragment (IVC) moving faster than the 23-kDa marker was probably the C-terminal fragment, as it failed to react with the antibody (specific for the N-terminus of the LC) in the Western blot. The truncation and fragmentation shown in FIG. 10 were independent of the batch of *E. coli* cell culture or the batch of purification of the LC.

Results: Zinc Accelerates the Truncation and Fragmentation

Figure 11:
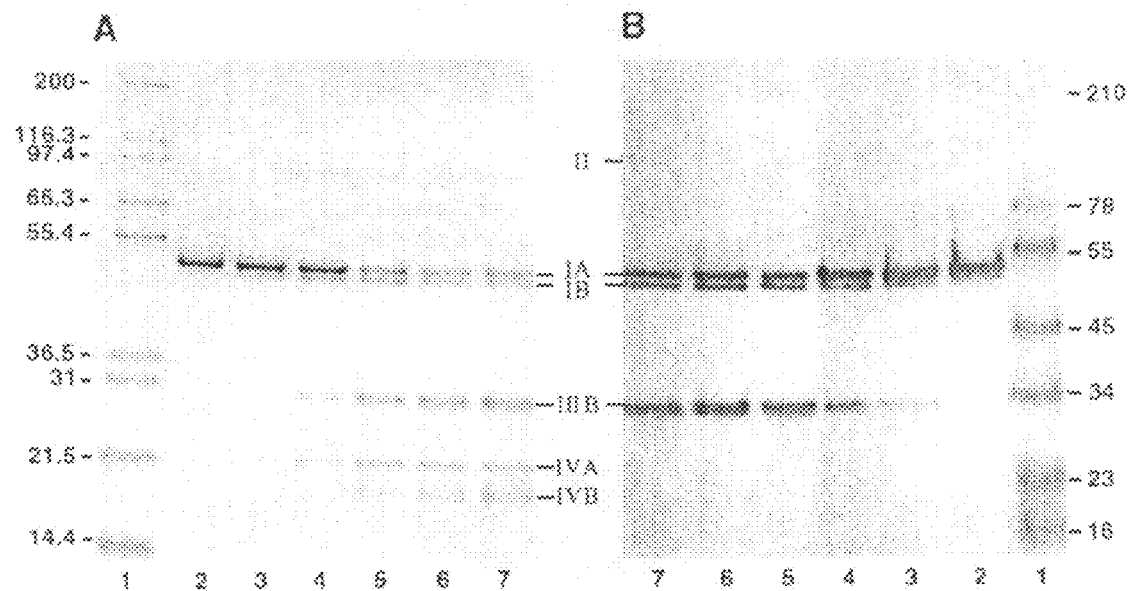
FIG. 11. Enhancement of the proteolysis of BoNT/A LC by $ZnCl_2$ as followed by SDS-PAGE (A) and Western blot (B). All conditions are same as in FIG. 10, except that 0.25 mM $ZnCl_2$ was added to the incubation mixture of the LC.

The BoNT/A LC is known to be highly substrate specific. Therefore, the truncation of about 2 kDa from the C-terminus or fragmentation into larger fragments upon storage of the LC at 4° C. described in FIG. 10 might appear to be due to the presence of some contaminating protease in the LC preparation. However, no additional Coomassie-stained protein bands were detected when 0.4-4.0:g of the LC was electrophoresed in the presence of SDS. BoNT/A LC is a zinc-endopeptidase. FIG. 11 shows that when LC was incubated with 0.25 mM ZnCl$_2$, the rate of fragmentation was greatly increased so that the antibody-reacting fragment IIIB and an antibody-nonreacting fragment IVA appeared within 2 days of incubation (FIGS. 11A, B). Fragment IVB appeared later in the time course. Qualitatively, the results are similar to those in FIG. 10 except that in the presence of ZnCl$_2$, the rate of fragmentation was higher, fragment IIIB was formed without showing the initial formation of IIIA, and initial formation of IVA gave rise to IVB. The rate enhancement by zinc could be partly due to formation of holo-LC from the partially Zn-resolved LC (see Section 2). Because there was no fragment IVC (FIG. 10) detected in this experiment (FIG. 11), zinc must also have a structural role in the LC. From the results shown in FIG. 11A it is not possible to judge if the C-terminal truncation of IA in forming IB and dimerization in forming II precede the fragmentation into III and IV. However, in some other experiments, using a lower concentration of ZnCl$_2$, it was possible to show that formation of IIIB occurred before formation of IB and that fragmentation was the last event.

The rates of C-terminal truncation and fragmentation of LC either in the absence or in the presence of ZnCl$_2$ were much higher when incubated at 22° C. than at 4° C. In fact, amino-terminal sequence was determined on the fragments generated by incubation at 22° C. for 2 days only.

Results: Metal Chelator TPEN Inhibits Truncation and Fragmentation

Figure 12:
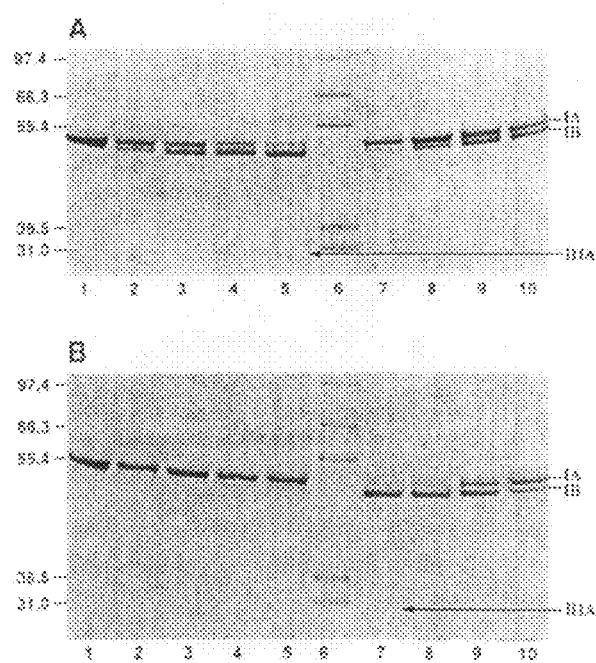
FIG. 12. Protection of BoNT/A LC from proteolysis by the metal chelator TPEN (A) and the competitive peptide inhibitor CRATKML (SEQ ID NO:46) (B), followed as a time course by SDS-PAGE. (A) the LC (0.2 mg/ml) was incubated in small aliquots with 10 mM EDTA (lanes 2-5) or with 5 mM TPEN (lanes 7-10). Lanes 2 and 7, 3 and 8, 4 and 9 and 5 and 10 show 6, 14, 21, and 28 days of incubation, respectively, (B) The LC was incubated with 1 mM peptide inhibitor containing 5 mM DTT (lanes 2-5) or without the peptide inhibitor (lanes 10-7) at 4° C. DTT, which does not have an effect on proteolysis, was added to maintain the peptide in monomer form. Lanes 2 and 10, 3 and 9, 4 and 8, and 5 and 7 show 6, 14, 21 and 28 days of incubation, respectively. In both panels A and B, lane 1 represents LC alone at day 0, and lane 6 has molecular weight markers (labels on left). The protein band IIIA (see FIG. 10) was faint in this experiment and was not captured in the photographic reproduction; therefore its location in the original gel is shown by arrows in the figure. Note that (a) presence (lanes 2-5, A) and absence (lanes 10-7, B) of EDTA had little effect on proteolysis of IA to IB and finally to IIIA, (b) TPEN (lanes 7-10, A) significantly reduced the rate of conversion of IA to IB and prevented formation of IIIA during the course of the experiment, and (c) the peptide inhibitor (lanes 2-5, B) drastically reduced the proteolysis of IA to IB and prevented the formation of IIIA.
Figure 13:
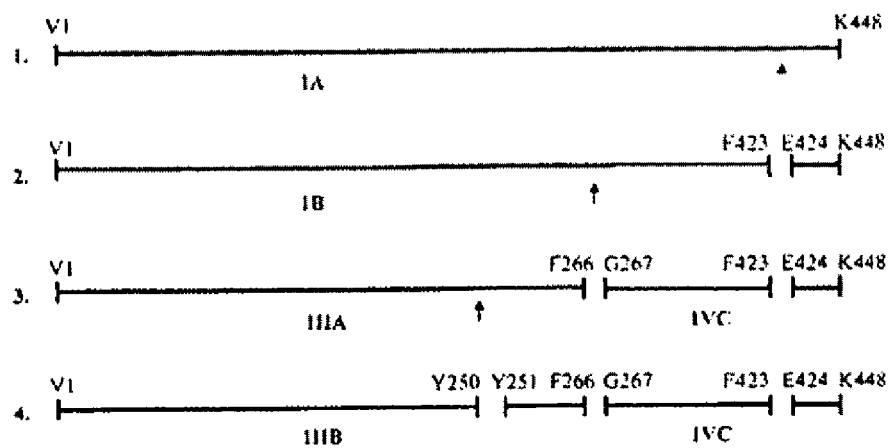
FIG. 13. Scheme I. Steps in the self-proteolysis of BoNT/A LC in the absence of added zinc. Arrows show the sites of proteolysis. Full-length LC is denoted by IA. The fragments IB, IIIB, and IVC correspond to the fragment designations in FIG. 10. The primary event is the C-terminal truncation to form IB followed by cleavage between Y286 and G287 producing IIIA and IVC. The fragment IIIA in turn is further proteolyzed between Y251 and Y252 to generate IIIB. Lengths of the fragments (e.g., IV-K448) are based on mass determined by MALDI-MS and N-terminal amino acid-sequence shown in Table 5. The C-terminal peptide E424-K448, although shown here as a single peptide for convenience, is in fact a mixture of several peptides (see Tables 4 and 5).
Figure 14:
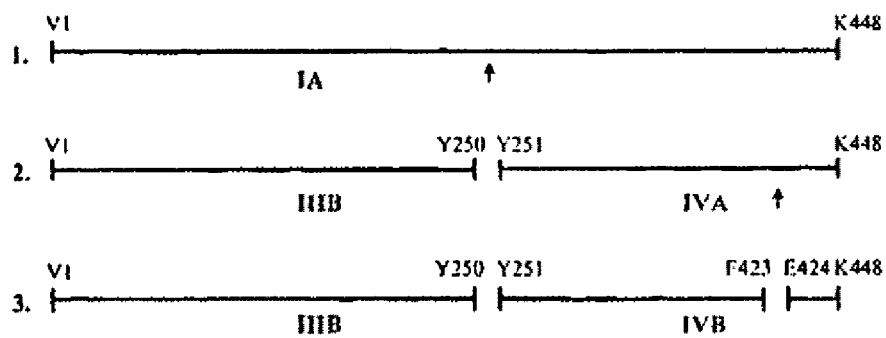
FIG. 14. Scheme II. Steps in the self-proteolysis of BoNT/A LC in the presence of added zinc. Arrows show the sites of proteolysis. The fragments IIIB, IVA, and IVB correspond to the fragment designations in FIG. 2. Unlike the steps shown in Scheme I, IA may bypass the C-terminal truncation and initial formation of IIIA but undergo proteolysis between Y251 and Y252 in directly forming IIIB. The fragment IVA is further cleaved into IVB. Although a C-terminal cleavage of IVB into IVC is possible, it was not observed here (see FIG. 11) this species in the presence of added zinc. See FIG. 11 and Scheme I for other explanations.

As shown in FIG. 11, if the C-terminal truncation and fragmentation of the LC was indeed dependent on the presence of zinc, removing zinc from the incubation mixture and from the active site of the LC would be expected to abolish the truncation and fragmentation events. However, zinc is very tightly bound to the active site of LC. Extensive treatment with 10 mM EDTA in the cold (Ahmed and Smith, 2000) or with 10 mM EDTA at room temperature (Li and Singh, 2000) failed to completely remove zinc from the active site of the LC. In agreement with these observations, including 10 mM EDTA failed to protect the LC from C-terminal truncation and processing (FIG. 12A). In contrast, the metal chelator TPEN largely protected the LC from truncation and fragmentation (FIG. 12A). It was also found that, at 1 mM TPEN, the LC showed no activity when assayed for 5 min. Because the incubation mixture with TPEN did not contain any exogenous metal or zinc, any chelation by TPEN must have involved the active-site zinc of the LC. These results also suggest that truncation and fragmentation of the LC upon storage 4° C. or at room temperature were autocatalytic.

Example 18

Separation of Peptides with HPLC and their Characterization by ESIMS-MS

For mass and sequence determination, peptides were separated on an Agilent Technologies Series 1100 liquid chromatograph with a 0.8×100 mm Poros-2 R/H column (PerSeptive Biosystems, Inc.). The mobile phase was 0.1% formic acid (solvent A) and 80% acetonitrile in 0.1% formic acid (solvent B). The peptides were eluted with a linear gradient of 0-100% B over 15 min at a flow rate of 0.2 ml/min. The injection volume was 10:1. The peptides were detected and structurally characterized on a Finnigan LCQ Deca mass spectrometer employing data-dependent MS/MS. Molecular mass was also determined by MALDI-MS with a PE Biosystems Voyager DE instrument. Sinapinic acid was used as the matrix, and the sample was spotted on a stainless steel plate that was not washed with water or TFA. Other conditions in the experiment were accelerating voltage 25,000 V, guide wire voltage 0.3%, and laser 2500.

Results: Amino Acid Sequence of the Small Peptides Generated by C-Terminal Processing To map the sites of proteolysis, the small peptides were isolated by ultrafiltration of a C-terminally truncated LC mixture. Amino acid sequences of these peptides were determined by ESIMS-MS (Table 4). The peptides with G433 at the amino terminus (peptide 4) and K438 at the carboxy terminus (peptide 5) indicated cleavage by a trypsin-like protease on the R432-G433 and K438-T439 bonds, respectively. Of these, only the lysyl bond at K438 was reported to be cleaved by a clostridial endogenous protease or by trypsin (DasGupta and Dekleva, 1990). However, a cleavage at the K444-G445 bond as reported before by an endogenous clostridial protease (DasGupta and Dekleva, 1990) was not detected. Neither was cleavage detected at K440-S441 or at K427-L428 bonds, the other potential sites of tryptic cleavage. Although these results indicated that the LC preparations did not contain a protease activity that could cleave at K427-L428, K440-S441, and K444-G445, it is equally possible that some of the small peptides generated by cleavage at these sites were lost during sample preparation. Interesting findings of this experiment (Table 4) are the peptides with N-terminus of T420 (peptide 1) and V431 (peptide 3), as the preceding residues at F419-T420 and C430-V431 bonds, respectively, are certainly not the sites of "tryptic" cleavage.

TABLE 4

C-Terminal Peptides Generated after Initial Cleavage of the BoNT/A LC[a]

| Peptide | Mass[b] | 420 425 430 435 440 445<br>KNFTGLFEFYKLLCVRGIITSKTKSLDKGYNK[c] |
|---|---|---|
| 1 | 2188 (2188) | TGLFEFYKLLCVRGIITSK |
| 2 | 2124 (2112)[d] | CVRGIITSKTKSLDKGYNK[d] |
| 3 | 2008 (2008) | VRGIITSKTKSLDKGYNK |
| 4 | 1753 (1753) | GIITSKTKSLDKGYNK |
| 5 | 989 (977)[d] | CVRGIITSK[d] |

[a]The peptides were generated by incubating 0.4 mg of the LC in 0.5 ml of buffer P at 4° C. for 2 weeks. They were isolated by ultrafiltration through a Centricon CM10 (Amicon) membrane that was previously treated with 10 mM EDTA. The filtrate containing the peptides was stored at −20° C. for 1 week before mass and sequence determinations by ESIMS-MS. The sequence on the first row with the numbers above it represents the known C-terminal sequence of the LC (Ahmed and Smith, 2000).

[b]Experimentally determined mass from ESI-MS; calculated mass for the sequence shown is given in parentheses.

[c]Residues 417-448 of SEQ ID NO: 5

[d]The calculated mass was 12.1 Da smaller than the experimental value. Except for cysteine in peptides 2 and 5, the experimentally determined masses of all other amino acid residues agree well with their calculated values. Note that cysteine in peptides 2 and 5 occurred at the N-terminus, but when it was in the middle of the peptide, there was no ambiguity in the results.

The sequence data from the ESIMS-MS results for the peptides 2 and 5 agree very well with the residue stretches V432-K449 and with the residue stretches V432-K449 and with the residue stretches V431-K438, respectively. However the experimentally determined mass for "C430," the residue at the amino side of V431 in both peptides, was greater by 12.1 Dalton than the theoretical mass for cysteine. At this stage, there is some uncertainty regarding the discrepancy in the mass of this "cysteine." Chemical modification experiments using iodoacetamide or acidified methanol failed to shift the masses of these peptides, indicating that the suspected "cysteine" did not have a free sulfhydryl group nor was a contaminating aspartic acid. Cysteine in proteins are known to occur as derivatives such as cysteine sulfenic acids (Ahmed and Claiborne, 1992; Claiborne et al., 1999). Attempts are being made to decipher the chemical nature of this "cysteine." If indeed it was a modified C430, cleavages at the carboxy ends of F419, C430, and V431 in addition to R432, K438, and K438 indicate that the proteolytic activity in this preparation was not "tryptic" in nature, but had a broad specificity.

Results: Identity of the Large Peptides Generated by Fragmentation

The large peptides generated by fragmentation in the middle of the LC were identified by comparing the mass determined by MS with a calculated mass for a stretch of sequence based on the amino-terminal sequence determination (Table 5). Agreements between the experimental and calculated values were within 0.07%. Identity of IIIA as having a sequence range of V1-F266 was based on the kinetics of its (and of IVC's) appearance on SDS-PAGE (FIGS. 10 and 11) and N-terminal sequence of IVC. The sequence data along with Western blot results clearly demonstrated that the amino terminus of the LC (IA and IB) remained unchanged during the prolonged incubation period. Although the C-terminal sequence of the peptides IIIA and IIIB was not determined, N-terminal sequences of the peptides IVA, IVB, and IVC (Table 5) indicate that fragmentation of IA and IB (FIGS. 10 and 11) occurred by cleavage at the Y250-Y251 and F266-G267 bonds. Again, if the cleavages of these tyrosyl and phenylalanyl bonds were catalyzed by a protease, it must have been "nontryptic" in nature. Identity of the peptides IVB and IVC as having F423 at the C-terminal indicated that a C-terminal processing of the LC at F423-E424 remained undetected in the small peptide isolation experiment (see previous section). This result nonetheless supports that C-terminal processing occurred at phenylalanyl bonds in addition to lysyl, arginyl, valyl, and (most likely) cysteinyl bonds.

TABLE 5

Identity of the Polypeptides Generated by Proteolysis of the BoNT/A LC

| Peptide[a] | Mass (Exp) | Mass (Calc) | Sequence range | N-terminal sequence |
|---|---|---|---|---|
| IA | 51,315 | 51,318 | V1-K448 | 2-VQFVNKQ |
| IB | 48,866 | 48,870 | V1-Y426 | 2-VQFVNKQ |
| II | 97,727[b]<br>97,870[b] | | | |
| IIIA | n.d.[c] | 32,270 | VI-F266 | 2-VQFVNKQ |
| IIIB | 28,111 | 28,130 | V1-Y251 | 2-VQFVNKQ |
| IVA | 23,207 | 23,207 | Y252-K448 | 252-YEMSGLE |
| IVB | 20,319 | 20,319 | Y252-F423 | 252-YEMSGLE |
| IVC | 18,400 | 18,400 | G267-F423 | 267-GGHDAKF |

[a]Peptide designations are from FIGS. 10 and 11. Mass was determined by ESIMS-MS. Masses of the peptides IA and IB were determined separately. Peptides were generated by incubating the LC (1.8 mg/ml buffer P) alone or in the presence of 0.25 mM $ZnCl_2$ for 2 days at 22° C. Partial precipitation of the protein was visible after 1 day and was removed by centrifugation before ESI analysis. Masses of IIIB, IVA, and IVB were determined in samples containing ZnCl and those of IA, IB, IIIA, and IVC were determined in samples with no $ZnCl_2$. Calculated masses are for the sequence ranges shown based on N-terminal sequence and mass data. The N-terminal sequences were determined separately for IA (residues 2 to 8 of SEQ ID NO: 5), IB (residues 2 to 8 of SEQ ID NO: 5), and IIIA (residues 2 to 8 of SEQ ID NO: 5) in solutions and for IIIB (residues 2 to 8 of SEQ ID NO: 5), IVA (residues 252 to 258 of SEQ ID NO: 5), IVB (residues 252 to 258 of SEQ ID NO: 5) and IVC (residues 267 to 274 of SEQ ID NO: 5) on PVDF membrane after separation by SDS-PAGE and transfer on membrane.

[b]Data from MALDI-MS determined in a sample containing IB with an initial concentration of 0.2 mg/ml.

[c]Mass could not be detected in several experiments, probably due either to precipitation or to irreversible binding to column resin. Although a peptide with a lower mass can have slower mobility than a homologous higher mass peptide in SDS-PAGE due to charge differences (Ahmed et al., 1986), the kinetics of appearance of IIIB from IIIA (FIG. 1) and their identification by N-terminal sequence determination suggest that IIIA must be larger than IIIB. Identity of IIIA as having a sequence of V 1 -F266 with a mass of 32,270 was based on N-terminal amino acid sequence determination and SDS-PAGE results (FIGS. 10 and 11).

Example 19

Other Analytical Methods

The enzymatic assay was based on HPLC separation and measurement of the nicked products from a 17-residue C-terminal peptide of SNAP-25 corresponding to residues 187-203 (Schmidt and Bostian, 1995). Initially protein concentrations were determined by BCA assay (Pierce) with bovine serum albumin (BSA) as a standard. After it was established by repeated measurements that a 1-mg/ml BoNT/A LC thus determined has $A^{0.1\%}$ (1 cm light path) value of 1.0 at 278 nm (0.98 at 280 nm), protein concentration was determined from absorbance at 278 nm. For comparison, the calculated $A^{0.1\%}$ value of the LC at 280 nm in water (Pace et al., 1995) is 0.948. Absorption spectra were recorded in a Hewlett-Packard 8452 diode array spectrophotometer. The N-terminal amino acid sequence of the LC was determined by Edman degradation in the Applied Biosystems Procise Sequences in the 0- to 20-pmol detection range.

Example 20

A Specific Competitive Inhibitor of LC Activity was an Effective Inhibitor of Truncation and Fragmentation Autocatalytic truncation and fragmentation of proteins can arise from chemical catalysis and from enzymatic catalysis. To differentiate these two possibilities, a peptide specifically synthesized as a competitive inhibitor of BoNT/A proteolytic activity (Schmidt et al., 1998) was used. This peptide inhibitor, with a sequence of CRATKML (SEQ ID. NO:46), competitively inhibits the cleavage of a 17-residue substrate peptide based on SNAP-25 by BoNT/A neurotoxin with a $K_i$ of 2 uM (Schmidt et al., 1998). At a 1 mM inhibitor peptide concentration, the LC showed no activity when assayed for 5 min. FIG. 12B shows that when the LC was incubated with 1 mM peptide inhibitor, both C-terminal truncation and fragmentation at the interior of LC were largely prevented. In the presence of the peptide inhibitor, however, the LC underwent a very slow cleavage, as can be expected in an enzymatic activity with a competitive inhibitor. Densitometric scanning of the gel showed that after 28 days, in the presence of the peptide inhibitor, less than 10% of the LC (IA) was converted into the C-terminally truncated form (IB). In contrast, in the absence of the peptide inhibitor, more than 80% of the LC (IA) was converted into the truncated form (IB). Results of this experiment prove that loss of 10-28 residues from the C-terminus of LC followed by fragmentation into two major peptides (FIGS. 10 and 11, Tables 4 and 5) occurred at the active site of the LC and that these reactions were enzymatic. The results also provide direct evidence that the cleavage reactions were not due to any contaminating protease in the preparation of the LC.

Example 21

Materials

PCR-TOPO and 1-Shot cells were from Invitrogen. pET24a plasmid and BL21 (DE3) cells were obtained from Novagen. All were prepared by standard methods. Proteins were visualized by SDS-PAGE and stained either with Coomassie or Colloidal Coomassie (Novex). Westerns (Novex) were reacted with a rabbit primary antibody (Research Genetics, Inc., Huntsville, Ala.) against the N-terminal 16 amino acids (PFVNKQFNYKDPVNGV; SEQ ID NO:1) of the LC of type A and were visualized with a horseradish peroxidase conjugated goat anti-rabbit secondary anti-body and TMB peroxidase substrate (Kirkegaard Perry Laboratories). Bacterial media was from Difco. Purification of the expressed proteins was on a Pharmacia model 500 FPLC system with programmed elution and $A_{280}$ monitoring (Pharmacia, Uppsala, Sweden). Columns were a Pharmacia HR 10/10 Mono S cation-exchange column, a Pharmacia Mono S 5/5 cation exchange column, and a Perseptive Biosystems POROS 20 HS cation exchange column. Pretreatment of the expressed proteins was with DNase (Sigma, Inc.) and dialysis was with Pierce Slide-A-Lyzer 10 k MWCO cassettes. The SNAP-25 substrate peptide (Quality Controlled Biochemicals, Hopkinton, Mass.) and its cleavage products were separated on a Hi-Pore C18 column, 0.45×25 cm (Bio-Rad Laboratories) and analyzed with the Millennium Software Package (Waters, Inc.). Src (p60c-src) recombinant phosphokinase, substrate peptide, and anti-phosphotyrosine monoclonal antibody 4G10 were from Upstate Biotechnology, Lake Placid, N.Y. [$\gamma$-$^{32}$P]ATP, 3000 Ci/mmol, was from Dupont-NEN.

Example 22

Preparation of Recombinant Neurotoxin Clones

New restriction sites were added by PCR to the 5' and 3' ends (NdeI and HindIII, respectively) of the synthetic DNA molecules coding for the Lc ($M_1$, to $K_{449}$), the Lc plus belt (LC+Belt; $M_1$, to $F_{550}$) and the Lc plus translocation region (LC+Xloc; $M_1$ to $Q_{659}$). These sequences correspond to GenBank accession numbers x, y and z respectively. PCR products were subcloned into pCR-TOPO and the sequences confirmed by DNA sequencing. The inserts were cut from the subcloning vector and ligated behind the NdeI site of pET24a, so as to begin expression with the initial methionine of the LC. The plasmid was transformed into *E. coli* BL21 (DE3) cells for expression.

Example 23

Expression of Neurotoxins

One hundred ml of Terrific Broth (TB) plus kanamycin was inoculated with the appropriate clone and grown overnight, with shaking, at 37° C. Fifty ml of LcA or 100 ml LcA+Belt and Lc+Hn of overnight growth was added to 1 liter TB plus kanamycin and shaking incubation continued at 37° C. for an additional 1.25 hours. While cultures were placed on ice for 5 to 10 minutes, the $OD_{600}$ was read and adjusted to approximately 0.4 to 0.6, then IPTG was added to 1 mM for induction of protein expression. Duplicate cultures were grown at 37° C. (4 hours), 30° C. (10 hours) and 18° C. (22 hours). At harvesting, the $OD_{600}$ was read again, cells were pelleted and frozen at −70° C. if not used immediately. Data points are the mean of three separate measurements of the appropriate bands from SDS-PAGE gels scanned and digitally analyzed with an AlphaImager 2000 densitometer and AlphaImager Documentation and Analysis Software (AlphaInotech, San Leandro, Calif.).

Figure 15A:
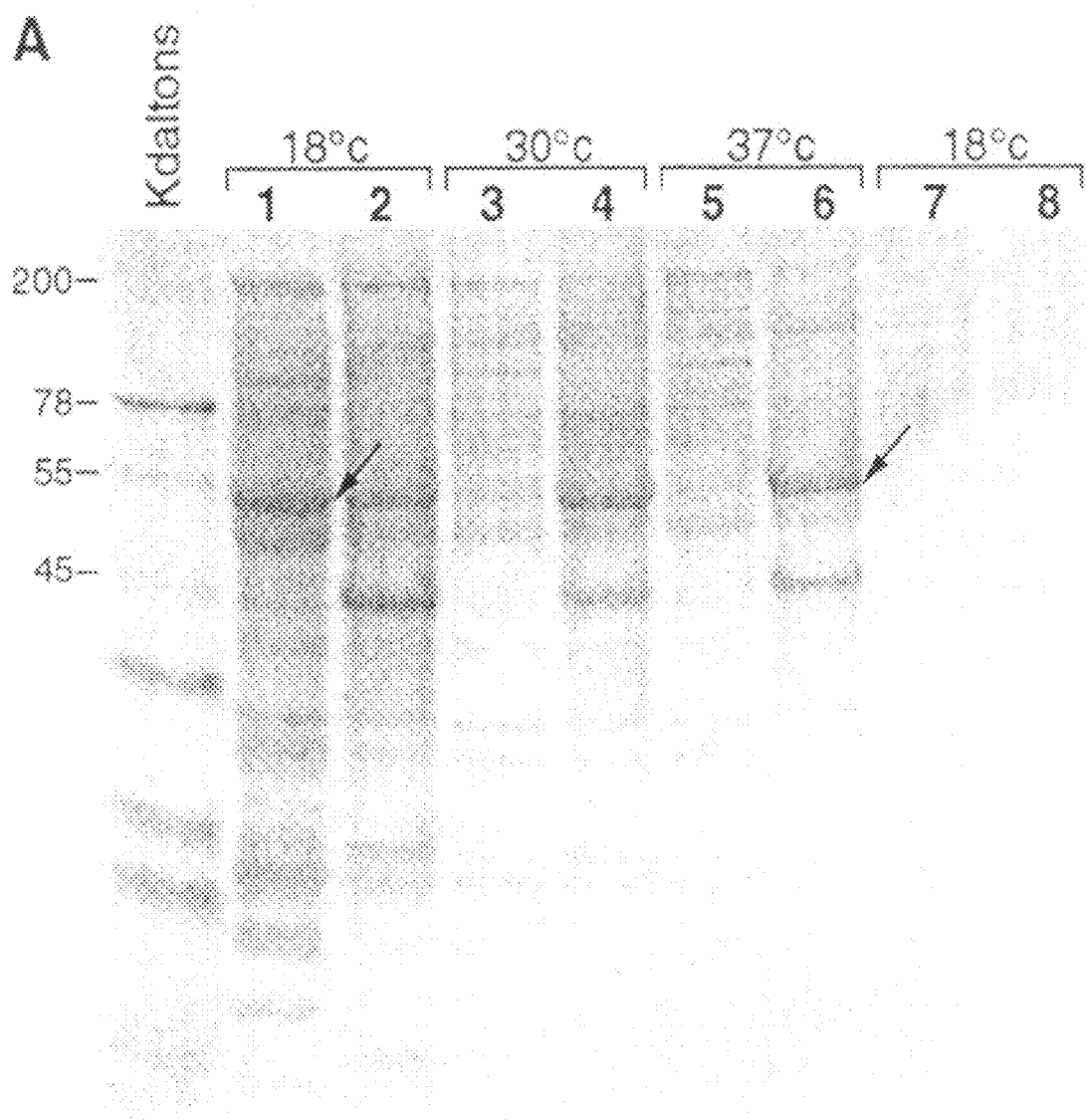
FIG. 15. SDS-PAGE of (A) LCA, (B) LCA+Belt, and (C) LCA+Xloc, expressed at 18° C., 30° C. and 37° C. Odd numbered lanes (1, 3, 5 and 7) are the soluble fractions and even number lanes (2, 4, 6 and 8) are the insoluble fractions. Lanes 7 and 8 are control cells with the plasmid lacking the insert. Arrows show the expressed product at 18° C. (soluble) and 37° C. (insoluble).
Figure 15B:
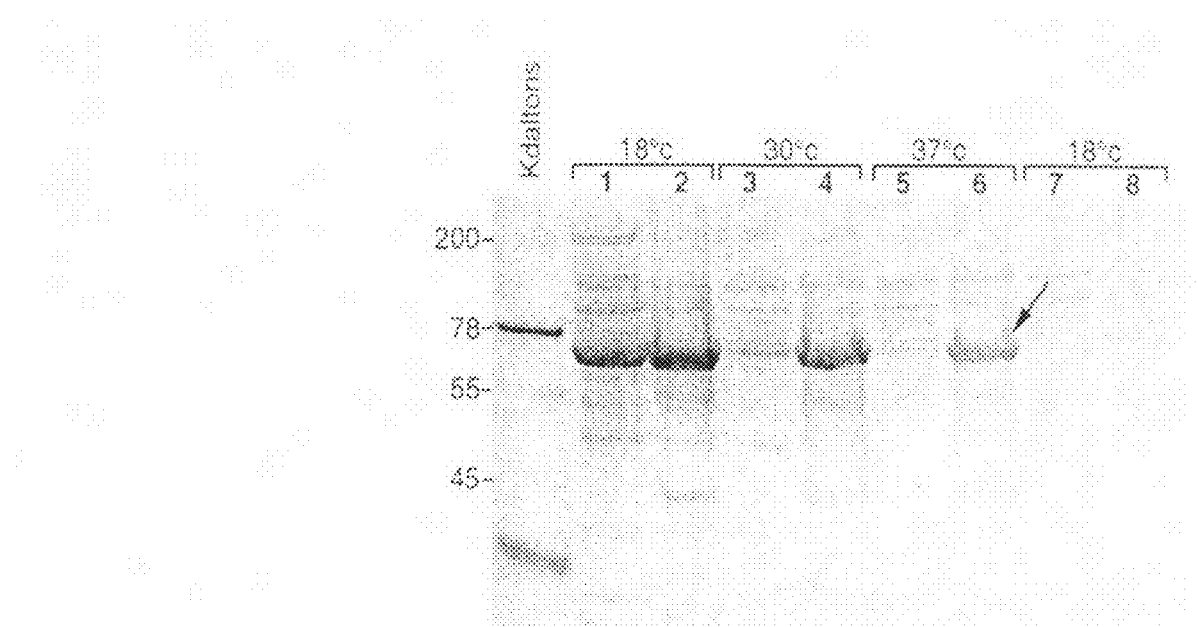
Figure 15C:
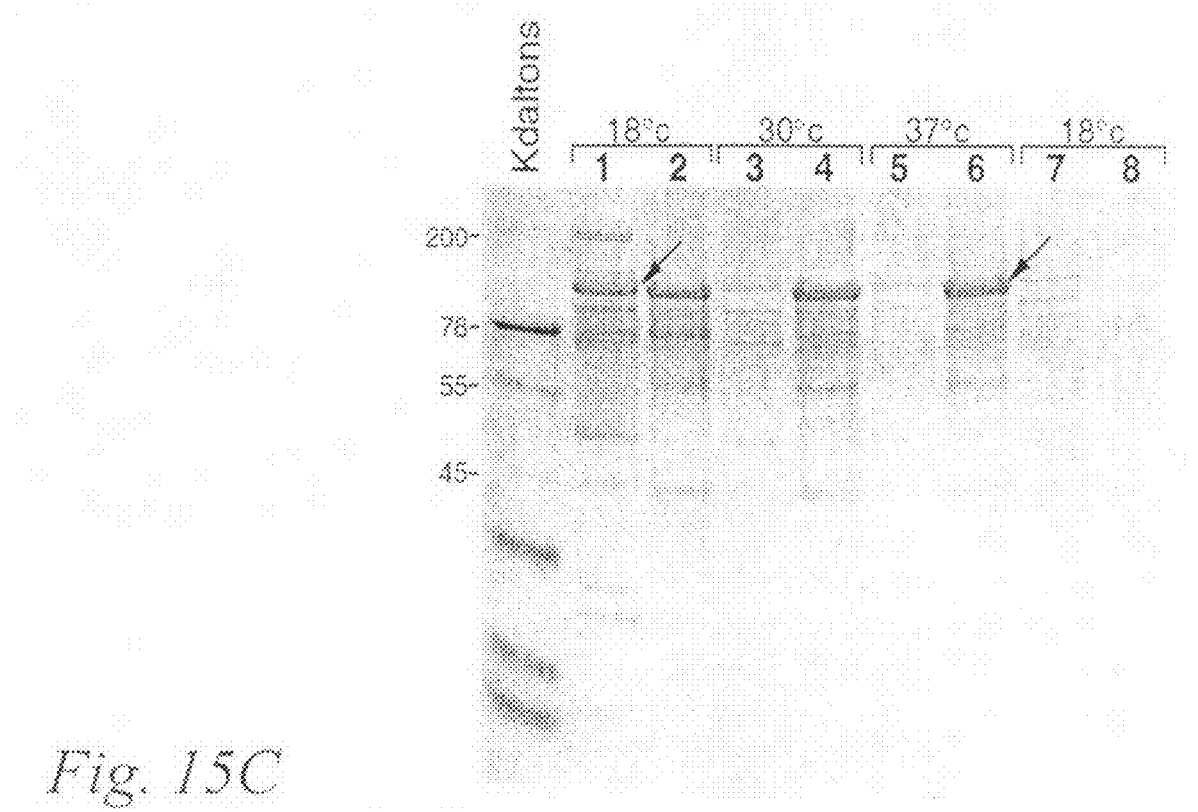

Expression at Low Temperatures Markedly Increases Yields of Soluble Product, while Addition of Portions of the Hn does not Increase the Yield of Soluble Product To study the effects of low temperature induction on the expression of LcA, expression was performed at 18° C., 30° C. and 37° C. FIG. 15A shows the decreasing solubility of LcA at these three temperatures, with concomitant decrease in the soluble product, from 55.5% at 18° C. to 5.2% at 37° C. Yields of soluble LcA were highest at 18° C., with LcA making up approximately 10% of the cell protein. Addition of the belt and Hn portions of the neurotoxin to LcA did not increase solubility (FIGS. 15A, 15B and 15C), although addition of the full Hn region reduced expression and yield (FIG. 15C).

Constructs were grown both in Luria Broth (LB) and Terrific Broth (TB), with no apparent difference in the quality or percent solubility of the products. Total yield was far greater for growth in TB, 17.97 g/l verses 7.77 g/l for LB. Optimal expression conditions for the Lc were considered to be the construct lacking either the belt or the Hn region at 18° C. for 20-24 hours in TB.

Example 24

Sample Preparation and Purification of LC

One gram E. coli cell paste was resuspended into 20 ml of buffer A (20 mM NaAcetate, 2 mM EDTA, pH5.4). The suspended cells were disrupted by sonicating for 12 cycles of 30 seconds followed by 30 seconds of incubation on ice using a medium size probe at 65% output. The resulting cell lysate was centrifuged (Sorval) at 15,000×g for 15 minutes at 4° C. to separate the proteins into soluble and insoluble fractions. The soluble fraction was diluted 1:1 in equilibration buffer B (20 mM NaAcetate, 2 mM EDTA, pH5.8) and used as starting material for the chromatography.

A HR 10/10 Mono S cation-exchange column was extensively cleaned between runs by sequentially running through it: 1 M NaCl through at 3 ml/min for 5 minutes; 20 mM NaOH for 10 minutes at 1 ml/min; 70% ethanol in ddwater for 30 minutes at 1 ml/min; 1 M NaCl in buffer B for 15 minutes at 1 ml/min; then re-equilibrated with buffer B at 2 ml/min for 5 minutes. The diluted lysate was then loaded at a flow rate of 2 ml/min (150 cm/h). The column was washed with 24 ml (3 bed volumes) of buffer B. Flow through and wash were collected separately and stored for subsequent analysis. Protein was eluted from the column with a linear gradient from 0 to 70% 1 M NaCl in buffer B over 8 minutes. Two-ml fractions were collected throughout the gradient. Fractions eluting between 10 and 22 mSiemanns (mS) were positive for rBoN-TA($L_C$) as shown by Western blot analysis. The pooled fractions were diluted 1:3 with buffer C (20 mM NaAcetate, 2 mM EDTA, pH6.2) and loaded onto a Mono S 5/5 cation exchange column equilibrated with buffer C at a flow rate of 2.5 ml/min. The column was washed with 10 ml (10 bed volume) of buffer C. Protein was eluted from the column with a linear gradient of 0-75% 1M NaCl in buffer C over 15 minutes. The rBoNTA($L_C$) protein eluted from the Mono S column as a single band at 12 mS as shown by Western blot analysis. Fractions were pooled and stored frozen at −20° C. in plastic vials. The product was greater than 98% pure as determined by SDS-PAGE.

The LcA+Belt and the LcA+Hn were similarly purified, except that sonication was in buffer A (20 mM NaAcetate, 2 mM EDTA buffer, pH 4.8) and dilution was not necessary after centrifugation to obtain the soluble fraction. After extensive cleaning of the column, the soluble fractions of either LcA+Belt or LcA+Hn were loaded at 2 ml/min onto a Poros 20 HS column equilibrated with buffer A. After loading, the column was rinsed at 3 ml/min with buffer A for 5 minutes and a 5% step of 1 M NaCl in buffer A was performed to remove interfering cellular products. The LcA+Belt was then eluted with a 9% step and the LcA+Hn eluted with a 10-14% step of 1 M NaCl in buffer A. Fractions were pooled, diluted 1:3 with equilibration buffer A and re-run on the HS column, eluting with a 1 to 75% gradient of 1 M NaCl in buffer A. Verification of the peaks was by Western blot and SDS-PAGE. Each protein was 95% or greater pure. Fractions were pooled and stored frozen at −20° C. in plastic vials.

After the first column purification, aliquots of the expressed LcA+Hn were additionally nicked with trypsin at 10 μg/ml overnight, at room temperature. This semi-purified protein lysate was then diluted and run on a second Poros HS column as described above. Protein was similarly 95% or greater pure.

Total protein concentrations were determined by using either a Bio-Rad Protein assay at one-half volume of the standard protocol and bovine serum albumen as the protein standard or the Pierce BCA (bicinchoninic acid) protein assay with the microscale protocol as directed, with bovine serum albumin as the protein standard.

Figure 16A:
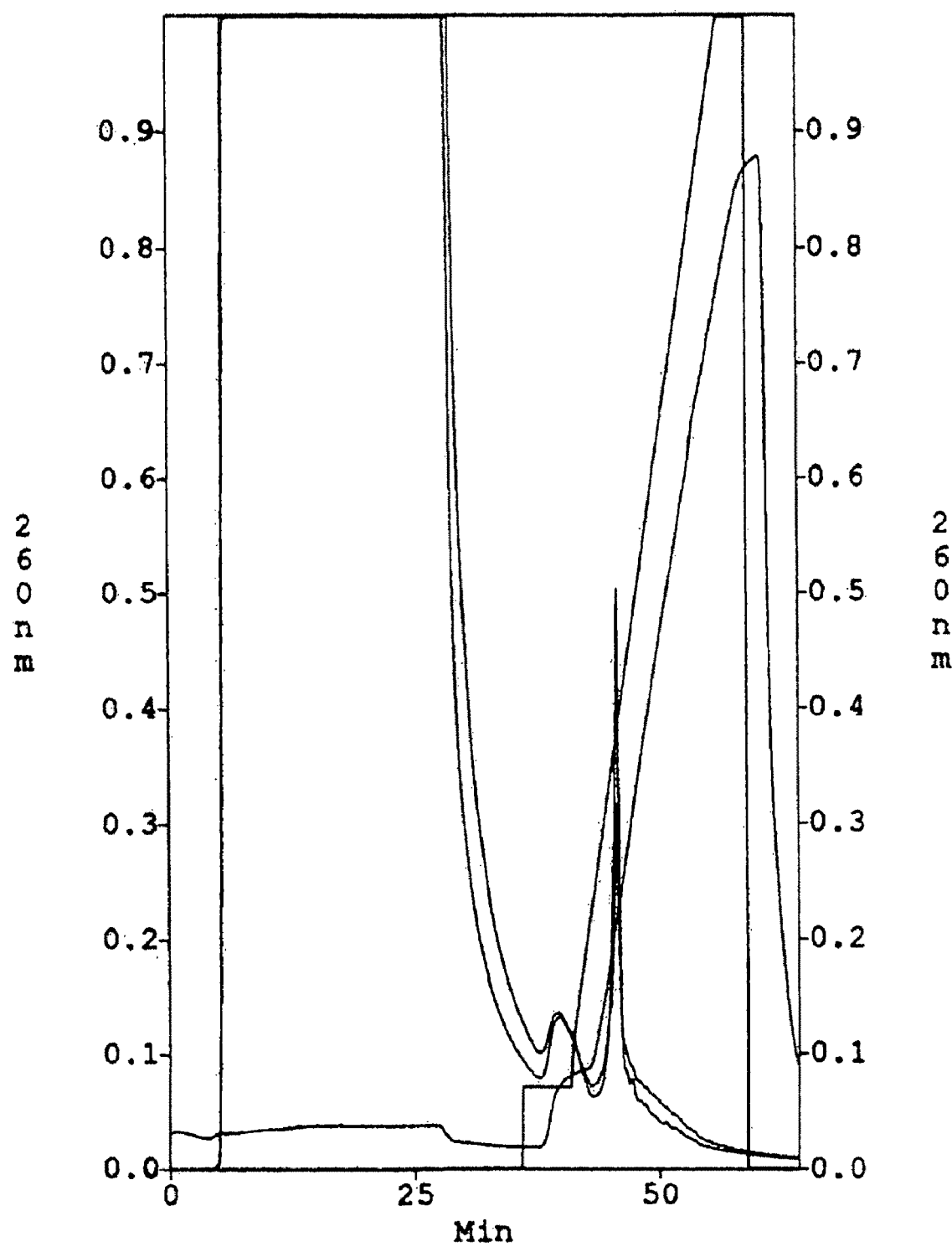
FIG. 16. HPLC elution profiles from HS column of LcA (A, B), LcA+Belt (C, D), LcA+Hn (E, F), and LcB (G, H) and from a Source S column of LcA (I, J).

Purification of the Lc from the Soluble Fraction of the Lowest Temperature Expressed Once conditions had been achieved for optimal yield of product, recovery of the Lc by simple cell sonication was deemed sufficient to release the protein. After removal of insoluble cell debris and proteins by centrifugation, this extract was directly loaded onto a cation exchange column and two isoforms of the Lc were observed to elute between 180 and 280 mM NaCl (FIG. 16A). Western analysis of collected fractions showed two peaks reactive to antisera, corresponding to a full length Lc, and a Lc truncated by approximately 2.5 kDa. Since both forms were reactive to the amino terminus specific sera, a carboxy terminus truncation was indicated. The calculated pI for a Lc lacking the terminal 21 residues is 6.39, suggesting that it would be eluted at a lower NaCl concentration, as was observed. This difference in elution conditions allowed for a separate purification of each Lc isoform. The products eluted from the cation exchange chromatography column were observed to be approximately 70% pure, with a total protein concentration of 1.1 mg/ml.

Figure 16B:
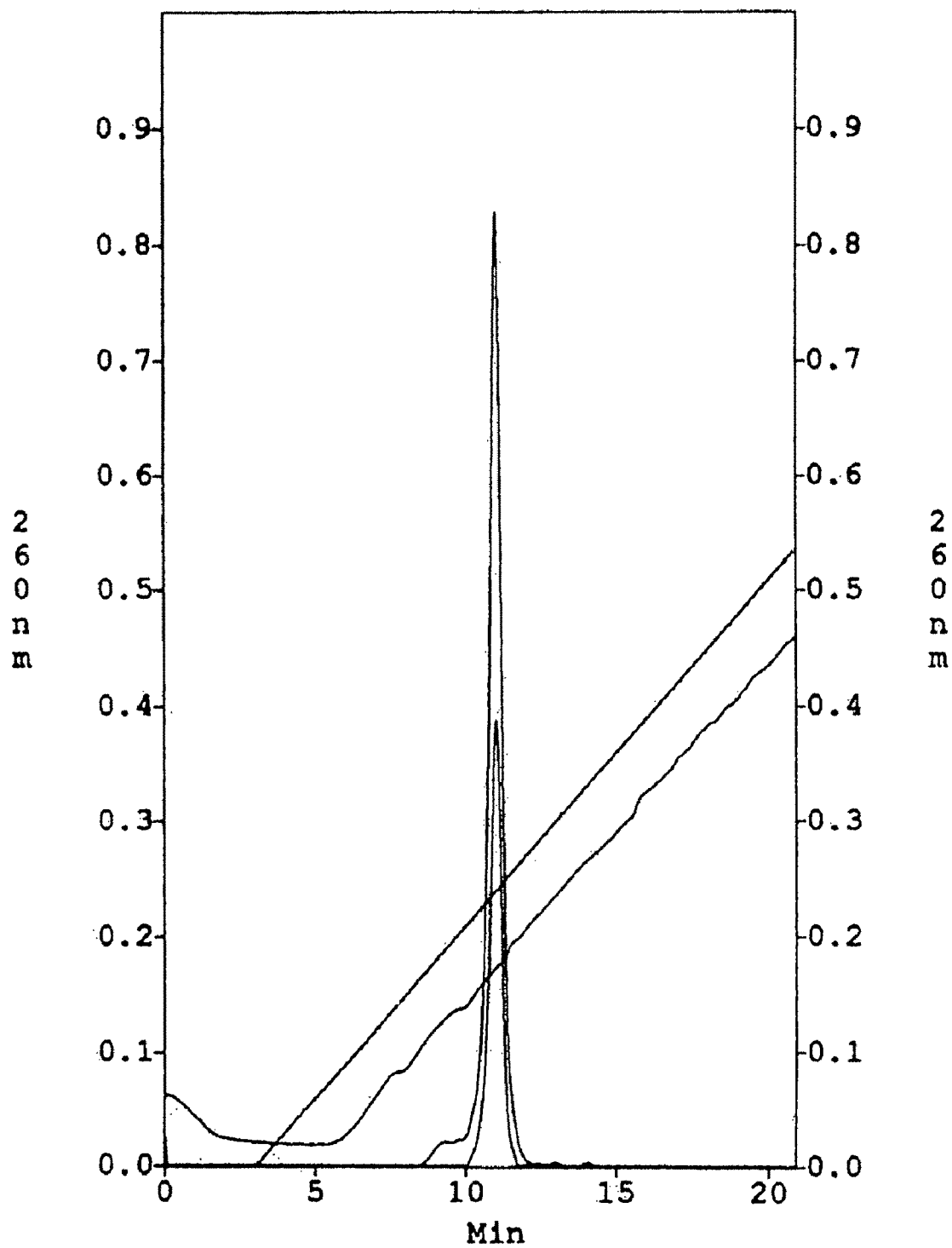
Figure 16C:
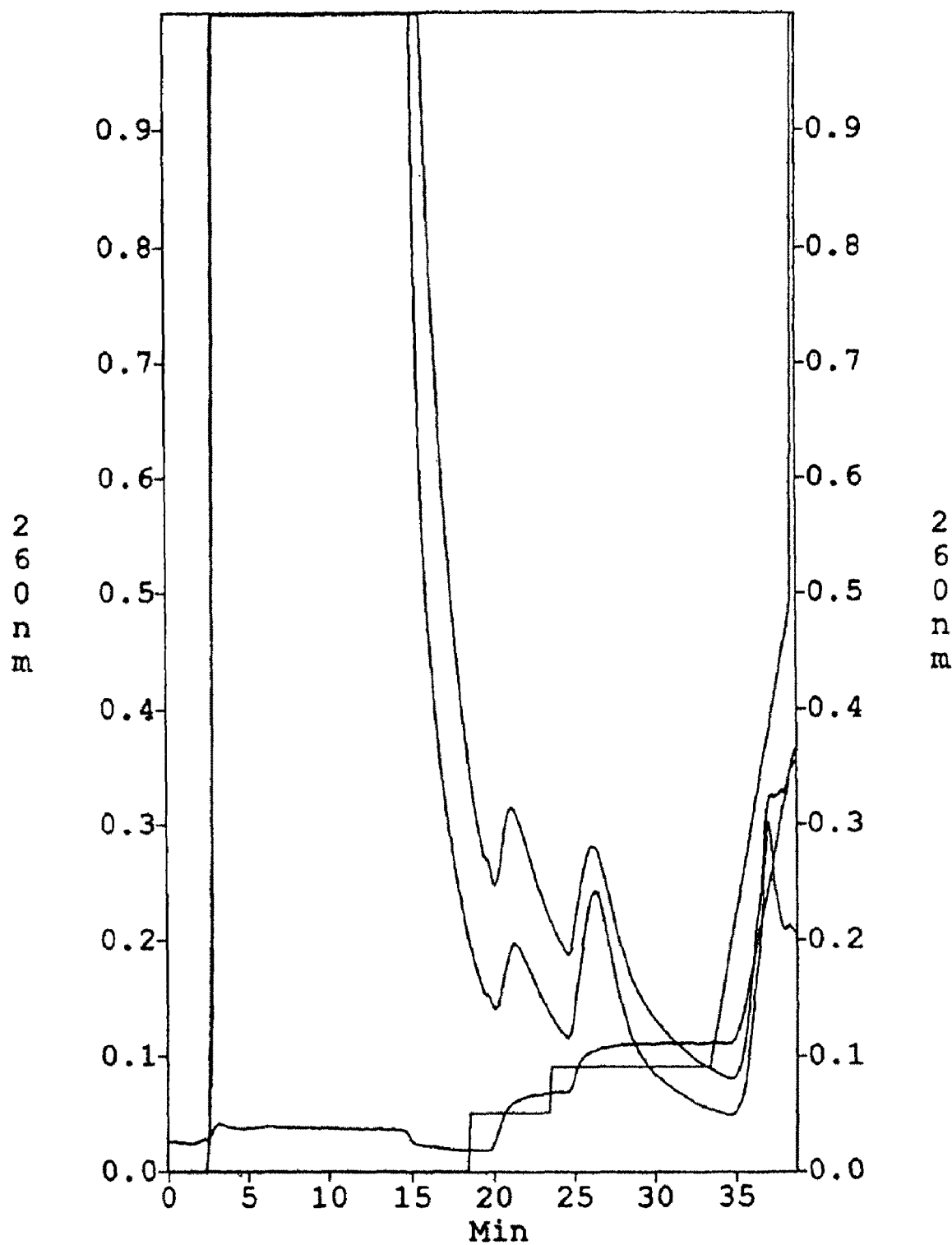
Figure 17A:
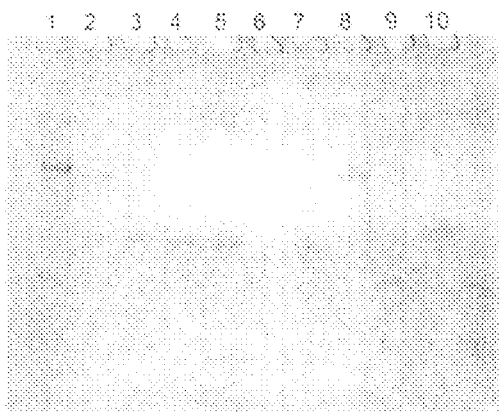
FIG. 17. SDS-PAGE (A) and Western blots of purified LcA constructs using rabbit peptide sera against LcA (B), LcA+Belt (C) and LcA+Hn (D). Lanes from all figures are identical. Lane 1, Novex See Blue prestained molecular weight markers; Lane 2, purified BoNt-A; Lane 3, LcA-HIS; Lane 4, LcA-phosphate buffer; Lane 5, LcA-NaAcetate buffer; Lane 6, LcA+Belt; Lane 7, LcA+Hn, nicked; Lane 8, LcA+Hn, un-nicked; Lane 9, negative control pET24a construct, no insert; Lane 10, LcB.
Figure 17C:
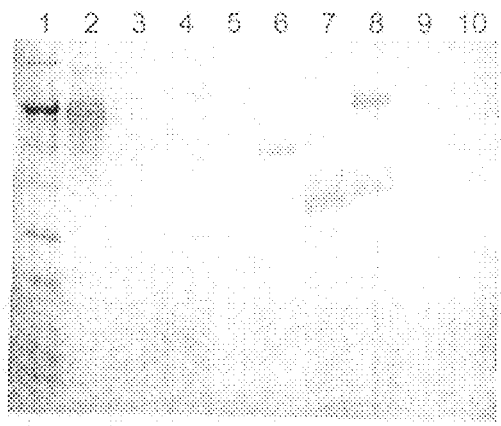
Figure 17B:
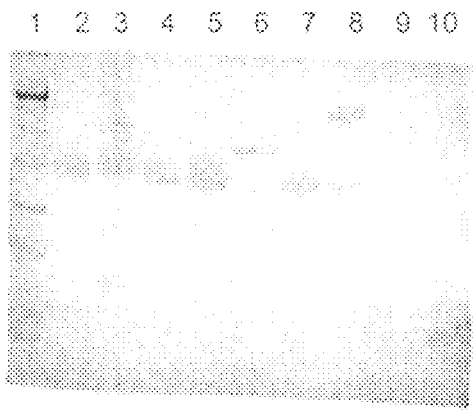
Figure 17D:
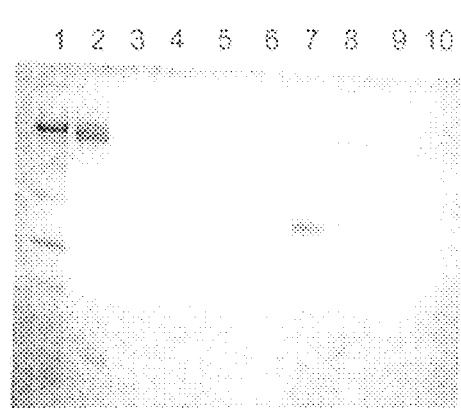

The material was reloaded onto the Mono S column for further purification. The larger, non-truncated, LcA eluted as a single peak at 12 mS (FIG. 16B). SDS-Page and western blot analysis showed only a single band at 51 k-Da (FIGS. 17A and 17B). The product was judged to be 98% pure after the final step and a protein determination determined the overall yield was 0.53 mg purified Lc per gram wet cells obtainable from our protocol.

The LcA+Belt eluted from the first column purification was approximately 85% pure, with a protein concentration of 0.454 mg/ml, in a total of 12 ml (FIG. 2C). After purification on the second column, a 4 ml pooled peak (FIG. 16D) had a concentration of 0.226 mg/ml, with 98% purity, producing a single band as observed by Western analysis (FIGS. 17A and 17C). The overall yield was 0.347 mg/gm wet cells.

Figure 16D:
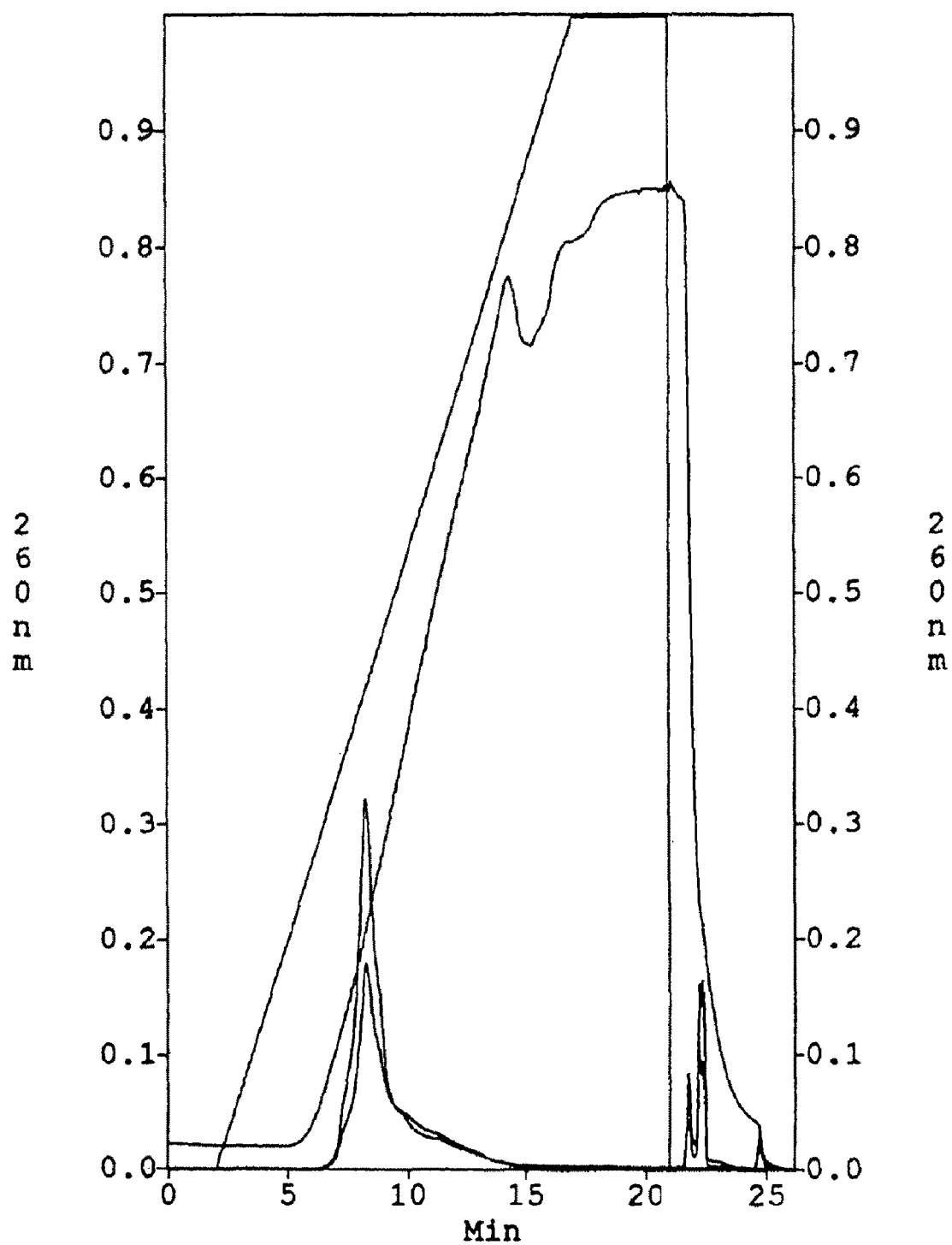
Figure 16E:
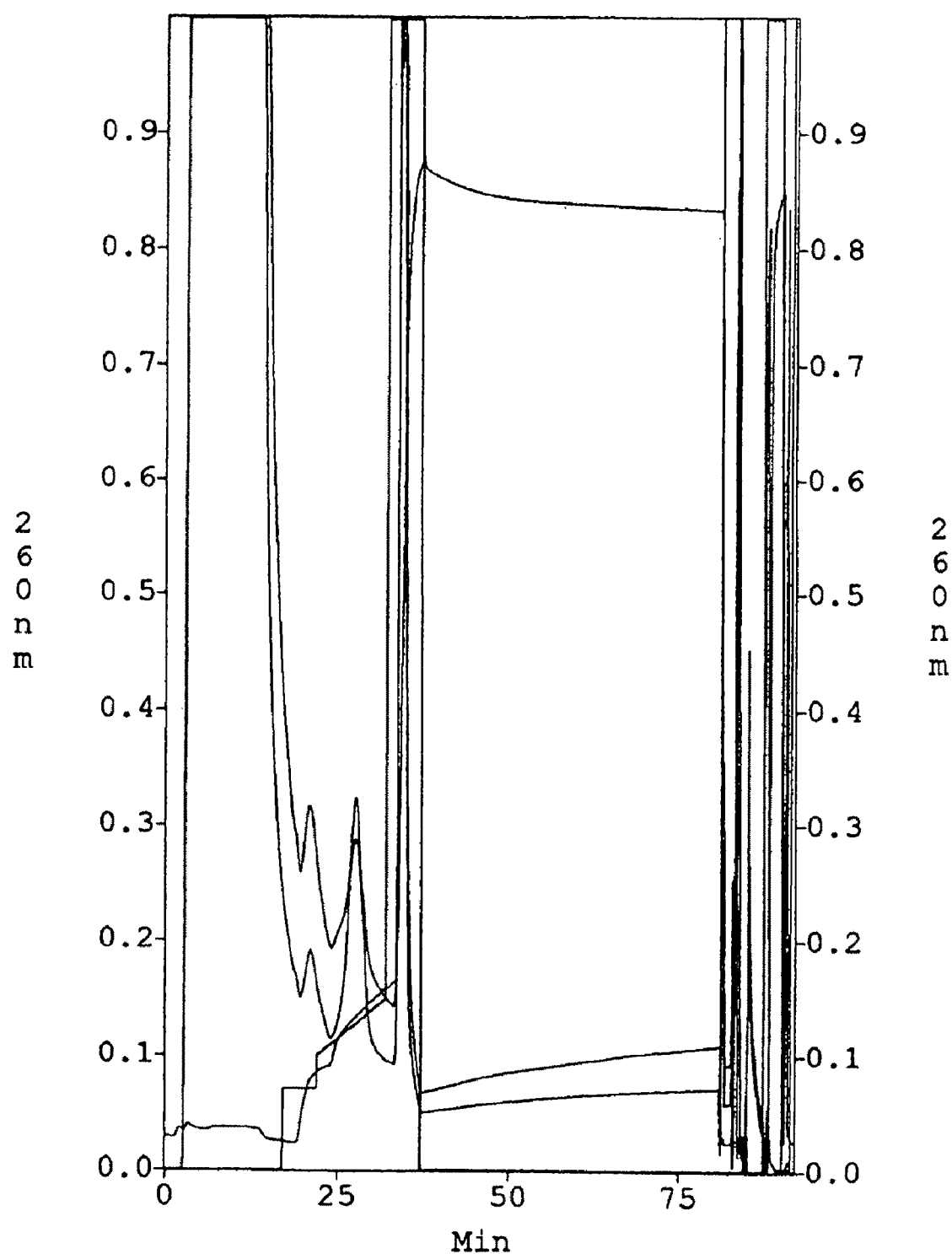
Figure 16F:
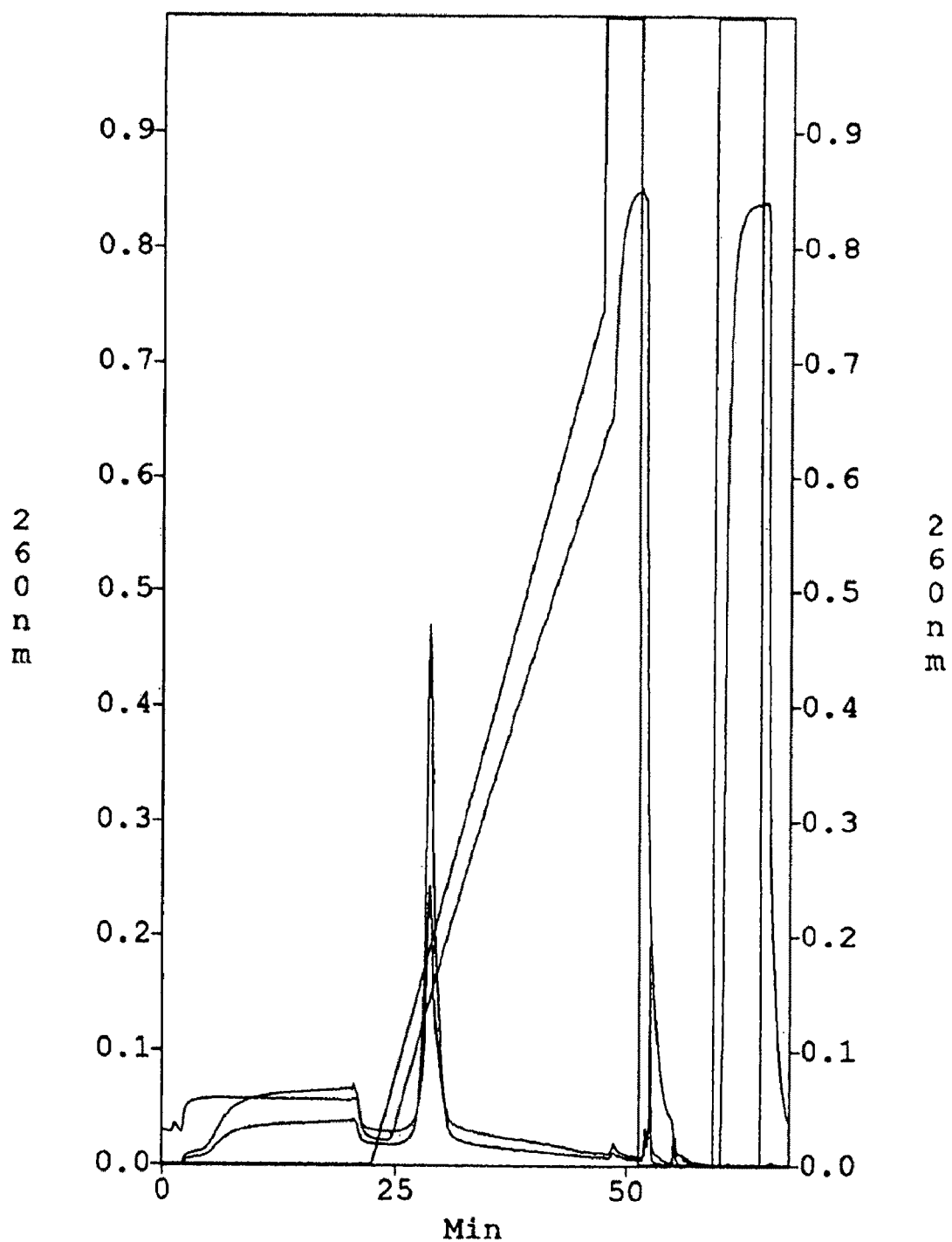
Figure 16G:
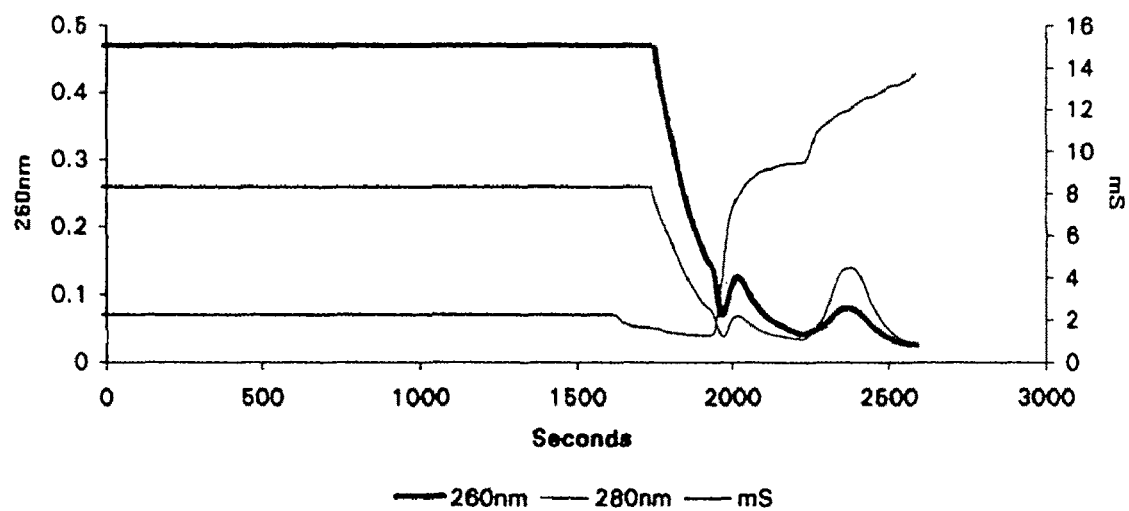
Figure 16H:
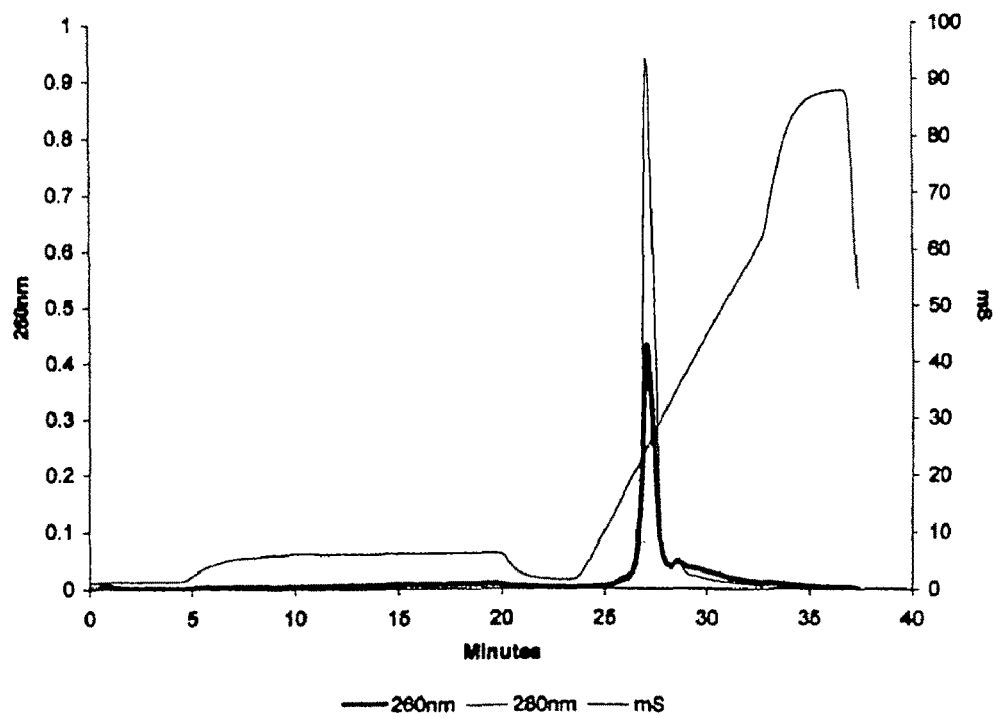
Figure 16I:
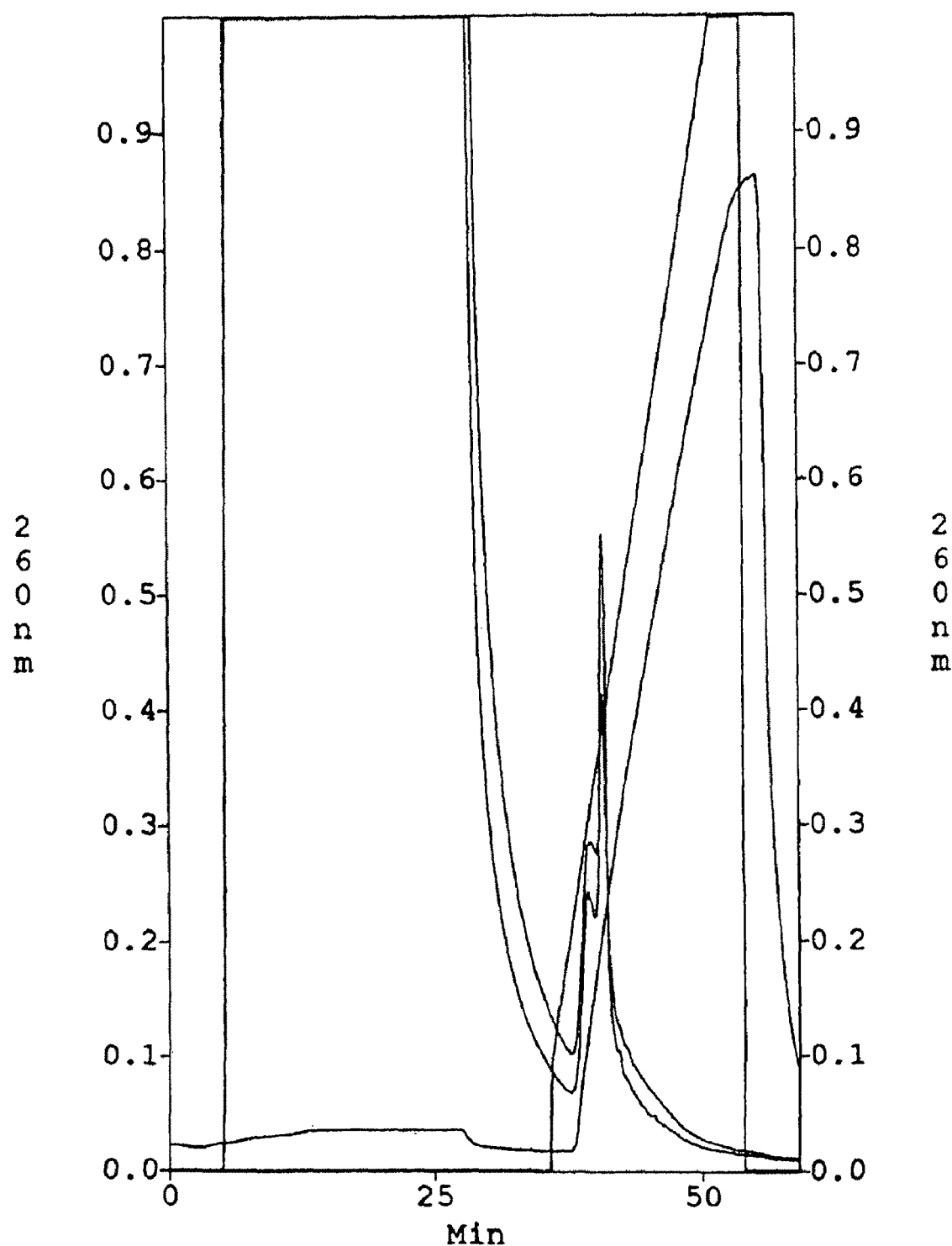
Figure 16J:
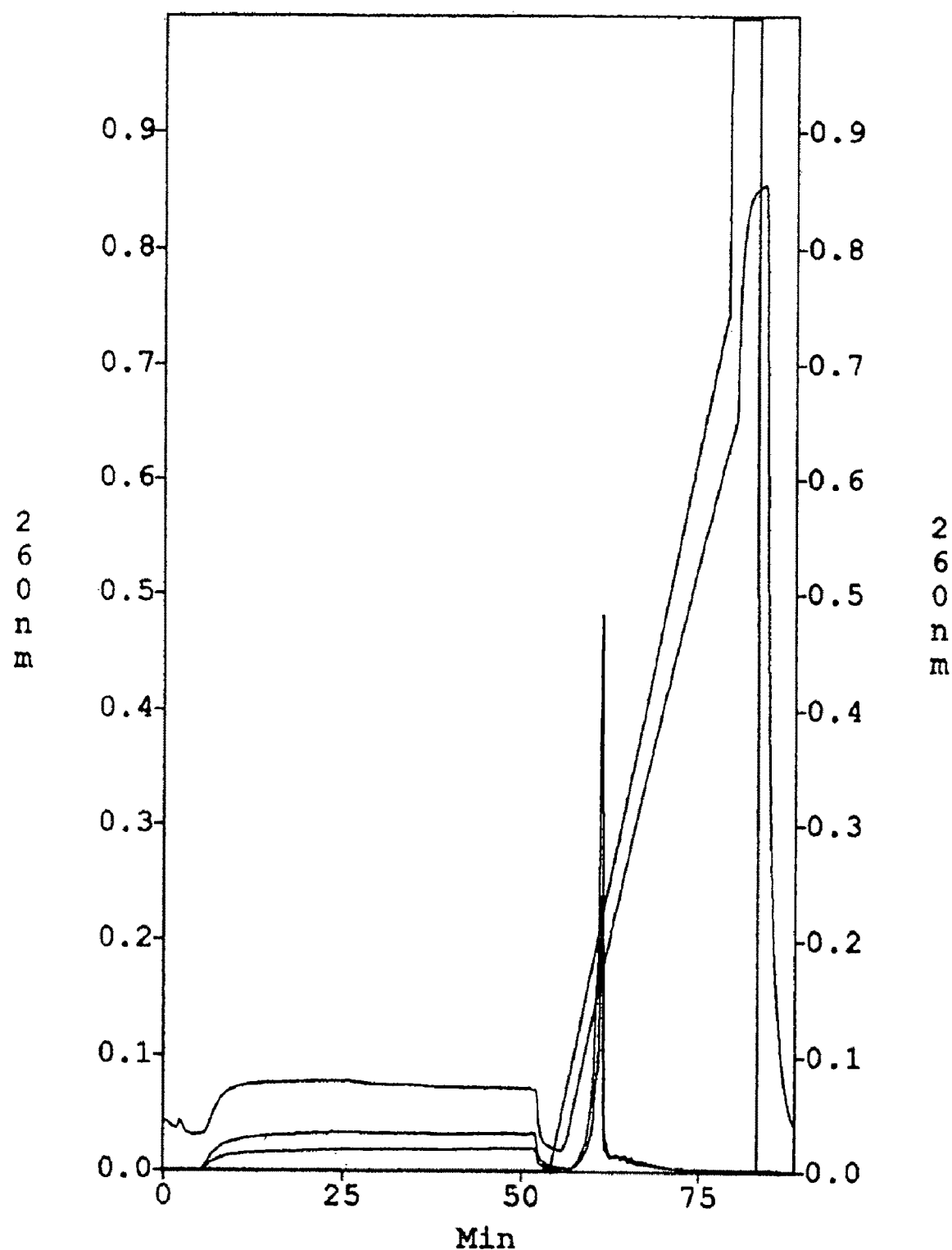

The LcA+Hn eluted from the first column purification was approximately 80% pure, with a protein concentration of 0.816 mg/ml, in a total of 12 ml (FIG. 16D). After purification on the second column, a 4 ml pooled peak (FIG. 16E) had a concentration of 0.401 mg/ml, with 98% purity, forming a single band, while the nicked form of the construct produced two bands (FIGS. 17A through 17D) corresponding to the Hn and Lc. The overall yield was 0.617 mg/gm wet cells.

Example 25

Assay for Cleavage of SNAP-25 Peptide

A 17-residue C-terminal peptide of SNAP-25 (acetyl-SNKTRIDEANQRATKML-amide) (SEQ ID NO:2) shown to be the minimum length required for optimal BoNT/A proteolytic activity (Schmidt and Bostian, 1997) was used as the substrate in a cleavage assay as described previously (Ashraf Ahmed et al.). Briefly, a 0.3 ml mixture containing 0.7-1.0 mM of the substrate peptide, 0.25 mM $ZnCl_2$, 5.0 mM DTT, 50 mM Na-HEPES buffer (pH=7.4) and purified LC (adjusted to produce 10-30% final cleavage) was incubated at 37° C. for 15-180 minutes. The reaction was stopped with 0.09 ml of 0.7% trifluoroacetic acid. Quantitation of cleaved and uncleaved peptide was done by reverse-phase HPLC separation and the fraction of the peptide proteolyzed was calculated by dividing the combined areas of the two cleaved peaks by the sum of the two product and uncleaved substrate peaks.

Catalytic Activity of the Expressed Constructs

Incubation of the 17-mer synthetic peptide representing residues 187-203 of SNAP-25 with the purified Lc at 37° C. generates only two peptides cleaving between residues 197 (glutamine) and 198 (arginine). No other peptide fragments were generated by prolonged incubation, indicating that any contaminants in the Lc preparation lacked proteolytic activity. FPLC purification run #71, which was the complete Lc, resulted in a specific activity of 2.36 μmol/min/mg of Lc. Native BoNT/A in previous assays with the SNAP-25 synthetic peptide had a specific activity of 0.241 μmol/min/mg (Schmidt and Bostian). Thus, the purified Lc produced had a specific activity increased by approximately 10-fold. Run #32 was the Lc+Belt, and had an activity of 0.08 μmol/min/mg.

Example 26

Determination of the Length of the Purified Whole and Truncated Lc

HPLC-purified samples were mixed with sinapinic acid and deposited on a stainless steel target. Mass spectra were acquired with a Perseptive Biosystems Voyager DE MALDI-TOF system. Data were obtained in delayed extraction mode (750 ns delay) with a 337 nm nitrogen laser (3 ns wide pulse), using an acquisition rate of 2 GHz, 50,000 channels, an accelerating voltage of 25000, 93% grid voltage, and a 0.3% guide wire voltage. Typically, 128 scans were averaged. The mass spectrometer was externally calibrated with myoglobin and bovine serum albumin.

The amino-terminal sequence of the expressed Lc was determined by automated Edman degradation performed on an Applied Biosystems Procise Sequencer (Applied Biosystems, Foster City, Calif.) in the 0-20 picomole detection range.

Determination of the Cleavage Point for Purified Lc

Purified Lc kept at −20° C. in purification buffer with 2 mM EDTA had no observable cleavage or truncation products. When the same product was placed at 30° C. for 1 hour, the truncated Lc seen after the first cation exchange column passage was observed. In a mass spectrum for cleaved BoNT/A Lc, the ion at m/z 49039.0 corresponds to the singly-charged molecule, whereas ions at m/z 24,556.9, and 98,280 correspond to doubly-charged and dimer species, respectively. The verified amino terminus for the Lc was VQFVNKQFNY (residues 2 to 11 of SEQ ID NO:5), with the terminal methione removed, resulting in a peptide of 448 residues. The observed principal mass of 49,039 is approximately 2279 daltons less than the calculated mass for type A Lc, which represents a loss of 21-22 amino acids. Since the amino terminus specific antibody still reacts with the truncated molecule, cleavage occurred near the C terminus of the molecule. Because of mass uncertainty with MALDI-TOFMS (0.05% maximum mass accuracy for this instrument), it was not possible to positively identify the site of cleavage. Nevertheless, it was determined that cleavage occurred at either $Y_{426}$, $K_{427}$, or $L_{428}$. The most probable site of cleavage was between $K_{427}$ and $L_{428}$. Calculated mass for that product was 48,999, a difference of 40 daltons, which represents the best match to the observed ion and a mass accuracy to within 0.08%.

Addition of $MgCl_2$ to 125 mM and incubation for 1 hour at 30° C. resulted in two cleavage products after the Lc had lost the carboxy terminal residues. Amino terminus sequencing showed the cleavage to be between two tyrosines, $Y_{250}$ and $Y_{251}$.

Example 27

Phosphorylation of Purified Lc

Phosphorylation was at 30° C. for 1 to 24 hours in a final reaction volume of 40 μL with 30 units c-src kinase. Non-phosphorylated samples were those in which enzyme was omitted. The amount of Lc in the reaction was from 6.25 nM to 1.25 nM. The 4× buffer used for the reaction consisted of 100 mM Tris-HCl, pH 7.2, 125 mM MgClz, 25 mM MnCl2, 2 mM EGTA, and 2 mM DTT. ATP was at either 500 μM or 1 mM, with [(-$^{32}$P]ATP added to a final concentration of 1 μCi/ul. In some cases, substrate peptide (KVEKIGEGTGVVYK; SEQ ID NO:3) at 93 μM was substituted for the Lc to act as a control. Reactions were stopped by freezing at −20° C. Phosphorylated samples were run on SDS-PAGE gels, and either blotted and bands visualized with an antibody specific to phosphorylated tyrosine or the amino terminus of the Lc, or they were stained with Coomassie Blue, destained, dried and exposed to Kodak BioMax Light film.

Phosphorylation of Lc

Purified Lc that was tyrosine phosphorylated resisted cleavage at the $Y_{250}$-$Y_{251}$ site. During the initial 1 hour period of phosphorylation, the characteristic cleavage products were observed, but did not substantially increase over a 24 hour period of time. A possible explanation is that phosphorylated Lc molecules were protected from cleavage, but not all of them could be modified prior to concurrent proteolysis. An identical reaction mixture lacking the enzyme showed rapid cleavage of the Lc, with very little remaining by 4 hours, and undetectable by 8 hours. A monoclonal antibody to phosphorylated tyrosine reacted to full length, src phosphorylated Lc, but not to either of the cleavage products in the phosphorylation reaction, even though cleavage products were clearly visible by SDS-PAGE at all time points. The reaction lacking the enzyme showed no phosphorylated tyrosine bands of any size. Antibody to the amino terminus of the Lc reacted to the full length and larger of the cleavage products, plus three additional bands of between 60 and 75 kDa. These additional bands above the Lc were observed by SDS-PAGE for all the samples and appear to be SDS-resistant complexes of either the Lc or amino terminus fragment with other fragments. Autoradiographs of the phosphorylated and unphosphorylated (lacking enzyme) Lc show incorporation of [γ-$^{32}$P]ATP in the src phosphorylated full length Lc at 1 hour, with none observed in smaller or larger fragments, nor in samples lacking the enzyme. At 24 hours, very faint bands corresponding to the cleavage products did appear. These could either have arisen from cleaved, phosphorylated, full length Lc, or they may have been phosphorylated after they became fragments.

Example 28

Immunity

Immunization of mice with the purified forms of the LcA, LcA+Belt and LcA+Hn resulted in ELISA titers of between X and X for all construct forms. Protection was observed after challenge with $10^2$ to $10^3$ $MLD_{50}$ of purified Type A toxin. See Tables 6-8.

TABLE 6

Efficacy of Purified rBoNTA(LC + Belt) Solubly Expressed from *E. coli* to Elicit Protective Immunity in Mice

| Dosage [a, b] | Toxin Challenge (Survivors/Total) | | ELISA Titer |
|---|---|---|---|
| (μg) | $10^2$ $LD_{50}$ | $10^3$ $LD_{50}$ | (GMT) [c] |
| 5 | 10/10 | 10/10 | ND |
| 15 | 10/10 | 10/10 | ND |
| Controls | 0/10 | 0/10 | ND |

[a] Animals were vaccinated at 0, 2, and 4 weeks and challenged on week 6.
[b] Specific activity (i.e., proteolytic activity) of the rBoNTA(LC + Belt) immunogen was not determined.
[c] Geometric mean of the ELISA titer to BoNTA neurotoxin (ND = not determined).

TABLE 7

Efficacy of Purified rBoNTA(LC + Hn) Solubly Expressed from *E. coli* to Elicit Protective Immunity in Mice

| Dosage [a, b] | Toxin Challenge (Survivors/Total) | | ELISA Titer |
|---|---|---|---|
| (μg) | $10^2$ $LD_{50}$ | $10^3$ $LD_{50}$ | (GMT) [c] |
| 5 | 5/9 | 1/9 | ND |
| 15 | 4/10 | 1/10 | ND |
| Controls | 0/10 | 0/10 | ND |

[a] Animals were vaccinated at 0, 2, and 4 weeks and challenged on week 6.
[b] Specific activity (i.e., proteolytic activity) of the rBoNTA(LC + $H_n$) immunogen was not determined.
[c] Geometric mean of the ELISA titer to BoNTA neurotoxin (ND = not determined).

TABLE 8

Efficacy of Purified rBoNTA(LC) Solubly Expressed from *E. coli* to Elicit Protective Immunity in Mice

| Dosage [a, b] | Toxin Challenge (Survivors/Total) | | ELISA Titer |
|---|---|---|---|
| (μg) | $10^2$ $LD_{50}$ | $10^3$ $LD_{50}$ | (GMT) [c] |
| 5 | 9/10 | 10/10 | ND |
| 15 | 9/10 | 10/10 | ND |
| Controls | 0/10 | 0/10 | ND |

[a] Animals were vaccinated at 0, 2, and 4 weeks and challenged on week 6.
[b] Specific activity of the rBoNTB(LC) immunogen was 21 mmol/min/mg using 0.8-1.0 mM substrate (VAMP peptide, residues 54-94).
[c] Geometric mean of the ELISA titer to BoNTB neurotoxin (ND = not determined).

Example 29

Discussion

The system of expression of the invention for botulinum neurotoxin Hc (Byrne et al, 1998) and Lc fragments using an optimized synthetic gene, has previously shown success in achieving high levels of product. In an attempt to produce a molecule that more closely resembles the natural state of the toxin, a cloning and expression scheme that would give a large amount of correctly folded, untagged, Lc was initiated. The two basic strategies employed were to (1) express the Lc at a lower temperature, a classic method for ensuring proper folding, and (2) adding on portions of the rest of the neurotoxin polypeptide, mimicking the natural expression within the clostridial host. As expected, reducing the temperature for induction dramatically increased the solubility of the expressed product from 5.2% at 37° C. to 55.5% at 18° C. for the Lc. The slower rate of expression at the lower temperatures was compensated for by increasing the length of time for expression. This did not result in increased degradation of the product intracellularly, prior to harvest and purification. Addition of the belt and Hn portions of the toxin had no effect upon solubility of the expressed gene, although each was easily expressed at the lower temperature.

Although cloned and expressed Lc has been available for Lc study, it has been purified with either glutathione or his-tags (Zhou, et al, 1995; Li and Singh, 1999). Previous investigators have used native toxin (Lacy et al, 1998) for x-ray crystallography studies, and it was an object of the invention to produce Lc as close to the native product as possible, e.g., without tags or modifications. For this reason, traditional column chromatography methods were used instead of affinity columns. The calculated pI of the Lc of 8.13 suggested that the Lc would efficiently bind to a cation exchange column. Upon passage over an initial Mono S column, the product appeared relatively clean, although a second immunoreactive band immediately beneath the proper, calculated size for the Lc was noted. After passage over a second cationic exchange column, this band was not observed on Westerns.

Using the above methods of low temperature expression and cation exchange purification, a large quantity of Lc was acquired for assessment of catalytic activity. Activity of the purified Lc was calculated to be approximately 10-fold greater than that of the native toxin. Previous investigators have shown that the Lc must be activated by proteolytic cleavage of the Lc from the Hc (DasGupta and Dekleva, 1990), although the two halves must both be present for efficient intoxication of cells. It is interesting that the Lc with the belt attached lacked the high level of catalytic activity seen with the Lc by itself. Presumably, the belt is wrapped around the Lc, as is observed in x-ray crystallography studies (Lacy et al, 1998). As the entire translocation region is not there to occlude the active site, it may be that the belt in some manner is constricting the Lc, or a conformational change is prevented that is required for full activation. Comparison of the crystallography structure of Lc of the invention with and without the belt would be worth further study.

Two interesting and unexpected pieces of data came from expression of Lc without purification tags. The first was the truncation of the Lc from the carboxy terminus by 20 residues. A recent paper by Kadkhodayan et al, 2000, notes that this portion of the Lc is not required for full catalytic activity. The truncation is intriguing as it removes the Lc/Hc di-sulfide bond at a lysine proximal to the involved cysteine. The two other proteolytic cleavages known to occur at the carboxy terminus of the Lc are also at lysine residues (DasGupta and Dekleva, 1990). Lysine proteolysis is common, with ubiquitin, a lysine specific proteolysis factor found conjugated to cell receptors of eukaryotes being one of the most common routes (Doherty and Mayer, 1992). It has long been hypothesized that the di-sulfide bond holding the Lc and Hc together was reduced as the Lc was transported into the cell, freeing it from the receptor binding portion (de Paiva et al, 1993). Although the ten residue portion flanked by lysine residues seems to be removed during activation "nicking" of the polypeptide, the cysteine residue was assumed to remain as part of the Lc. Work with native toxin and cells has been initiated to determine if the natural state of the toxin inside cells is one lacking the terminal 20 residues and cysteine.

Example 30

Expression of BoNT LC

Reagents: Terrific Broth (Difco): 48 gm/liter with 4 ml of non-animal glycerol; autoclave 15 minutes. Store refrigerated. Kanamycin: stock solution is 50 mg/ml in distilled water, filter sterilized, store in aliquots at −20° C. Chloramphenicol: stock solution is 50 mg/ml in ethanol, filter sterilized, store in aliquots at −20° C. Add antibiotics to media just prior to use.

Expression of the Lc and Lc with Hc (translocation region) was performed for even numbered SEQ ID NOS:20-44. Expression was essentially the same for all constructs within the given parameters.

Cultures of BL21(DE3) cells were grown in Terrific Broth (TB) plus 50 μg/mL kanamycin. Cultures of BL21(DE3) Codon Plus cells were grown in TB plus 50 μg/mL kanamycin and 50 μg/mL chloramphenicol. Cultures grown overnight at 37° C. while shaking at about 200 to about 250 rpm were diluted 1:20 with fresh antibiotic-containing media. Diluted cultures were returned to overnight growth conditions (37° C., shaking at 200-250 rpm) for 1¼ to 2¼ hours. An optical density measurement was taken while the cultures were placed on ice for 5 minutes. Preferably, the $OD_{600}$ is between about 0.4 and about 0.6. The incubation time may be extended and/or fresh antibiotic-containing media may be added if the $OD_{600}$ is lower than 0.4 or higher than 0.6.

Next, sufficient IPTG was added to each chilled culture to make the concentration about 1 mM. IPTG-containing cultures were incubated about 24 to about 26 hours at 18° C. and shaking at about 200 to about 250 rpm. An optical density measurement was taken at the end of this incubation. Preferably, the $OD_{600}$ is between about 1.7 and about 2.1.

Cultures that satisfied this criteria were centrifuged at about 3000 rpm for about 20 minutes to obtain a cell paste for purification. The cell paste may be stored at −20° C. until ready for use.

Aliquots of 1 mL each were pelleted in a microfuge, resuspended in 1 mL of sonication buffer, and sonicated 12×30 seconds on ice over 12 minutes. Sonicated cells were microfuged for 10 minutes. The supernatant was aspirated and retained as the soluble fraction. 1 mL of 6M urea was added to each pellet and retained as the insoluble fraction. Appropriate amounts run on by SDS-PAGE should show approximately 50% soluble, 50% insoluble, at about 51 kDa. A western with rabbit anti-Lc sera will be at the same location.

Purification of BoNT LC

Cell paste was resuspended at 1 g/20 mL sonication buffer, sonicated 10×, 30 seconds on, 30 seconds off, on ice. Insoluble material and debris was pelleted by centrifuging for 10 minutes at 12,000 rpm (e.g. in a microfuge), decanting solute, and repeating one time in a fresh tube. The supernatant was decanted into a fresh tube. An equal volume of equilibration buffer may be optionally added to the supernatant to facilitate cation exchange chromatography, e.g., flow. For example, such dilution facilitates column loading and washing when using a Source S resin from Pharmacia whereas such dilution is unnecessary when using a Poros cationic resin. Filter sterilize the supernatant with 0.45 μm filters.

Run #1: A column (100 mm) was equilibrated with equilibration buffer, 2 minutes, 2.5 to, 3 ml/min (same rate through out run). Cell paste (20-40 mL per run) was manually loaded. The column was washed for 3 minutes with equilibration buffer. Using gradient buffer, a 0 to 70% gradient was run over 8 minutes. For some cell lysates, a 5% NaCl (5 mS) 5 minutes step was performed. For example, where a Source S resin was used, no salt wash was performed, but where a Poros resin was used, this salt wash was performed to elute contaminating proteins. Cell protein was collected at between 10 and 22 mS. Fractions (1 mL) were collected through out the gradient. The desired protein will elute at between 10 and 22 mS, depending upon the expression product used.

Run #2: The peak fractions from run #1 were pooled. Equilibration buffer was added to pooled fractions, at a 3:1 ratio. The column was equilibrated with equilibration buffer for 2 minutes, at 2.5 to 3 ml/min (same rate through out run). The run #1 pool was loaded onto the column; washed 2 minutes with equilibration buffer. Using gradient buffer, a 0 to 75% gradient was run over 15 minutes. Fractions (1 mL) were collected and peak fractions were pooled. Aliquots of the pooled fractions were stored in plastic vials at −20° C.

A portion of the purified protein was used to measure the $A_{260/278}$. The ratio may be used as a measure of the presence of DNA and the $A_{280}$ to quantitate the protein by using the calculated molar extinction coefficient and molecular weight.

A cleaning procedure must be done on the column between each run. Run 1 M NaCl through column at 3 ml/min for 5 minutes. Run 20 mM NaOH through the column at 1 ml/min for 10 minutes. Run 70% ETOH through the column at 1 ml/min for 30 minutes. Run 1 M NaCl through it at 1 ml/min for 15 minutes. Re-equilibrate the column to the proper pH with a low salt buffer.

Buffers

A combination of sonication buffers, equilibration buffers and gradient buffers is used for each cell lysate. Sonication buffers are always chosen to be 0.4 pH below the equilibration buffer. Gradient buffers are the same as equilibration buffers except for addition of 1 M NaCl.

Gradient buffer A: 55 mM Na mono-phosphate, 2 mM EDTA, 1 M NaCl, in milliQ water; pH to 5.8; filter. Gradient buffer B: 20 mM NaAcetate, 1 M NaCl, in milliQ water, pH to 5.4, filter. Gradient buffer C1: 20 mM NaAcetate, 1 M NaCl, in milliQ water, pH to 4.8, filter. Gradient buffer C2: 20 mM NaAcetate, 2 mM EDTA, 1 M NaCl, in milliQ water, pH to 5.4, filter. Gradient buffer D: 20 mM NaAcetate, 2 mM EDTA, 1 M NaCl, in milliQ water, pH to 4.8, filter.

Results

Expression and purification of BoNT/A LC according to this method yielded protein with a specific activity (SNAP-25 assay) that was about 10-fold higher than when BoNT/A LC was purified from inclusion bodies (Ahmed and Smith (2000) J. Prot Chem. 19, 475-487).

REFERENCES

The references cited throughout this application and listed below are incorporated herein in their entirety by reference.

Adler, M., Dinterman, R. E., and Wannemacher, R. W. (1997). *Toxicon* 35, 1089-1110.

Ahmed, S. A. and Claiborne, A. (1992). *J. Biol. Chem.* 267, 3822-3840.

Ahmed, S. A. and Smith, L. A. (2000). *J. Protein Chem.* 19, 475-487.

Ahmed, S. A., Byrne, M. P., Jensen, M., Hines, H. B., Brueggemann, E., and Smith, L. A. (2001). *J. Protein Chem.* 20, 221-231.

Ahmed, S. A., Fairwell, T., Dunn, S., Kirschner, K., and Miles, E. W. (1986). *Biochemistry* 25, 3118-3124.

Alderton, J. M., Ahmed, S. A., Smith, L. A., and Steinhardt, R. A. (2000). *Cell. Calcium* 28, 161-169.

Andersson, S. G., and Kurland, C. G. (1990). *Microbial. Rev.* 54, 198-210.

Auld, D. S. (1995). *Meth. EnUmol.* 248, 228-242.

Bi, G. Q., Alderton, J. M., and Steinhardt, R. A. (1995). *J. Cell Biol.* 131, 1747-1758.

Bittner, M. A., DasGupta, B. R., and Holz, R. W. (1989). *J. Biol. Chem.* 264, 10354-10360.

Black, J. D., and Dolly, J. O. (1986). *J. Cell Biol.* 103, 535-544.

Blasi, J., Chapman, E. R., Link, E., Binz, T., Yamasaki, S., De Camilli, P., Sudhof, T. C. Niemann, H., and Jahn, R. (1993). *Nature* 365, 160-163.

Cai, S., Sarkar, H. K., and Singh, B. R. (1999). *Biochemistry* 38, 6903-6910.

Cardoso F, Jankivic J (1995). Clinical use of botulinum neurotoxins. In *Current Topics in Microbiology and Immunology* (Capron A et al., eds.), Springer-Verlag, Germany, pp. 123-141.

Chen, F., Kuziemko, G. M., Amersdorfer, P., Wong, C., Marks, J. D., and Stevens, R. C. (1997). *Infect. Immun.* 65, 1626-1630.

Claiborne, A., Yeh, J. I., Mallett, T. C., Luba, J., Crane, E. J., 3rd, Charrier, V., and Parsonage, D. (1999). *Biochemistry* 38, 15407-15416.

Creighton, T. E. (1984). *Proteins, Structures and Molecular Properties*, Freeman, N.Y.

Dalbey, R. E. and Kahn, A. (2000). *Annu. Rev. Cell Dev. Biol.* 16, 51-87.

DasGupta, B. R., and Dekleva, M. L. (1990). *Biochimie* 72, 661-664.

DasGupta, B. R., and Foley, J., Jr. (1989). *Biochimie* 71, 1193-1200.

Dekleva, M. L. and DasGupta, B. R. (1990). *J. Bacteriol.* 172, 2498-2503.

de Paiva, A., Poulain, B., Lawrence, G. W., Shone, C. C., Tauc, L., and Dolly, J. O. (1993). *J. Biol. Chem.* 268, 20838-20844.

Dertzbaugh, M. T., and West, M. W. (1996). *Vaccine* 14, 1538-1544.

Ettinger, R. A., Liu, A. W., Nepom, G. T., and Kwok, W. W. (2000). *J. Immunol* 165, 3232-3238.

Foran, P., Shone, C. C., and Dolly, J. O. (1994). *Biochemistry* 33, 15365-15374.

Foran, P., Lawrence, G. W., Shone, C. C., Foster, K. A., and Dolly, J. O. (1996). *Biochemistry* 35, 2630-2636.

Fu, F. N., Lomneth, R. B., Cai, S., and Singh, B. R. (1998). *Biochemistry* 37, 5267-5278.

Kadkhodayan, S., Knapp, M. S., Schmidt, J. J., Fabes, S. E., Rupp, B., and Balhorn, R. (2000). *Protein Expr. Purif.* 19, 125-130.

Kiyatkin, N., Maksymowych, A. B., and Simpson, L. L. (1997). *Infect. Immun.* 65, 4586-4591.

Klatt, P., Schmidt, K., Lehner, D., Glatter, O., Bachinger, H. P., and Mayer, B. (1995). *EMBO J.* 14, 3687-3695.

Knapp, M., Segelke, B., Balhorn, R., and Rupp. B. (2000). The crystal structure of botulinum toxin A zinc protease domain. Presented at the 37th Annual Meeting of the Interagency Botulinum Research Coordinating Committee, Alisomar, Calif.

Kreiglstein, K. G., DasGupta, B. R., and Henschen, A. H. (1994). *J. Protein Chem.* 13, 49-57.

Kurazono, H. Mochida, S., Binz, T., Eisel, U., Quanz, M., Grebenstein, O., Wetnars, K., Poulain, B., Tauc, L., and Niemann, H. (1992). *J. Biol. Chem.* 267, 14721-14729.

Lacy, D. B., and Stevens, R. C. (1999). *J. Mol. Biol.* 291, 1091-1104.

Lacy, D. B., Tepp, W., Cohen, A. C., DasGupta, B. R., and Stevens, R. C. (1998). *Nature Struct. Biol.* 5, 898-902.

Laemmli, U. K. (1970). *Nature* 227, 680-685.

Lebeda, F. J., and Olson, M. A. (1994). *Proteins* 20, 293-300.

Li, L., and Singh, B. R. (1999). *Protein Expr. Purif.* 17, 339-344.

Li, L. and Singh, B. R. (2000). *Biochemistry* 39, 10581-10586.

Li, Y., Foran. P., Fairweather, N. F., de Paiva, A., Weller, U., Dougan, G., and Dolly, J. O. (1994). *Biochemistry* 33, 7014-7020.

Maisey, E. A., Wadsworth, J. D., Poulain, B., Shone, C. C., Melling. J. Gibbs, P., Tauc, L., and Dolly, J. O. (1988). *Eur. J. Biochem.* 177, 683-691.

Makoff, A. J., Oxer, M. D., Romanos, M. A., Fairweather, N. F., and Ballantine, S. (1989). *Nucleic Acids Res.* 17, 10191-10202.

Montal, M. S., Blewitt, R., Tomich, J. M., and Mortal, M. (1992). *FEBS Lett.* 313, 12-18.

Montecucco, C., and Schiavo, G. (1994). *Mol. Microbiol.* 13, 1-8.

Montecucco, C., and Schiavo, G. (1995). *Q. Rev. Biophys.* 28, 423-472.

Nowakowski, J. L., Courtney, B. C., Bing, Q. A., and Adler, M. (1998). *J. Protein Chem.* 17, 453-462.

Pace, C. N., Vajdos, F., Fee, L., Grimsley, G., and Gray, T. (1995). *Protein Sci.* 4, 2411-2423.

Rossetto, O., Schiavo, G., Montecucco, C., Poulain, B., Deloye, F. Lozzi, L., and Shone, C. C. (1994). *Nature* 372, 415-416.

Schiavo, G., Rossetto, O., Catsicas, S., Polverino de Laureto, P., DasGupta, B. R., Benfenati, F., and Montecucco, C. (1993). *J. Biol. Chem.* 268, 23784-23787.

Schiavo, G., Malizio, C., Trimble, W. S., Polverino de Laureto, P. Milan, G., Sugiyama, H., Johnson, E. A., and Montecucco, C. (1994). *J. Biol. Chem.* 269, 20213-20216.

Schiavo, G. Rossetto, Tonello, F., and Montecucco, C. (1995). Intracellular targets and metalloprotease activity of tetanus and botulinum neurotoxins. In *Clostridial Neurotoxins: The Molecular Pathogenesis of Tetanus and Botulism* (Montecucco, C., ed.), Springer, New York, pp. 257-273.

Schmidt, J. J., and Bostian. K. A. (1995). *J. Protein Chem.* 14, 703-708.

Schmidt, J. J., and Bostian. K. A. (1997). *J. Protein Chem.* 16, 19-26.

Schmidt, J. J., Stafford R G, Millard C B (2001). *Analytical Biochemistry* 296, 130-137.

Shone, C. C., and Roberts, A. K. (1994). *Eur. J. Biochem.* 225, 263-270.

Shone, C. C., and Tranter, H. S. (1995). *Curr. Top. Microbiol. Immunol.* 195, 143-160.

Shone, C. C., Quinn, C. P., Wait, R., Hallis, B., Fooks, S. G., and Hambleton, P. (1993). *Eur. J. Biochem.* 217, 965-971.

Schagger, H. and von Jagow, G. (1987). *Anal. Biochem.* 166, 368-379.

Schmidt, J. J., Stafford, R. G., and Bostian, K. A. (1998). *FEBS Lett.* 435, 61-64.

Sheridan, R. E., Deshpande, S. S., Nicholson, J. D., and Adler, M. (1997). *Toxicon* 35, 1439-1451.

Simpson, L. L., Coffield, J. A., and Bakry, N. (1993). *J. Pharmacol. Exp. Ther.* 267, 720-727.

Smith, L. A. (1998). *Toxicon* 36, 1539-1548.

Steinhardt, R. A., Bi, G., and Alderton, J. M. (1994). *Science* 263, 390-393.

Strasser, A., O'Connor, L., and Dixit, V. M. (2000). *Annu. Rev. Biochem* 69, 217-245.

Syuto, B., and Kubo, S. (1981). *J. Biol. Chem.* 256, 3712-3717.

Thompson, D. E., Brehm, J. K., Oultram, J. D., Swinfield, T. J., Shone, C. C. Atkinson, T., Melling, J., and Minton, N. P. (1990). *Eur. J. Biochem.* 189, 73-81.

Washbourne, P., Pellizzari, R. Baldini, G., Wilson, M. C., and Montecucco, C. (1997). *FEBS Lett.* 418, 1-5.

Winkler, H. H., and Wood, D. O. (1988). *Biochimie* 70, 977-986.

Zhou, L., de Paiva, A., Liu, D., Aoki, R., and Dolly, J. O. (1995). *Biochemistry* 34, 15175-15181.

We claim:

1. A method for producing a botulinum neurotoxin light chain comprising: culturing, at a temperature of about 18° C., a host cell comprising an expression control sequence operably linked to a nucleic acid sequence encoding the botulinum neurotoxin light chain; expressing the botulinum neurotoxin light chain; obtaining a protein fraction from the cultured host cell; and isolating the botulinum neurotoxin light chain from the protein fraction, wherein more than 100 mg of botulinum neurotoxin light chain is obtained per liter of culture.

2. The method of claim 1 wherein the host cell is *Pichia pastoris*.

3. The method of claim 1 wherein the host cell is *Escherichia coli*.

4. The method of claim 1 wherein the botulinum neurotoxin light chain is non-toxic.

5. The method of claim 1 wherein more than 500 mg of purified botulinum neurotoxin light chain is obtained per liter of culture.

6. The method of claim 1 wherein about 1 gram of purified botulinum neurotoxin light chain is obtained per liter of culture.

7. The method of claim 1 wherein the purified botulinum neurotoxin light chain is catalytically active.

8. The method of claim 1 wherein the nucleic acid has the sequence of nucleotides 9-1337 of SEQ ID NO:4.

9. The method of claim 1 wherein the nucleic acid sequence encodes a botulinum neurotoxin light chain serotype A.

10. The method of claim 1 wherein the nucleic acid sequence encodes a botulinum neurotoxin light chain selected from the group consisting of botulinum neurotoxin light chain serotype B, botulinum neurotoxin light chain serotype $C_1$, botulinum neurotoxin light chain serotype D, botulinum neurotoxin light chain serotype E, botulinum neurotoxin light chain serotype F, and botulinum neurotoxin light chain serotype G.

11. The method of claim 1 wherein the nucleic acid has a total A+T content that is less than about 70%.

12. The method of claim 1 wherein the nucleic acid molecule encodes a polypeptide having an amino acid sequence selected from the group consisting of SEQ ID NO:47 and SEQ ID NO:21.

13. The method of claim 1 wherein the A+T content of any 50 consecutive nucleotides of the nucleic acid molecule is less than about 75%.

14. The method of claim 10 wherein the nucleic acid has a nucleic acid sequence selected from the group consisting of SEQ ID NO: 6, 8, 10, 12, 14, 16, 22, 26, 30, 34, 38, and 42.

15. The method of claim 10 wherein the nucleic acid has a total A+T content that is less than about 70%.

16. The method of claim 10 wherein the A+T content of any 50 consecutive nucleotides of the nucleic acid molecule is less than about 75%.

17. The method of claim 10 wherein the nucleic acid molecule encodes a polypeptide having an amino acid sequence selected from the group consisting of SEQ ID NO:7, SEQ ID NO:9, SEQ ID NO:11, SEQ ID NO:13, SEQ ID NO:15, SEQ ID NO:17, SEQ ID NO:23, SEQ ID NO:27, SEQ ID NO:31, SEQ ID NO:39, and SEQ ID NO:43.

18. The method of claim 1 wherein the DNA molecule has the nucleic acid sequence specified in SEQ ID NO:20.

* * * * *